United States Patent
Lee et al.

(10) Patent No.: US 8,466,161 B2
(45) Date of Patent: Jun. 18, 2013

(54) HYDROXAMATE DERIVATIVE, A PRODUCTION METHOD FOR THE SAME, AND A PHARMACEUTICAL COMPOSITION COMPRISING THE SAME

(75) Inventors: Sung Sook Lee, Cheonan-si (KR); Kyung Joo Lee, Cheonan-si (KR); Chang Sik Lee, Cheonan-si (KR); Hyun Mo Yang, Cheonan-si (KR); Do Hoon Kim, Cheonan-si (KR); Dae Kyu Choi, Cheonan-si (KR); Ho Jin Choi, Cheonan-si (KR); Dal Hyun Kim, Cheonan-si (KR); In Chang Hwang, Cheonan-si (KR); Mi Jeong Kim, Cheonan-si (KR); Byeong Hoon Han, Cheonan-si (KR)

(73) Assignee: Chong Kun Dang Pharmaceutical Corp., Seoul (KR)

( * ) Notice: Subject to any disclaimer, the term of this patent is extended or adjusted under 35 U.S.C. 154(b) by 0 days.

(21) Appl. No.: 13/258,630

(22) PCT Filed: Mar. 18, 2010

(86) PCT No.: PCT/KR2010/001656
§ 371 (c)(1),
(2), (4) Date: Sep. 22, 2011

(87) PCT Pub. No.: WO2010/110545
PCT Pub. Date: Sep. 30, 2010

(65) Prior Publication Data
US 2012/0028963 A1    Feb. 2, 2012

(30) Foreign Application Priority Data
Mar. 27, 2009    (KR) .................. 10-2009-0026578

(51) Int. Cl.
*A61K 31/506* (2006.01)
*A61K 31/4439* (2006.01)
*A61K 31/416* (2006.01)
*A61K 31/404* (2006.01)
*A61K 31/4184* (2006.01)
*C07D 403/04* (2006.01)
*C07D 401/04* (2006.01)
*C07D 213/74* (2006.01)
*C07D 231/56* (2006.01)
*C07D 209/08* (2006.01)

(52) U.S. Cl.
USPC ........... 514/256; 514/339; 514/394; 514/403; 514/415; 544/331; 546/268.1; 546/304; 548/306.1; 548/361.1; 548/466

(58) Field of Classification Search
USPC .................... 562/621; 548/495; 514/645, 419
See application file for complete search history.

(56) References Cited

U.S. PATENT DOCUMENTS

| 771,760 | A | 10/1904 | Balch |
| 6,034,096 | A | 3/2000 | Bertolini et al. |
| 2007/0060614 | A1 | 3/2007 | Bacopoulos et al. |

FOREIGN PATENT DOCUMENTS

| EP | 0847992 B1 | 6/2004 |
| WO | 93/07148 | 4/1993 |
| WO | 95/31977 | 11/1995 |
| WO | 02/22577 A2 | 3/2002 |
| WO | 02/30879 A2 | 4/2002 |
| WO | 2004/069823 A1 | 8/2004 |
| WO | 2004/110989 A1 | 12/2004 |
| WO | WO 2008/033747 A2 | 3/2008 |

OTHER PUBLICATIONS

Bryn, 1999, SSCI, Inc, 2nd Edition, p. 233-247.*
Cancer Prevention Overview, http://www.cancer.gov/cancertopics/pdq/prevention/overview/patient, accessed Nov. 14, 2012.*
Golub, 1999, Science, vol. 286, p. 531-537.*

(Continued)

*Primary Examiner* — Wu-Cheng Winston Shen
*Assistant Examiner* — Karen Cheng
(74) *Attorney, Agent, or Firm* — Heslin Rothenberg Farley & Mesiti P.C.

(57) ABSTRACT

The present invention relates to hydroxamate compounds of the following formula I, an isomer, pharmaceutically acceptable salt or hydrate thereof. The present invention also relates to a method for preparing the hydroxamate compounds, comprising allowing a compound of the following formula II to react with bromoaniline in the presence of an inorganic salt so as to prepare a compound of the following formula III. Moreover, the invention relates to a method for treating specific diseases by administering the compositions containing the hydroxamate compounds

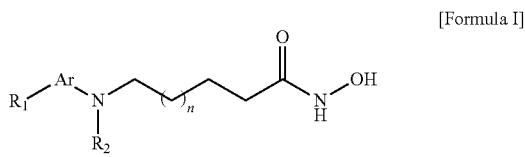

[Formula I]

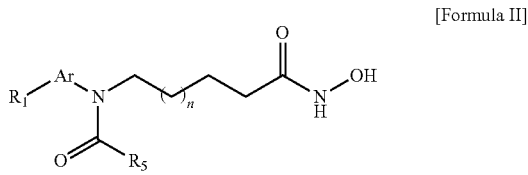

[Formula II]

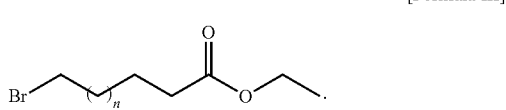

[Formula III]

10 Claims, 6 Drawing Sheets

OTHER PUBLICATIONS

Target Cancer Therapies, http://www.cancer.gov/cancertopics/factsheet/therapy/targeted, accessed Jun. 21, 2010.*

Voskoglou-Nomikos et al, 2003, Clinical Cancer Research, vol. 9, p. 4227-4239.*

Marks, Paul A. et al., Histone Deacetylases and Cancer: Causes and Therapies, Macmillan Magazines Ltd., vol. 1, Dec. 2001, pp. 194-202.

Li, Side et al., Transcriptional Repression of the Cystic Fibrosis Transmembrane Conductance Regulator Gene, Mediated by CCAAT Displacement Protein/cut Homolog, Is Associated with Histone Deacetylation, The Journal of Biological Chemistry, vol. 274, No. 12, The American Society for Biochemistry and Molecular Biology, Inc., 1999, pp. 7803-7815.

Steffan, Joan S. et al., Histone deacetylase inhibitors arrest polyglutamine-dependent neurodegeneration in *Drosophila*, Nature, vol. 413, Macmillan Magazines Ltd., Oct. 18, 2001, pp. 739-743.

Gabbianelli Marco et al., Hemoglobin switching in unicellular erythroid culture of sibling erythroid burst-forming units: kit ligand induces a dose-dependent fetal hemoglobin reactivation potentiated by sodium butyrate, Blood, vol. 95, No. 11, The American Society of Hematology, Jun. 1, 2000, pp. 3555-3561.

Emanuele, Sonia et al., Histone deacetylase inhibitors: Apoptotic effects and clinical implications (Review), International Journal of Oncology, 33, 2008, pp. 637-646.

Marks, Paul A. et al., Histone deacetylase inhibitors as new cancer drugs, Current Opinion in Oncology, 13, Lippincott Williams & Watkins, Inc., 2001, pp. 477-483.

Johnstone, Ricky W., Histone-Deacetylase Inhibitors: Novel Drugs for the Treatment of Cancer, Drug Discovery, Nature Reviews, vol. 1, Apr. 2002, pp. 287-299.

Maiso, Patricia, et al., The Histone Deacetylase Inhibitor LBH589 Is a Potent Antimyeloma Agent that Overcomes Drug Resistance, Cancer Research, 66, 2006, pp. 5781-5789.

Dokmanovic, Milos et al., Histone Deacetylase Inhibitors: Overview and Perspectives, Molecular Cancer Research, 5 (10), American Association for Cancer Research, 2007, pp. 981-989.

Morris, Gregory A. et al., A general route to pyridine-modified salicylaldehydes via Suzuki coupling, Tetrahedron Letters, 42, Elsevier Science Ltd., 2001, pp. 2093-2096.

* cited by examiner

HYDROXAMATE DERIVATIVE, A PRODUCTION METHOD FOR THE SAME, AND A PHARMACEUTICAL COMPOSITION COMPRISING THE SAME

TECHNICAL FIELD

The present invention relates to novel hydroxamate derivatives, and more particularly to novel hydroxamate derivatives having histone deacetylase inhibitory activity, isomers thereof, pharmaceutically acceptable salts thereof, hydrates thereof, or solvates thereof, the use thereof for preparing pharmaceutical compositions, pharmaceutical compositions containing the same, a method of treating disease using the compositions, and a method for preparing novel hydroxamate derivatives.

BACKGROUND ART

Histone deacetylase (HDAC) activity is involved in a number of disease states, for example, cancer (Marks et al., Nature Reviews, 1, 194-202, 2001), cystic fibrosis (Li. S. et al, J. Biol. Chem., 274, 7803-7815, 1999), Huntington's chorea (Steffan, J. S. et al., Nature, 413, 739-743, 2001), and sickle cell anaemia (Gabbianelli. M. et al., Blood, 95, 3555-3561, 2000).

Thus, studies on the regulation of transcription of histone acetylases (HATs) and histone deacetylases (HDACs), which are involved in chromatin structure, have been actively conducted. It is known that histone acetylases are enzymes that catalyze the acetylation of N-terminal histone tails to cause an unstable chromatin structure, whereas histone deacetylases remove acetyl groups from histones to stabilize chromatin structure so as to interfere with the accession of transcription factors to target genes, thereby inhibiting transcriptional activity. Acetylation of histones is regulated by histone deacetylases that catalyze the removal of acetyl groups from the lysine residues of histones. If acetyl groups are attached to histone proteins, the expression of proteins that are involved in the suppression of cancer will be stimulated, but if the acetyl groups are removed from histone proteins, the expression of proteins that are involved in the suppression of cancer will be inhibited. Thus, inhibition of histone deacetylase (HDAC) activity leads to arrest of the cell cycle, inhibition of blood vessel formation, immune regulation, cell death, etc. Namely, if the enzymatic activity of histone deacetylases is inhibited, the activity of factors associated with the survival of cancer cells in vivo will be inhibited, and the activity of factors associated with the death of cancer cells will be increased, whereby the death of cancer cells will be induced. Recent studies on histone modification enzymes revealed that histone deacetylases play an important role in tumor formation. 11 members-cloned HDAC, which is expressed from humans, is over-expressed in several tumor cells, and in this state, the expression of tumor suppressors such as p53 and p21 is inhibited, but tumor activators, such as hypoxia-induced factor-1 and vascular endothelial growth factor (VEGF), are up-regulated. Particularly, a decrease in tubulin acetylation that is mediated by histone deacetylases was observed in patients suffering from neurodegenerative diseases such as Alzheimer's disease.

Thus, it has been recognized that inhibition of histone deacetylase activity can be applied for the treatment of cancer and other diseases. In fact, inhibition of histone deacetylase activity by a specific inhibitor results in changes in the acetylation of proteins at the molecular and cellular levels, the expression of a specific gene, and the morphology, proliferation and migration of cells.

Histone deacetylase inhibitors found to date can be divided, according to their structure, into four categories: 1) short-chain fatty acids (e.g., butyric acid and valproic acid); 2) hydroxamic acids (e.g., trichostatin A, SAHA and oxamflatin); 3) cyclic peptides (e.g., depsipeptide and Trapoxin); and 4) benzamides (e.g., MS-275, MGCD 0103, and CI-994) (International Journal of oncology 33, 637-646, 2008). These histone deacetylase inhibitors (SAHA, pyroxamide, scriptide, oxamfiatin, NVP-LAQ-824, CHAPs and MS-275) effectively induce the growth inhibition, differentiation and apoptosis of various transformed cells in animal models and media (Marks, P. A et al., Curr Opin. oncol. 2001, 13, 477-483), and HDAC inhibitors, such as SAHA, NVP-LAQ-824 and MS-275, have been evaluated in clinical trials for the treatment of various cancer diseases (Johnstone. R. W Nat. Rev. Drug Discov. 2002, 1, 287-299). Typical examples of HDAC inhibitor compounds that are currently known include hydroxamate compounds, such as SAHA (U.S. Pat. No. 771, 760, Zolinza, vorinostat), PXD101 (WO 02/30879, Belinostat) and LBH589 (WO 02/22577, Panobinostat), and benzamide compounds, such as MS275 (EP 847992) and MGCD0103 (WO 04/69823). Of these compounds, SAHA, a typical HDAC inhibitor, was approved in October 2006 by the US FDA and has been used for the treatment of cutaneous T-cell lymphoma (CTCL). The range of diseases to which SAHA can be applied is being additionally expanded, but it is known that the effect of SAHA is insufficient (Cancer Res 2006, 66, 5781-5789).

Although many HDAC inhibitors have been reported to date, there has been a continuous need for a more selective, more effective HDAC inhibitor which overcomes the above-described disadvantage (Mol Cancer Res, 5, 981, 2007).

The present inventors have conducted many studies to develop agents for treating the above-mentioned diseases and, as a result, have developed derivatives which are completely different from known compounds, thereby completing the present invention.

DISCLOSURE

Technical Problem

It is an object of the present invention to provide novel hydroxamate derivatives, isomers thereof, pharmaceutically acceptable salts thereof, hydrates thereof, or solvates thereof.

Another object of the present invention is to provide pharmaceutical compositions for prevention or treatment of diseases associated with histone deacetylase activity, which contain novel hydroxamate derivatives, isomers thereof, pharmaceutically acceptable salts thereof, hydrates thereof, or solvates thereof, and methods of preventing or treating the diseases using the compositions.

Still another object of the present invention is to provide a method for preparing novel hydroxamate derivatives.

Technical Solution

In accordance with one aspect of the present invention, there are provided hydroxamate derivatives represented by the following formula I, isomers thereof, pharmaceutically acceptable salts thereof, hydrates thereof, or solvates thereof

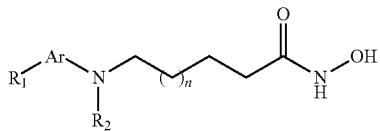

[Formula I]

wherein n is an integer of 2, 3 or 4;

Ar is a phenyl, pyridine or pyrimidine group which is unsubstituted or substituted with one or more substituents selected from the group consisting of $C_{1-6}$ alkyl, amino, nitro, thiomethyl, hydroxyl, nitrile, carboxyl, $C_{1-4}$ alkyloxy, aryl $C_{1-4}$ alkyloxy, halogen, trifluoromethyl, —O—$CF_3$, phenyl and phenoxy groups;

$R_1$ is an indole, indazole or benzimidazole group which is unsubstituted or substituted with one or more substituents selected from the groups consisting of $C_{1-6}$ alkyl, formyl, amino, nitro, thiomethyl, hydroxyl, $C_{1-6}$ alkoxy, nitrile, carboxyl, halogen, trifluoromethyl, —O—$CF_3$, —C(O)—$R_5$, —S($O_2$)—$R_5$ and

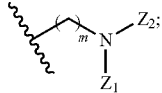

and $R_2$ is hydrogen, hydroxy $C_{1-6}$ alkyl, $C_{1-8}$ alkyl, —C(O)—$R_5$, —C(O)NH—$R_5$, —S($O_2$)—$R_5$, —C(S)—$R_5$ or —C($O_2$)—$R_5$, in which $R_5$ is

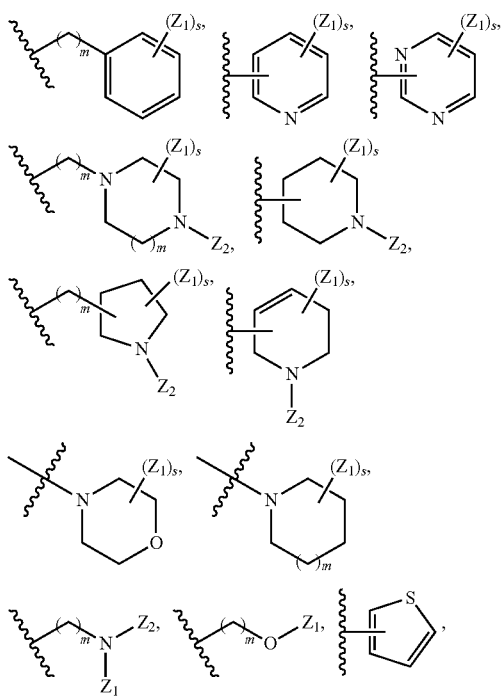

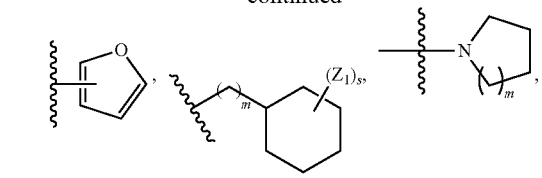

naphthyl, $C_{1-8}$ alkyl or $C_{1-4}$ alkyloxy group, $Z_1$ and $Z_2$ are each independently hydrogen, $C_{1-6}$ alkyl, amino, —O—$C_{1-4}$ alkyl, —S($O_2$)$C_{1-4}$ alkyl, —C(O)$C_{1-4}$ alkyl, —S—$C_{1-4}$ alkyl, halogen, trifluoromethyl, —O—$CF_3$, phenyl, —O-phenyl, —O—$C_{1-4}$ alkylaryl,

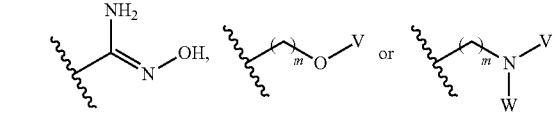

V and W are each independently hydrogen or $C_{1-6}$alkyl,

Each s is independently an integer of 0, 1, 2, 3, 4 or 5, and

Each m is independently an integer of 0, 1, 2 or 3.

Advantageous Effects

The hydroxamate derivatives according to the present invention have histone deacetylase inhibitory activity and kill the actively proliferating cells of malignant tumors. Thus, the hydroxamate derivatives of the present invention can be used as agents for treating malignant tumors, viral and bacterial infections, vascular restenosis, inflammatory diseases, autoimmune diseases, and psoriasis.

BEST MODE

Figure 1:
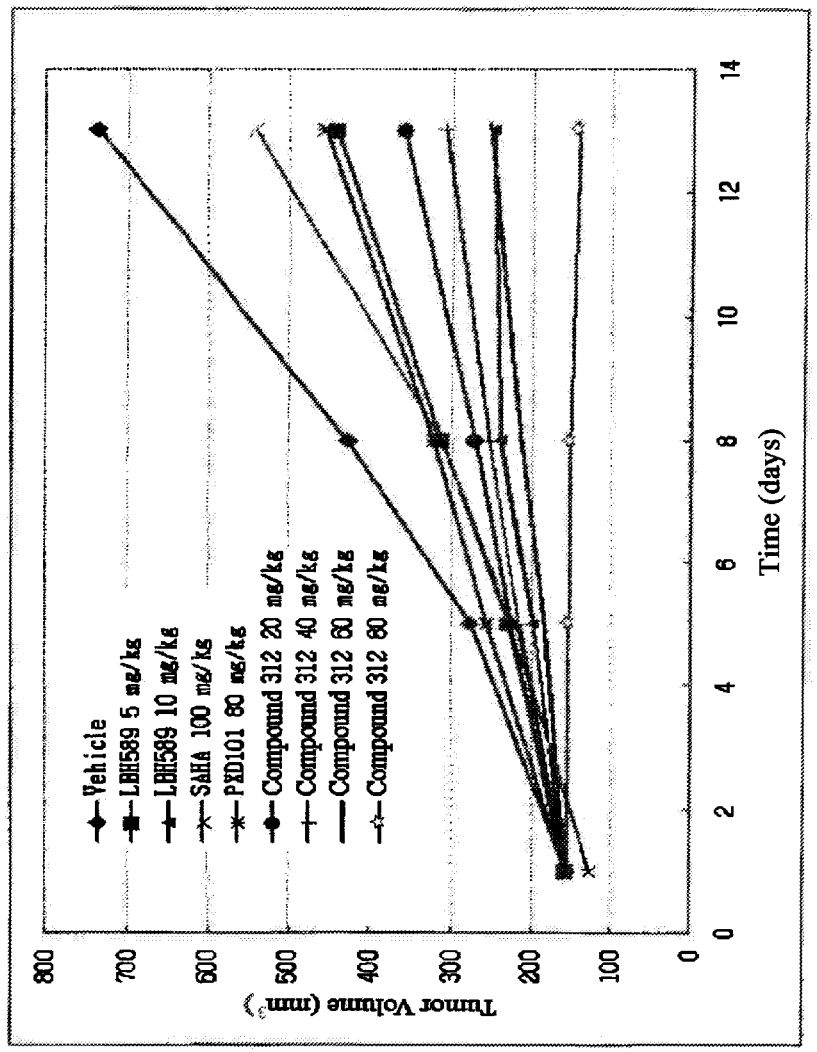
FIGS. 1, 2, 3, 4 and 5 show the results of measuring the anticancer effects of compounds according to the present invention in xenograft animal models.
Figure 2:
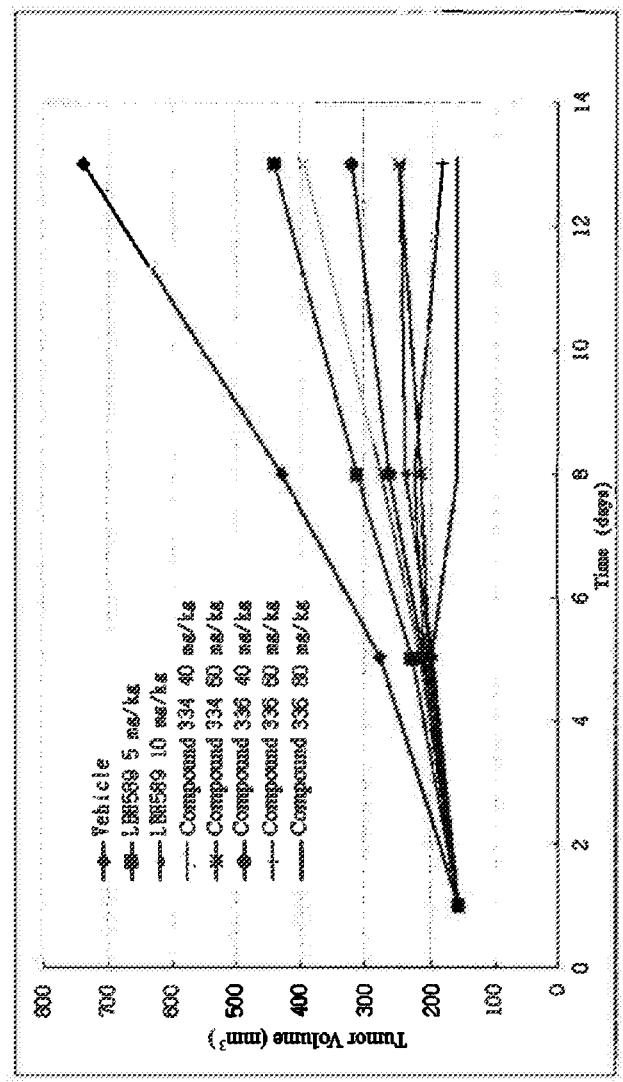

The present invention provides the following (1) to (12):

(1) Hydroxamate derivatives represented by the following formula I, isomers thereof, pharmaceutically acceptable salts thereof, hydrates thereof, or solvates thereof

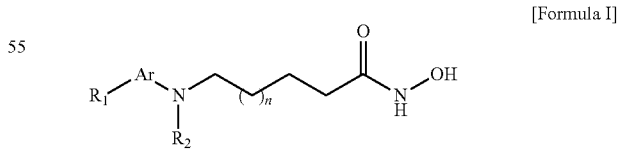

[Formula I]

wherein n, Ar, $R_1$ and $R_2$ are as defined above;

(2) The hydroxamate derivatives, isomers thereof, pharmaceutically acceptable salts thereof, hydrates thereof, or solvates thereof according to (1), wherein $R_1$ in formula I is an indole or indazole group which is unsubstituted or substituted with one or more substituents selected from the group consisting of $C_{1-6}$ alkyl, formyl, amino, nitro, thiomethyl, hydroxy, $C_{1-6}$ alkoxy, nitrile, carboxy, halogen, trifluoromethyl, —O—$CF_3$, —C(O)—$R_5$, —S($O_2$)—$R_5$ and

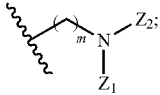

(3) The hydroxamate derivatives, isomers thereof, pharmaceutically acceptable salts thereof, hydrates thereof or solvates thereof according to (2), wherein Ar is a phenyl group which is unsubstituted or substituted with one or more substituents selected from the group consisting of $C_{1-6}$ alkyl, amino, nitro, thiomethyl, hydroxyl, nitrile, carboxyl, $C_{1-4}$ alkyloxyl, aryl $C_{1-4}$ alkyloxy, halogen, trifluoromethyl, —O—$CF_3$, phenyl and phenoxy groups;

(4) The hydroxamate derivatives, isomers thereof, pharmaceutically acceptable salts thereof, hydrates thereof or solvates thereof according to (3), wherein n is 3, Ar is an unsubstituted phenyl group, $R_1$ is an indole or indazole group which is substituted with hydrogen or one or more $C_{1-6}$ alkyl groups, and $R_2$ is hydrogen, —C(O)—$R_5$ or —S($O_2$)—$R_5$, in which $R_5$ is

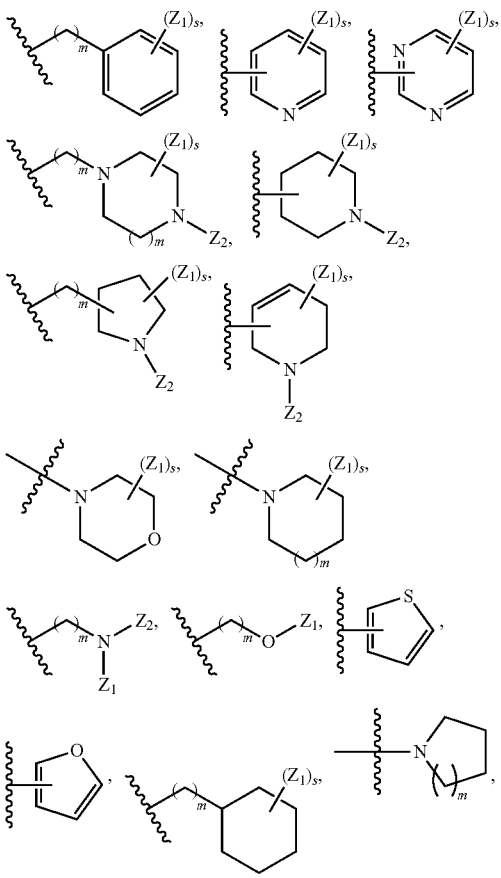

$Z_1$ and $Z_2$ are each independently hydrogen, $C_{1-6}$ alkyl, amino, —O—$C_{1-4}$ alkyl, —S($O_2$)$C_{1-4}$ alkyl, —C(O)$C_{1-4}$ alkyl, —S—$C_{1-4}$ alkyl, halogen, trifluoromethyl, —O—$CF_3$, phenyl, —O-phenyl, —O—$C_{1-4}$ alkylaryl,

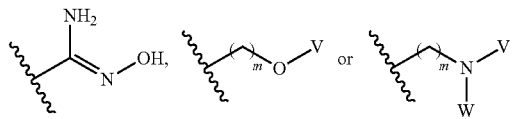

V and W are each independently hydrogen or $C_{1-6}$ alkyl,
Each s is independently an integer of 0, 1, 2, 3, 4 or 5, and
Each m is independently an integer of 0, 1, 2 or 3;

(5) The hydroxamate derivatives, isomers thereof, pharmaceutically acceptable salts thereof, hydrates thereof or solvates thereof according to (4), wherein n is 3, Ar is an unsubstituted phenyl group, $R_1$ is an indole or indazole group which is substituted with hydrogen or one or more $C_{1-6}$ alkyl groups, and $R_2$ is hydrogen, —C(O)—$R_5$ or —S($O_2$)—$R_5$, in which $R_5$ is

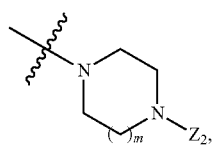

in which $Z_2$ is hydrogen or $C_{1-6}$ alkyl, and m is an integer of 0, 1, 2 or 3.

The hydroxamate derivatives of formula I may contain one or more asymmetric carbon atoms, and thus may exist as mixtures of two or more stereoisomers.

Such steroisomers, for example, a stereoisomer mixture of each of the hydroxamate derivatives of formula I or pharmaceutically acceptable appropriate salts thereof can be separated by a conventional resolution technique such as fractional crystallization, column chromatography, or HPLC. The enantiomer of each of the compounds of formula I can be separated by HPLC separation of a corresponding racemate using a chiral support. Alternatively, a mixture formed by allowing the corresponding racemate to react with an appropriate optically active acid or base can be separated by fractional crystallization or column chromatography. All isomers are included in the scope of the present invention.

The hydroxamate derivatives of formula I according to the present invention are generally used in the form of pharmaceutically acceptable salts. Pharmaceutically acceptable salts include appropriate pharmaceutically acceptable base-addition or acid-addition salts, for example, metal salts such as alkali metal salts or alkaline earth metal salts, ammonium salts, organic amine salts, amino acid salts, sulfonates, etc. Acid addition salts include inorganic acid salts, such as hydrochloride, sulfate or phosphate, and organic acid salts, such as alkyl sulfonate, aryl sulfonate, acetate, malate, fumarate, tartrate, citrate or lactate. Examples of metal salts include alkali metal salts such as lithium salt, sodium salt or potassium salt, and examples of alkaline earth metal salts include magnesium salt, calcium salt, aluminum salt and zinc salt. Examples of ammonium salt include ammonium salt and tetramethylammonium salt. Examples of organic amine salts include morpholine or piperidine salt. Examples of amino acid salts include glycine, phenylalanine, glutamic acid and lysine salts. Examples of sulfonates include mesylate, tosylate, and benzene sulfonate.

(6) Preferred examples of the hydroxamate derivatives of formula I according to the present invention are as follows:
7-(4-(1H-indol-5-yl)phenylamino)-N-hydroxyheptanamide;

N-hydroxy-7-(4-(1-methyl-1H-indol-5-yl)phenylamino)hydroxyheptanamide;
7-(3-(1H-indol-6-yl)phenylamino)-N-hydroxyheptanamide;
7-(4-(1H-indol-6-yl)phenylamino)-N-hydroxyheptanamide;
7-(3-(1H-indol-5-yl)phenylamino)-N-hydroxyheptanamide;
7-(4-(1H-indol-4-yl)phenylamino)-N-hydroxyheptanamide;
7-(2-(1H-indol-5-yl)phenylamino)-N-hydroxyheptanamide;
7-(5-(1H-indol-6-yl)pyridin-2-ylamino)-N-hydroxyheptanamide;
7-(6-(1H-indol-6-yl)pyridin-3-ylamino)-N-hydroxyheptanamide;
7-(3-(1H-indol-7-yl)phenylamino)-N-hydroxyheptanamide;
7-(5-(1H-indol-6-yl)pyrimidin-2-ylamino)-N-hydroxyheptanamide;
7-(4-(1H-indol-7-yl)phenylamino)-N-hydroxyheptanamide;
N-(4-(1H-indol-6-yl)phenyl)-N-(7-(hydroxyamino)-7-oxoheptyl)-4-methoxybenzamide;
N-(4-(1H-indol-6-yl)phenyl)-N-(7-(hydroxyamino)-7-oxoheptyl)nicotinamide;
7-(N-(4-(1H-indol-6-yl)phenyl)-2-phenylacetamido)-N-hydroxyheptanamide;
phenyl 4-(1H-indol-6-yl)phenyl(7-(hydroxyamino)-7-oxoheptyl)carbamate;
benzyl 4-(1H-indol-6-yl)phenyl(7-(hydroxyamino)-7-oxoheptyl)carbamate;
7-((4-(1H-indol-6-yl)phenyl)(2-hydroxyethyl)amino)-N-hydroxyheptanamide;
N-hydroxy-7-(4-(1-(phenylsulfonyl)-1H-indol-2-yl)phenylamino)heptanamide;
7-(N-(4-(1H-indol-6-yl)phenyl)thiophene-2-sulfonamido)-N-hydroxyheptanamide;
N-(4-(1H-indol-6-yl)phenyl)-N-(7-(hydroxyamino)-7-oxoheptyl)furan-2-carboxamide;
7-(N-(4-(1H-indol-6-yl)phenyl)-4-methoxyphenylsulfonamido)-N-hydroxyheptanamide;
N-(4-(1H-indol-5-yl)phenyl)-N-(7-(hydroxyamino)-7-oxoheptyl)-4-methoxybenzamide;
N-(4-(1H-indol-6-yl)phenyl)-N-(7-(hydroxyamino)-7-oxoheptyl)-4-methylbenzamide;
7-(N-(4-(1H-indol-6-yl)phenyl)phenylsulfonamido)-N-hydroxyheptanamide;
N-(4-(1H-indol-6-yl)phenyl)-N-(7-(hydroxyamino)-7-oxoheptyl)picolinamide;
N-(4-(1H-indol-6-yl)phenyl)-N-(7-(hydroxyamino)-7-oxoheptyl)-3-methoxybenzamide;
N-(4-(1H-indol-6-yl)phenyl)-N-(7-(hydroxyamino)-7-oxoheptyl)-3,4,5-trimethylbenzamide;
N-(4-(1H-indol-6-yl)phenyl)-4-(dimethylamino)-N-(7-(hydroxyamino)-7-oxoheptyl)benzamide;
7-(N-(4-(1H-indol-6-yl)phenyl)-2-aminoacetamido)-N-hydroxyheptanamide;
N-(4-(1H-indol-6-yl)phenyl)-6-chloro-N-(7-(hydroxyamino)-7-oxoheptyl)nicotinamide;
N-(4-(1H-indol-6-yl)phenyl)-N-(7-(hydroxyamino)-7-oxoheptyl)isonicotinamide;
(Z)-N-(4-(1H-indol-6-yl)phenyl)-N-(7-(hydroxyamino)-7-oxoheptyl)-4-(N'-hydroxycarbamimidoyl)benzamide;
N-(4-(1H-indol-6-yl)phenyl)-2,6-difluoro-N-(7-(hydroxyamino)-7-oxoheptyl)benzamide;
N-(4-(1H-indol-6-yl)phenyl)-4-fluoro-N-(7-(hydroxyamino)-7-oxoheptyl)benzamide;
N-(4-(1H-indol-6-yl)phenyl)-N-(7-(hydroxyamino)-7-oxoheptyl)-6-(trifluoromethyl)nicotinamide;
6-(4-(1H-indol-6-yl)phenylamino)-N-hydroxyhexanamide;
8-(4-(1H-indol-6-yl)phenylamino)-N-hydroxyoctanamide;
N-(4-(1H-indol-6-yl)phenyl)-4-ethoxy-N-(7-(hydroxyamino)-7-oxoheptyl)benzamide;
7-((4-(1H-indol-6-yl)phenyl)(benzyl)amino)-N-hydroxyheptanamide;
N-(4-(1H-indol-6-yl)phenyl)-2,4,6-trifluoro-N-(7-(hydroxyamino)-7-oxoheptyl)benzamide;
N-(4-(1H-indol-6-yl)phenyl)-4-amino-N-(7-(hydroxyamino)-7-oxoheptyl)benzamide;
N-(4-(1H-indol-6-yl)phenyl)-N-(7-(hydroxyamino)-7-oxoheptyl)piperidin-1-carboxamide;
N-(4-(1H-indol-6-yl)phenyl)-N-(7-(hydroxyamino)-7-oxoheptyl)-4-methoxy-3-(trifluoromethyl)benzamide;
N-(4-(1H-indol-6-yl)phenyl)-N-(7-(hydroxyamino)-7-oxoheptyl)-4-(trifluoromethyl)benzamide;
N-(4-(1H-indol-6-yl)phenyl)-N-(7-(hydroxyamino)-7-oxoheptyl)-3,4-dimethoxybenzamide;
7-(N-(4-(1H-indol-6-yl)phenyl)-3,4-dimethoxyphenylsulfonamido)-N-hydroxyheptanamide;
7-(N-(4-(1H-indol-6-yl)phenyl)-4-(methylsulfonyl)phenylsulfonamido)-N-hydroxyheptanamide;
7-(4-(1H-indol-6-yl)-3-(trifluoromethyl)phenylamino)-N-hydroxyheptanamide;
N-(4-(1H-indol-6-yl)-3-(trifluoromethyl)phenyl)-N-(7-(hydroxyamino)-7-oxoheptyl)nicotinamide;
7-(N-(4-(1H-indol-6-yl)phenyl)naphthalene-2-sulfonamido)-N-hydroxyheptanamide;
N-(4-(1H-indol-6-yl)-3-methylphenyl)-N-(7-(hydroxyamino)-7-oxoheptyl)-4-methoxybenzamide;
7-(1-(4-(1H-indol-6-yl)phenyl)-3-(4-methoxyphenyl)ureido)-N-hydroxyheptanamide;
7-(1-(4-(1H-indol-6-yl)phenyl)-3-(3-methoxyphenyl)ureido)-N-hydroxyheptanamide;
7-(N-(4-(1H-indol-6-yl)phenyl)acetamido)-N-hydroxyheptanamide;
methyl 4-(1H-indol-6-yl)phenyl(7-(hydroxyamino)-7-oxoheptyl)carbamate;
7-(1-(4-(1H-indol-6-yl)phenyl)-3-(2-methoxyphenyl)ureido)-N-hydroxyheptanamide;
7-(1-(4-(1H-indol-6-yl)phenyl)-3-(3,5-dimethoxyphenyl)ureido)-N-hydroxyheptanamide;
7-(N-(4-(1H-indol-6-yl)phenyl)-5-amino-2-methoxyphenylsulfonamido)-N-hydroxyheptanamide;
7-(1-(4-(1H-indol-6-yl)phenyl)-3-(thiophen-2-yl)ureido)-N-hydroxyheptanamide;
7-(N-(4-(1H-indol-6-yl)phenyl)pyridine-3-sulfonamido)-N-hydroxyheptanamide;
7-(N-(4-(1H-indol-6-yl)phenyl)methylsulfonamido)-N-hydroxyheptanamide;
7-(N-(4-(1H-indol-6-yl)phenyl)-2-(dimethylamino)acetamido)-N-hydroxyheptanamide;
4-methoxyphenyl 4-(1H-indol-6-yl)phenyl(7-(hydroxyamino)-7-oxoheptyl)carbamate;
ethyl 4-(1H-indol-6-yl)phenyl(7-(hydroxyamino)-7-oxoheptyl)carbamate;
7-(1-(4-(1H-indol-6-yl)phenyl)-3,3-dimethylureido)-N-hydroxyheptanamide;
2-methoxyethyl 4-(1H-indol-6-yl)phenyl(7-(hydroxyamino)-7-oxoheptyl)carbamate;
N-(7-(hydroxyamino)-7-oxoheptyl)-N-(4-(1-methyl-1H-indazol-6-yl)phenyl)nicotinamide;
N-hydroxy-7-(4-(1-methyl-1H-indazol-6-yl)phenylamino)heptanamide;
7-(N-(4-(1H-indol-6-yl)phenyl)propionamido)-N-hydroxyheptanamide;
N-(4-(1H-indol-6-yl)phenyl)-N-(7-(hydroxyamino)-7-oxoheptyl)-1-methyl-1,2,5,6-tetrahydropyridine-3-carboxamide;
7-(1-(4-(1H-indol-6-yl)phenyl)-3-(pyridin-3-yl)ureido)-N-hydroxyheptanamide;

7-(1-(4-(1H-indol-6-yl)phenyl)-3-methylureido)-N-hydroxyheptanamide;
7-(N-(4-(1H-indol-6-yl)phenyl)ethylsulfonamido)-N-hydroxyheptanamide;
7-((4-(1H-indol-6-yl)phenyl)(N,N-dimethylsulfamoyl)amino)-N-hydroxyheptanamide;
N-(4-(1H-indol-6-yl)phenyl)-N-(7-(hydroxyamino)-7-oxoheptyl)cyclohexanecarboxamide;
N-(4-(1H-indol-6-yl)phenyl)-N-(7-(hydroxyamino)-7-oxoheptyl)cyclopropanecarboxamide;
7-(N-(4-(1H-indol-6-yl)phenyl)-2-morpholinoacetamido)-N-hydroxyheptanamide;
(S)—N-(4-(1H-indol-6-yl)phenyl)-N-(7-(hydroxyamino)-7-oxoheptyl)pyrrolidine-2-carboxamide;
7-(1-(4-(1H-indol-6-yl)phenyl)-3-isopropylureido)-N-hydroxyheptanamide;
7-(1-(4-(1H-indol-6-yl)phenyl)-3-isobutylureido)-N-hydroxyheptanamide;
N-hydroxy-7-(N-(4-(1-methyl-1H-indazol-6-yl)phenyl)methylsulfonamido)heptanamide;
7-((4-(1H-indol-6-yl)phenyl)(propyl)amino)-N-hydroxyheptanamide;
7-(N-(4-(1H-indol-6-yl)phenyl)-2-(4-methylpiperazin-1-yl)acetamido)-N-hydroxyheptanamide;
7-(1-(4-(1H-indol-6-yl)phenyl)-3-butylureido)-N-hydroxyheptanamide;
7-(1-(4-(1H-indol-6-yl)phenyl)-3-(4-methylpentyl)ureido)-N-hydroxyheptanamide;
7-(1-(4-(1H-indol-6-yl)phenyl)-3-(3-(dimethylamino)propyl)ureido)-N-hydroxyheptanamide;
7-(1-(4-(1H-indol-6-yl)phenyl)-3-(cyclohexylmethyl)ureido)-N-hydroxyheptanamide;
7-(N-(4-(1H-indol-6-yl)phenyl)pentanamido)-N-hydroxyheptanamide;
7-(N-(4-(1H-indol-6-yl)phenyl)isobutyramido)-N-hydroxyheptanamide;
7-(N-(4-(1H-indol-6-yl)phenyl)-2-(4-(2-methoxyethyl)piperazin-1-yl)acetamido)-N-hydroxyheptanamide;
7-(1-(4-(1H-indol-6-yl)phenyl)-3,3-diethylureido)-N-hydroxyheptanamide;
7-(1-(4-(1H-indol-6-yl)phenyl)-3-ethylureido)-N-hydroxyheptanamide;
N-hydroxy-7-(N-(4-(2-methyl-1H-indol-5-yl)phenyl)methylsulfonamido)heptanamide; isobutyl 4-(1H-indol-6-yl)phenyl(7-(hydroxyamino)-7-oxoheptyl)carbamate;
N-(4-(1H-indol-6-yl)phenyl)-N-(7-(hydroxyamino)-7-oxoheptyl)thiophene-2-carboxamide;
N-(7-(hydroxyamino)-7-oxoheptyl)-N-(4-(1-methyl-1H-indazol-6-yl)phenyl)picolinamide;
7-(N-(4-(1H-indol-5-yl)phenyl)methylsulfonamido)-N-hydroxyheptanamide;
N-(4-(1H-indol-6-yl)phenyl)-N-(7-(hydroxyamino)-7-oxoheptyl)-1-methylpiperidine-4-carboxamide;
N-(4-(1H-indol-5-yl)phenyl)-N-(7-(hydroxyamino)-7-oxoheptyl)picolinamide;
N-(4-(1H-indol-5-yl)phenyl)-N-(7-(hydroxyamino)-7-oxoheptyl)morpholine-4-carboxamide;
7-(N-(4-(1,2-dimethyl-1H-indol-5-yl)phenyl)methylsulfonamido)-N-hydroxyheptanamide;
N-(4-(1H-indol-6-yl)phenyl)-N-(7-(hydroxyamino)-7-oxoheptyl)-4-methylpiperazine-1-carboxamide;
N-hydroxy-7-(N-(4-(1-methyl-1H-indazol-6-yl)phenyl)ethylsulfonamido)heptanamide;
N-(4-(1H-indol-5-yl)phenyl)-N-(7-(hydroxyamino)-7-oxoheptyl)nicotinamide;
N-(7-(hydroxyamino)-7-oxoheptyl)-4-methyl-N-(4-(1-methyl-1H-indazol-6-yl)phenyl)piperazine-1-carboxamide;
N-(4-(1H-indol-5-yl)phenyl)-N-(7-(hydroxyamino)-7-oxoheptyl)-4-methylpiperazine-1-carboxamide;
7-(N-(4-(1H-indol-5-yl)phenyl)ethylsulfonamido)-N-hydroxyheptanamide;
N-(7-(hydroxyamino)-7-oxoheptyl)-N-(4-(1-methyl-1H-indazol-6-yl)phenyl)morpholine-4-carboxamide;
N-(4-(1H-indol-5-yl)phenyl)-N-(7-(hydroxyamino)-7-oxoheptyl)morpholine-4-carboxamide;
N-(4-(1H-indol-6-yl)phenyl)-N-(7-(hydroxyamino)-7-oxoheptyl)-2,6-dimethylmorpholine-4-carboxamide;
N-(7-(hydroxyamino)-7-oxoheptyl)-2,6-dimethyl-N-(4-(1-methyl-1H-indazol-6-yl)phenyl)morpholine-4-carboxamide;
N-(4-(1H-indol-5-yl)phenyl)-N-(7-(hydroxyamino)-7-oxoheptyl)-2,6-dimethylmorpholine-4-carboxamide;
N-hydroxy-7-(N-(4-(1-methyl-1H-indol-5-yl)phenyl)methylsulfonamido)heptanamide;
N-hydroxy-7-(N-(4-(1-methyl-1H-indol-6-yl)phenyl)methylsulfonamido)heptanamide;
N-(4-(1H-indol-6-yl)phenyl)-N-(7-(hydroxyamino)-7-oxoheptyl)-4-isopropylpiperazine-1-carboxamide;
N-(4-(1H-indol-6-yl)phenyl)-N-(7-(hydroxyamino)-7-oxoheptyl)pyrrolidine-1-carboxamide;
N-(4-(1H-indol-5-yl)phenyl)-N-(7-(hydroxyamino)-7-oxoheptyl)isonicotinamide;
7-(N-(6-(1H-indol-6-yl)pyridin-3-yl)methylsulfonamido)-N-hydroxyheptanamide;
N-hydroxy-7-(N-(6-(1-methyl-1H-indazol-6-yl)pyridin-3-yl)methylsulfonamido)heptanamide;
7-(N-(6-(1H-indol-5-yl)pyridin-3-yl)methylsulfonamido)-N-hydroxyheptanamide;
N-(4-(1H-indol-6-yl)phenyl)-4-acetyl-N-(7-(hydroxyamino)-7-oxoheptyl)piperazine-1-carboxamide;
N-(4-(1H-indol-6-yl)phenyl)-N-(7-(hydroxyamino)-7-oxoheptyl)-4-methyl-1,4-diazepane-1-carboxamide;
N-(7-(hydroxyamino)-7-oxoheptyl)-4-methyl-N-(4-(1-methyl-1H-indol-6-yl)phenyl)piperazine-1-carboxamide;
7-(N-(4-(1H-indol-2-yl)phenyl)methylsulfonamido)-N-hydroxyheptanamide;
tert-butyl 2-(4-(N-(7-(hydroxyamino)-7-oxoheptyl)methylsulfonamido)phenyl)-1H-indole-1-carboxylate;
N-(7-(hydroxyamino)-7-oxoheptyl)-4-methyl-N-(4-(2-methyl-1H-indol-5-yl)phenyl)piperazine-1-carboxamide;
N-(4-(1H-indol-6-yl)phenyl)-4-benzyl-N-(7-(hydroxyamino)-7-oxoheptyl)piperazine-1-carboxamide;
4-ethyl-N-(7-(hydroxyamino)-7-oxoheptyl)-N-(4-(1-methyl-1H-indazole-6-yl)phenyl)piperazine-1-carboxamide;
7-(N-(4-(5-bromo-1H-indol-2-yl)phenyl)methylsulfonamido)-N-hydroxyheptanamide;
tert-butyl 5-bromo-2-(4-(N-(7-(hydroxyamino)-7-oxoheptyl)methylsulfonamido)phenyl)-1H-indazole-1-carboxylate;
N-(4-(1H-indol-6-yl)phenyl)-4-ethyl-N-(7-(hydroxyamino)-7-oxoheptyl)piperazine-1-carboxamide;
N-(4-(1H-indol-5-yl)phenyl)-4-ethyl-N-(7-(hydroxyamino)-7-oxoheptyl)piperazine-1-carboxamide;
N-(7-(hydroxyamino)-7-oxoheptyl)-4-methyl-N-(4-(1-methyl-1H-indol-5-yl)phenyl)piperazine-1-carboxamide;
N-hydroxy-7-(4-methyl-N-(4-(1-methyl-1H-indazol-6-yl)phenyl)piperazine-1-sulfonamide)heptanamide;
N-(4-(1H-indol-6-yl)phenyl)-N-(7-(hydroxyamino)-7-oxoheptyl)-4-(2-methoxyphenyl)piperazine-1-carboxamide;
N-(4-(1H-indol-6-yl)phenyl)-N-(7-(hydroxyamino)-7-oxoheptyl)-4-(3-methoxyphenyl)piperazine-1-carboxamide;
N-(4-(3H-benzo[d]imidazol-5-yl)phenyl)-N-(7-(hydroxyamino)-7-oxoheptyl)-4-methylpiperazine-1-carboxamide;

N-(4-(1H-indol-6-yl)phenyl)-N-(7-(hydroxyamino)-7-oxo-heptyl)-4-(2-hydroxyethyl)piperazine-1-carboxamide;
7-(3-(2-(dimethylamino)ethyl)-1-(4-(1-methyl-1H-indazol-6-yl)phenyl)ureido)-N-hydroxyheptanamide;
N-hydroxy-7-(1-(4-(1-methyl-1H-indazol-6-yl)phenyl)-3-(2-(1-methylpyrrolidin-2-yl)ethyl)ureido)heptanamide;
N-(4-(1H-indol-6-yl)phenyl)-4-butyl-N-(7-(hydroxyamino)-7-oxoheptyl)piperazine-1-carboxamide;
N-(7-(hydroxyamino)-7-oxoheptyl)-4-methyl-N-(4-(1-methyl-1H-indazol-5-yl)phenyl)piperazine-1-carboxamide;
4-ethyl-N-(7-(hydroxyamino)-7-oxoheptyl)-N-(4-(1-methyl-1H-indazol-5-yl)phenyl)piperazine-1-carboxamide;
N-(4-(1H-indol-6-yl)phenyl)-4-(2-(dimethylamino)ethyl)-N-(7-(hydroxyamino)-7-oxoheptyl)piperazine-1-carboxamide;
7-(3-((1-ethylpyrrolidin-2-yl)methyl)-1-(4-(1-methyl-1H-indazol-6-yl)phenyl)ureido)-N-hydroxyheptanamide;
7-(N-(4-(1H-indol-6-yl)phenyl)-4-methylpiperazine-1-sulfonamido)-N-hydroxyheptanamide;
7-(N-(4-(1H-indol-5-yl)phenyl)-4-methylpiperazine-1-sulfonamido)-N-hydroxyheptanamide;
N-(4-(1H-indol-6-yl)phenyl)-N-(7-(hydroxyamino)-7-oxoheptyl)-4-methylpiperazine-1-carboxamide;
7-(N-(4-(1H-indol-6-yl)phenyl)-4-methylpiperazine-1-carbothioamido)-N-hydroxyheptanamide;
7-(N-(4-(1H-indol-5-yl)phenyl)-4-methylpiperazine-1-carbothioamido)-N-hydroxyheptanamide; or
N-hydroxy-7-(4-methyl-N-(4-(1-methyl-1H-indazol-5-yl)phenyl)piperazine-1-carbothioamido)heptaneamide.

(7) Particularly preferred examples of the hydroxamate derivatives of formula I according to the present invention are as follows:
N-(7-(hydroxyamino)-7-oxoheptyl)-4-methyl-N-(4-(1-methyl-1H-indazol-6-yl)phenyl)piperazine-1-carboxamide;
N-(7-(hydroxyamino)-7-oxoheptyl)-4-methyl-N-(4-(2-methyl-1H-indol-5-yl)phenyl)piperazine-1-carboxamide;
4-ethyl-N-(7-(hydroxyamino)-7-oxoheptyl)-N-(4-(1-methyl-1H-indazol-6-yl)phenyl)piperazine-1-carboxamide; or
N-hydroxy-7-(4-methyl-N-(4-(1-methyl-1H-indazol-6-yl)phenyl)piperazine-1-sulfonamido)heptanamide.

(8) Use of hydroxamate derivatives of formula I, isomers thereof, pharmaceutically acceptable salts thereof, hydrates thereof or solvates thereof according to any one of (1) to (6) for preparing pharmaceutical compositions.

(9) Pharmaceutical compositions comprising hydroxamate derivatives of formula I, isomers thereof, pharmaceutically acceptable salts thereof, hydrates thereof or solvates thereof according to any one of (1) to (6) together with pharmaceutically acceptable carriers.

(10) The pharmaceutical compositions according to (9), wherein the compositions are used for prevention or treatment of a disease associated with histone deacetylase activity.

(11) The pharmaceutical compositions of (10), wherein the disease associated with histone deacetylase activity is malignant tumor, viral and bacterial infection, vascular restenosis, inflammatory disease, autoimmune disease or psoriasis.

(12) A method for prevention or treatment of disease, the method comprising administering the pharmaceutical compositions according to any one of (9) to (11).

(13) A method for preparing hydroxamate derivatives, the method comprising the steps of allowing a compound of the following formula II to react with bromoaniline in the presence of an inorganic salt so as to prepare a compound of the following formula III; allowing the compound of formula III to react with 4-nitrophenylchloroformate so as to prepare a compound of the following formula VI; subjecting the compound of formula VI to the Suzuki reaction with boronic acid in the presence of palladium to prepare a compound of the following formula VII; allowing the compound of formula VII to react with an amine in the presence of an inorganic salt so as to prepare a compound of the following formula VIII; and treating the compound of formula VIII with a hydroxide salt, thus preparing hydroxamate derivatives of the following formula I-2:

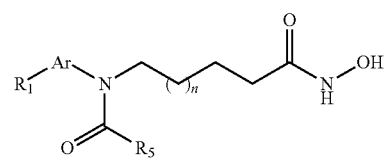
[Formula I-2]

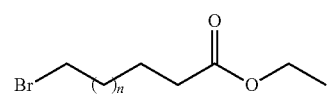
[Formula II]

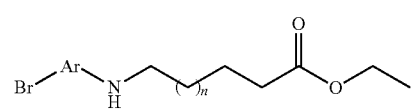
[Formula III]

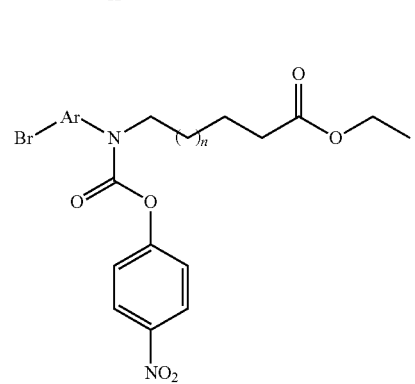
[Formula VI]

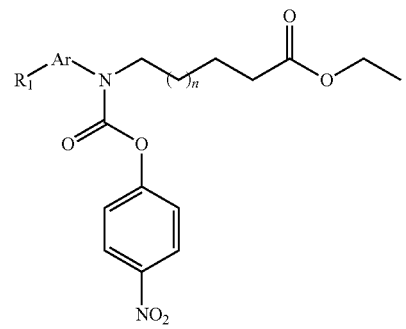
[Formula VII]

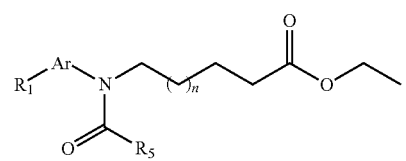
[Formula VIII]

wherein n is 3, Ar is phenyl, $R_1$ is 1H-indol-5-yl, 1-methyl-1H-indazol-6-yl, 1-methyl-1H-indazol-5-yl, 3H-benzo[d]imidazol-5-yl, or 1H-indol-6-yl, and $R_5$ is 1-methylpiperazine, morpholine, 2,6-dimethylmorpholine, 1-ethylpiperazine, N,N-dimethylethane-1,2-diamine, 2-(1-methylpyrrolidin-2-yl)ethanamine, (1-ethylpyrrolidin-2-yl)methanamine, 4-methoxy benzenamine, 3-methoxy benzenamine, 2-methoxy benzenamine, 3,5-dimethoxy benzenamine, thiophen-2-amine, dimethylamine, pyridine-3-amine, methylamine, isopropylamine, isobutylamine, butylamine, 4-methylpentylamine, N,N-dimethylpropane-1,3-diamine, cyclohexylmethylamine, diethylamine, ethylamine, 1-isopropylpiperazine, pyrrolidine, 1-(piperazin-1-yl)ethanone, 1-methylhomopiperazine, 1-benzylpiperazine, 1-(2-methoxyphenyl)piperazine, 1-(3-methoxyphenyl)piperazine, 2-(piperazin-1-yl)ethanol, 1-butylpiperazine, N,N-dimethyl-2-(piperazin-1-yl)ethanamine, or 4-methylpiperidine.

The hydroxamate derivatives of formula I of the present invention can be prepared according to the following reaction scheme 1:

Compound 185. $R_2=$

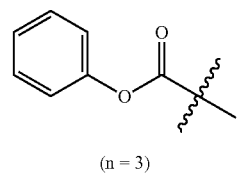

(n = 3)

Compound 189. $R_2=$

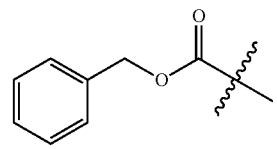

(n = 3)

[Reaction Scheme 1]

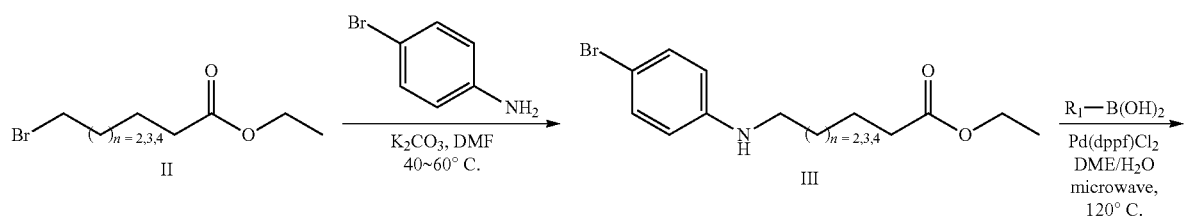

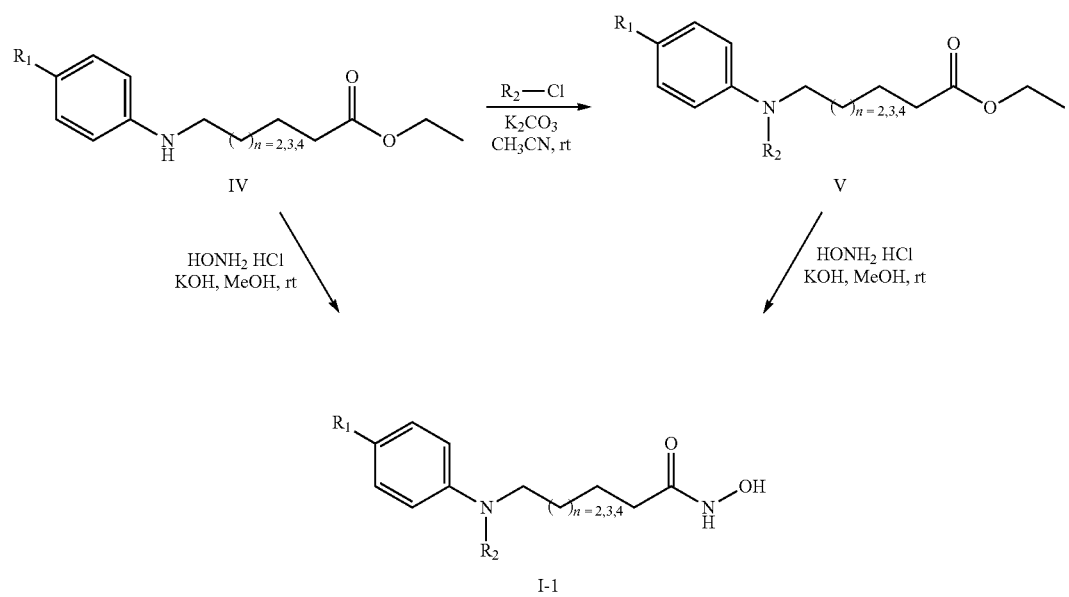

$R_1$=1H-indol-6-yl

Compound 167. $R_2$=hydrogen (n=3)
Compound 180. $R_2$=4-methoxybenzoyl (n=3)
Compound 181. $R_2$=nicotinoyl (n=3)
Compound 184. $R_2$=2-phenylacetyl (n=3)

Compound 190. $R_2$=hydroxyethyl (n=3)
Compound 203. $R_2$=thiophene-2-sulfonyl (n=3)
Compound 204. $R_2$=furan-2-carbonyl (n=3)
Compound 207. $R_2$=4-methoxybenzene sulfonyl (n=3)
Compound 209. $R_2$=4-methylbenzoyl (n=3)

Compound 210. $R_2$=benzenesulfonyl (n=3)
Compound 211. $R_2$=picolinoyl (n=3)
Compound 212. $R_2$=3-methoxybenzoyl (n=3)
Compound 214. $R_2$=3,4,5-trimethoxybenzoyl (n=3)
Compound 215. $R_2$=4-dimethylaminobenzoyl (n=3)
Compound 218. $R_2$=2-aminoacetyl (n=3)
Compound 221. $R_2$=6-chloronicotinoyl (n=3)
Compound 222. $R_2$=isonicotinoyl (n=3)
Compound 228. $R_2$=

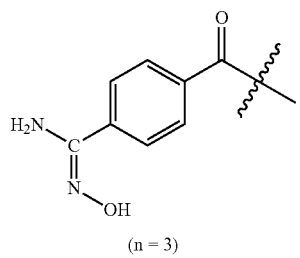 [SMILES: *C(=O)c1ccc(/C(N)=N\O)cc1]

Compound 229. $R_2$=2,6-difluorobenzoyl (n=3)
Compound 230. $R_2$=4-fluorobenzoyl (n=3)
Compound 231. $R_2$=6-(trifluoromethyl)nicotinoyl (n=3)
Compound 234. $R_2$=hydrogen (n=2)
$R_1$=1H-indol-6-yl
Compound 258. $R_2$=

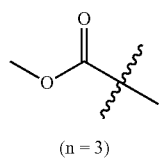 [SMILES: *C(=O)OC]

Compound 261. $R_2$=5-amino-2-methoxybenzene-1-sulfonyl (n=3)
Compound 263. $R_2$=pyridine-3-sulfonyl (n=3)
Compound 264. $R_2$=methanesulfonyl (n=3)
Compound 265. $R_2$=2-(dimethylamino)acetyl (n=3)
Compound 266. $R_2$=

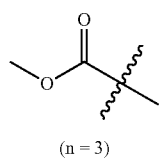 [SMILES: *C(=O)OC]

Compound 267. $R_2$=

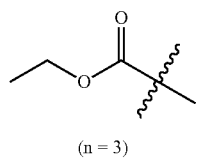 [SMILES: *C(=O)OCC]

Compound 269. $R_2$=

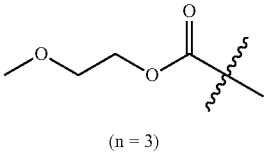 [SMILES: *C(=O)OCCOC]

Compound 272. $R_2$=propionyl (n=3)
Compound 273. $R_2$=1-methyl-1,2,5,6-tetrahydropyridine-3-carbonyl (n=3)
Compound 276. $R_2$=ethanesulfonyl (n=3)
Compound 277. $R_2$=dimethylsulfamoyl (n=3)
Compound 278. $R_2$=cyclohexanecarbonyl (n=3)
Compound 279. $R_2$=cyclopropanecarbonyl (n=3)
Compound 280. $R_2$=2-morpholinoacetyl (n=3)
Compound 281. $R_2$=(S)-pyrrolidine-2-carbonyl (n=3)
Compound 285. $R_2$=propane (n=3)
Compound 286. $R_2$=2-(4-methylpiperazin-1-yl)acetyl (n=3)
Compound 291. $R_2$=pentanoyl (n=3)
Compound 292. $R_2$=isobutyryl (n=3)
Compound 293. $R_2$=2-(4-(2-methoxyethyl)piperazin-1-yl)acetyl (n=3)
Compound 299. $R_2$=

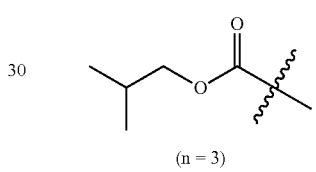

Compound 300. $R_2$=thiophene-2-carbonyl (n=3)
Compound 304. $R_2$=1-methylpiperidine-4-carbonyl (n=3)
Compound 354. $R_2$=4-methylpiperazine-1-sulfonyl (n=3)
$R_1$=1H-indol-6-yl
Compound 235. $R_2$=hydrogen (n=4)
Compound 236. $R_2$=4-methoxybenzoyl (n=3)
Compound 237. $R_2$=benzyl (n=3)
Compound 239. $R_2$=2,4,6-trifluorobenzoyl (n=3)
Compound 242. $R_2$=4-aminobenzoyl (n=3)
Compound 243. $R_2$=piperidine-1-carbonyl (n=3)
Compound 244. $R_2$=4-methoxy-3-(trifluoromethyl)benzoyl (n=3)
Compound 245. $R_2$=4-(trifluoromethyl)benzoyl (n=3)
Compound 246. $R_2$=3,4-dimethoxybenzoyl (n=3)
Compound 249. $R_2$=3,4-dimethoxybenzene-1-sulfonyl (n=3)
Compound 250. $R_2$=4-(methanesulfonyl)benzene-1-sulfonyl (n=3)
Compound 253. $R_2$=naphthalene-2-sulfonyl (n=3)
Compound 257. $R_2$=acetyl (n=3)
$R_1$=1H-methyl-1H-indol-5-yl
Compound 158. $R_2$=hydrogen (n=3)
$R_1$=1H-methyl-1H-indol-5-yl
$R_1$=1H-indol-5-yl
Compound 150. $R_2$=hydrogen (n=3)
Compound 208. $R_2$=4-methoxybenzoyl (n=3)
Compound 303. $R_2$=methanesulfonyl (n=3)
Compound 305. $R_2$=picolinoyl (n=3)
Compound 311. $R_2$=nicotinoyl (n=3)
Compound 314. $R_2$=ethanesulfonyl (n=3)
Compound 325. $R_2$=isonicotinoyl (n=3)
Compound 355. $R_2$=4-methylpiperazine-1-sulfonyl (n=3)
$R_1$=1-methyl-1H-indazol-6-yl Compound 270. $R_2$=nicotinoyl (n=3)
Compound 271. $R_2$=hydrogen (n=3)
Compound 284. $R_2$=methanesulfonyl (n=3)
Compound 302. $R_2$=picolinoyl (n=3)
Compound 310. $R_2$=ethanesulfonyl (n=3)
Compound 342. $R_2$=4-methylpiperazine-1-sulfonyl (n=3)

As shown reaction scheme 1 above, potassium carbonate ($K_2CO_3$) and dimethylformamide (DMF) are added to the compound of formula II that is the starting material, and then a bromoaniline compound is added dropwise thereto, after which the mixture is allowed to react at a temperature of 40~60° C., thus synthesizing the compound of formula III. As shown in reaction scheme 1, the obtained compound of formula III is subjected to the Suzuki reaction (Moths, G. A., et al., Tetrahedron Lett., 2001, 42, 2093) using boronic acid, thus preparing the compound of formula W. Where $R_2$ is H, potassium hydroxide (KOH), methanol and hydroxylamine hydrochloride ($HONH_2$ HCl) are sequentially added dropwise to the compound of formula IV, and then allowed to react at mom temperature, thus synthesizing desired final compounds 150, 167, 234, 235 and 271.

Where $R_2$ is not H, acid chloride is added to the compound of formula IV, and potassium carbonate ($K_2CO_3$) and acetonitrile ($CH_3CN$) are added dropwise thereto, after which the mixture is acylated at mom temperature, thus preparing an amide derivative of formula V. To the amide derivative, potassium hydroxide (KOH), methanol and hydroxylamine hydrochloride ($HONH_2HCl$) are sequentially added dropwise, and the mixture is allowed to react at mom temperature, thus preparing desired final compounds 158, 180, 181, 184, 185, 189, 190, 203, 204, 207, 208, 209, 210, 211, 212, 214, 215, 218, 221, 222, 228, 229, 230, 231, 236, 237, 239, 242, 243, 244, 245, 246, 249, 250, 253, 257, 258, 261, 263, 264, 265, 266, 267, 269, 270, 272, 273, 276, 277, 278, 279, 280, 281, 284, 285, 286, 291, 292, 293, 299, 300, 302, 303, 304, 305, 310, 311, 314, 325, 342, 354 and 355.

Also, the hydroxamate derivatives of formula I can be prepared according to the following reaction scheme 2:

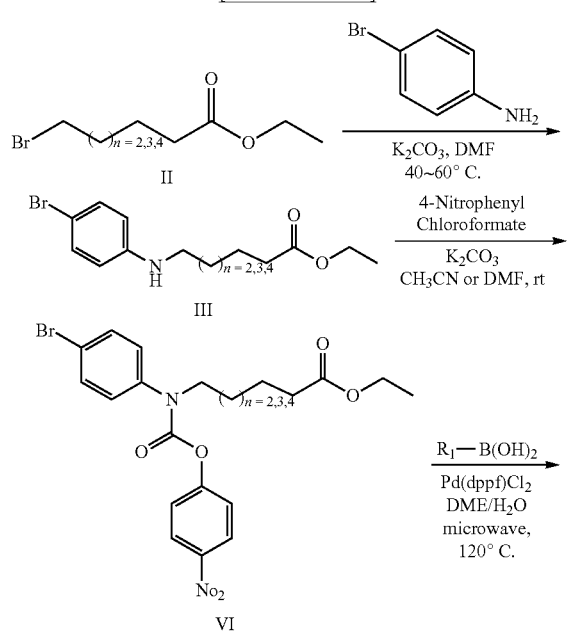

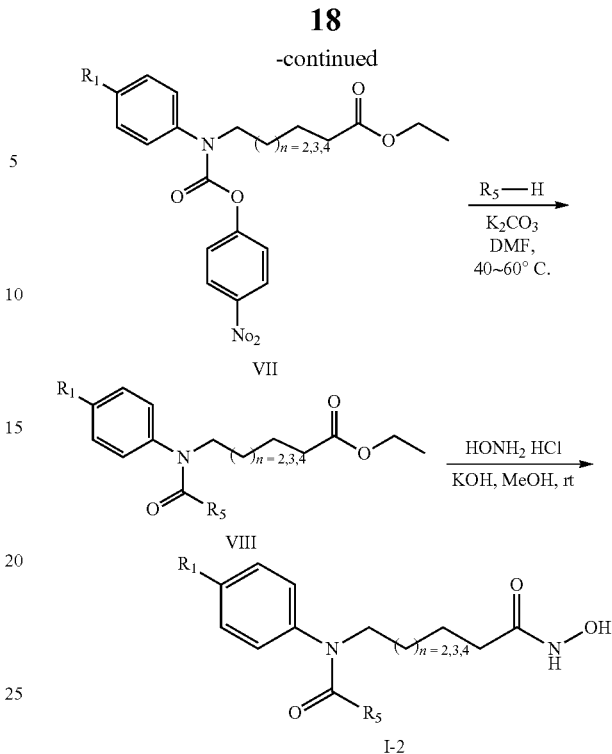

$R_1$=1H-indol-5-yl
Compound 313. $R_5$=1-methylpiperazine (n=3)
Compound 316. $R_5$=morpholine (n=3)
Compound 319. $R_5$=2,6-dimethylmorpholine (n=3)
Compound 340. $R_5$=1-ethylpiperazine (n=3)
$R_1$=1-methyl-1H-indazol-6-yl
Compound 312. $R_5$=1-methylpiperazine (n=3)
Compound 315. $R_5$=morpholine (n=3)
Compound 318. $R_5$=2,6-dimethylmorpholine (n=3)
Compound 336. $R_5$=1-ethylpiperazine (n=3)
Compound 347. $R_5$=N,N-dimethylethane-1,2-diamine (n=3)
Compound 348. $R_5$=2-(1-methylpyrrolidin-2-yl)ethanamine (n=3)
Compound 353. $R_5$=(1-ethylpyrrolidin-2-yl)methanamine (n=3)
$R_1$=1-methyl-1H-indazol-5-yl
Compound 350. $R_5$=1-methylpiperazine (n=3)
Compound 351. $R_5$=1-ethylpiperazine (n=3)
$R_1$=3H-benzo[d]imidazol-5-yl
Compound 345. $R_5$=1-methylpiperazine (n=3)
$R_1$=1H-indol-6-yl
Compound 255. $R_5$=4-methoxybenzeneamine (n=3)
Compound 256. $R_5$=3-methoxybenzeneamine (n=3)
Compound 259. $R_5$=2-methoxybenzeneamine (n=3)
Compound 260. $R_5$=3,5-dimethoxybenzenamine (n=3)
Compound 262. $R_5$=thiophene-2-amine (n=3)
Compound 268. $R_5$=dimethylamine (n=3)
Compound 274. $R_5$=pyridine-3-amine (n=3)
Compound 275. $R_5$=methylamine (n=3)
Compound 282. $R_5$=isopropylamine (n=3)
Compound 283. $R_5$=isobutylamine (n=3)
Compound 287. $R_5$=butylamine (n=3)
Compound 288. $R_5$=4-methylpentylamine (n=3)
Compound 289. $R_5$=N,N-dimethylpropane-1,3-diamine (n=3)
Compound 290. $R_5$=cyclohexylmethylamine (n=3)

Compound 294. $R_5$=diethylamine (n=3)
Compound 295. $R_5$=ethylamine (n=3)
Compound 306. $R_5$=morpholine (n=3)
Compound 309. $R_5$=1-methylpiperazine (n=3)
Compound 317. $R_5$=2,6-dimethylmorpholine (n=3)
Compound 323. $R_5$=1-isopropylpiperazine (n=3)
Compound 324. $R_5$=pyrrolidine (n=3)
Compound 329. $R_5$=1-(piperazin-1-yl)ethanone (n=3)
Compound 330. $R_5$=1-methylhomopiperazine (n=3)
Compound 335. $R_5$=1-benzylpiperazine (n=3)
Compound 339. $R_5$=1-ethylpiperazine (n=3)
Compound 343. $R_5$=1-(2-methoxyphenyl)piperazine (n=3)
Compound 344. $R_5$=1-(3-methoxyphenyl)piperazine (n=3)
Compound 346. $R_5$=2-(piperazin-1-yl)ethanol (n=3)
Compound 349. $R_5$=1-butylpiperazine (n=3)
Compound 352. $R_5$=N,N-dimethyl-2-(piperazin-1-yl)ethanamine (n=3)
Compound 356 $R_5$=4-methylpiperidine (n=3)

As shown in reaction scheme 2 above, the compound of formula III is synthesized in the same manner as reaction scheme 1, and then allowed to react 4-nitrophenylchloroformate so as to synthesize the compound of formula VI, which is then subjected to the Suzuki reaction (Morris, G. A., et al., Tetrahedron Lett., 2001, 42, 2093) using boronic acid, thus synthesizing the compound of formula VII. Various substituents are added to the compound of formula VII, thus synthesizing the compound of formula VIII. To the compound of formula VIII, potassium hydroxide (KOH), methanol and hydroxyamine hydrochloride (HONH$_2$HCl) are sequentially added dropwise, and the mixture is allowed to react at mom temperature, thus preparing desired final compounds. Reaction scheme 2 shows a general process for synthesizing inventive compounds 255, 256, 259, 260, 262, 268, 274, 275, 282, 283, 287, 288, 289, 290, 294, 295, 306, 309, 312, 313, 315, 316, 317, 318, 319, 323, 324, 329, 330, 335, 336, 339, 340, 343, 344, 345, 346, 347, 348, 349, 350, 351, 352, 353 and 356. Other compounds of the present invention can also be prepared according to reaction scheme 2.

V, X, Y and Z=CH
Compound 170. $R_1$=1H-indol-4-yl, $R_2$=hydrogen
Compound 179. $R_1$=1H-indol-7-yl, $R_2$=hydrogen
Compound 191. $R_1$=1-(phenylsulfonyl)-1H-indol-2-yl, $R_2$=hydrogen
Compound 332. $R_1$=1H-indol-2-yl, $R_2$=methanesulfonyl
Compound 333. $R_1$=1-(tert-butoxycarbonyl)-1H-indol-2-yl, $R_2$=methanesulfonyl
Compound 337. $R_1$=5-bromo-1H-indol-2-yl, $R_2$=methanesulfonyl
Compound 338. $R_1$=5-bromo-1-(tert-butoxycarbonyl)-1H-indol-2-yl, $R_2$=methanesulfonyl
V=N, and X, Y and Z=CH
Compound 174. $R_1$=1H-indol-6-yl, $R_2$=hydrogen
V, Y and Z=CH, and X=N
Compound 175. $R_1$=1H-indol-6-yl, $R_2$=hydrogen
Compound 326. $R_1$=1H-indol-6-yl, $R_2$=methanesulfonyl
Compound 327. $R_1$=1-methyl-1H-indazol-6-yl, $R_2$=methanesulfonyl
Compound 328. $R_1$=1H-indol-5-yl, $R_2$=methanesulfonyl
V and Z=N, and X and Y=CH
Compound 178. $R_1$=1H-indol-6-yl, $R_2$=hydrogen
V, Y and Z=CH, and X=CCF$_3$
Compound 251. $R_1$=1H-indol-6-yl, $R_2$=hydrogen
Compound 252. $R_1$=1H-indol-6-yl, $R_2$=nicotinoyl
V, Y and Z=CH, and X=CCH$_3$
Compound 254. $R_1$=1H-indol-6-yl, $R_2$=4-methoxybenzoyl Reaction scheme 3 above shows a general process for synthesizing inventive compounds 170, 174, 175, 178, 179, 191, 251, 252, 254, 326, 327, 328, 332, 333, 337 and 338. As shown in reaction scheme 3, the compound of formula IX or X is used as a starting material and subjected to the Suzuki reaction (Morris, G. A., et al., Tetrahedron Lett., 2001, 42, 2093) using boronic acid, thus synthesizing the compound of formula XI. To the compound of formula XI, potassium hydroxide (KOH), methanol and hydroxylamine hydrochlo-

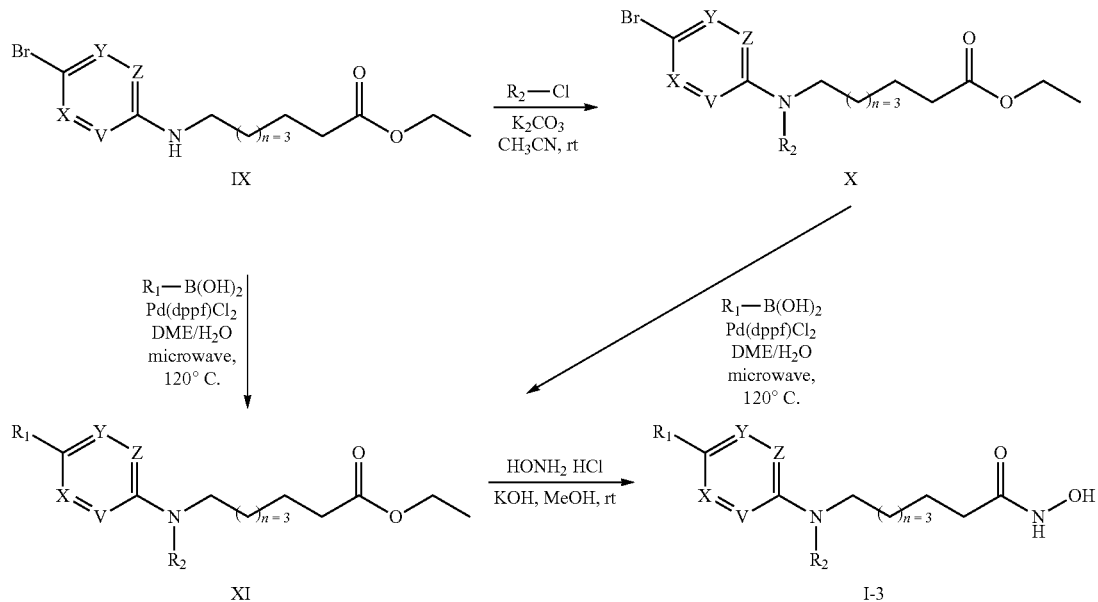

[Reaction Scheme 3]

ride (HONH$_2$HCl) are sequentially added dropwise, and the mixture is allowed to react at mom temperature, thus preparing desired final compounds.

4, compound 1 is subjected to the Suzuki coupling reaction to prepare compound 2, and the nitro group of compound 2 is reduced to obtain compound 3, which is then allowed to react

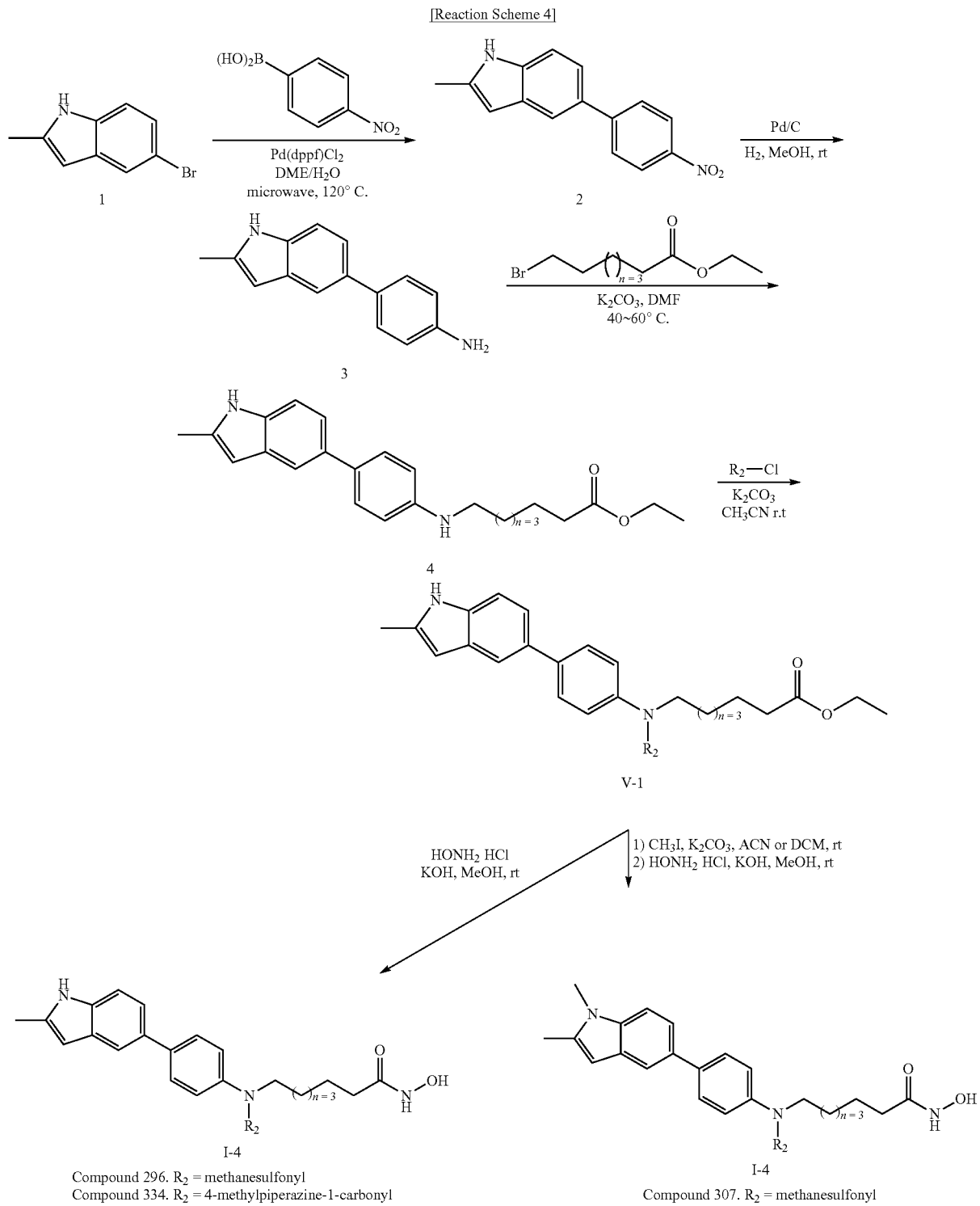

[Reaction Scheme 4]

Compound 296. R$_2$ = methanesulfonyl
Compound 334. R$_2$ = 4-methylpiperazine-1-carbonyl Compound 307. R$_2$ = methanesulfonyl Reaction scheme 4 above shows a general process of preparing inventive compounds 296, 307 and 334, and other compounds of the present invention can also be prepared according to reaction scheme 4. As shown in reaction scheme 4, compound 1 is subjected to the Suzuki coupling reaction to prepare compound 2, and the nitro group of compound 2 is reduced to obtain compound 3, which is then allowed to react with ethyl 7-bromoheptanoate, thus synthesizing compound 4. Then, compound 4 is sulfonylated or acylated to prepare the compound of formula V-1, after which potassium hydroxide (KOH), methanol and hydroxylamine hydrochloride (HONH$_2$HCl) are sequentially added dropwise thereto, or compound 4 is methylated, after which potassium hydroxide (KOH), methanol and hydroxylamine hydrochloride (HONH$_2$HCl) are sequentially added dropwise thereto, thus preparing a final compound.

shown in reaction scheme 5, the starting material is allowed to react with methanesulfonyl and ethyl 7-bromoheptanoate sequentially, and the resulting product is subjected to the Suzuki reaction to synthesize the compound of formula XII, which is then N-methylated and hydroxamated, thus synthesizing final compounds 320 and 321.

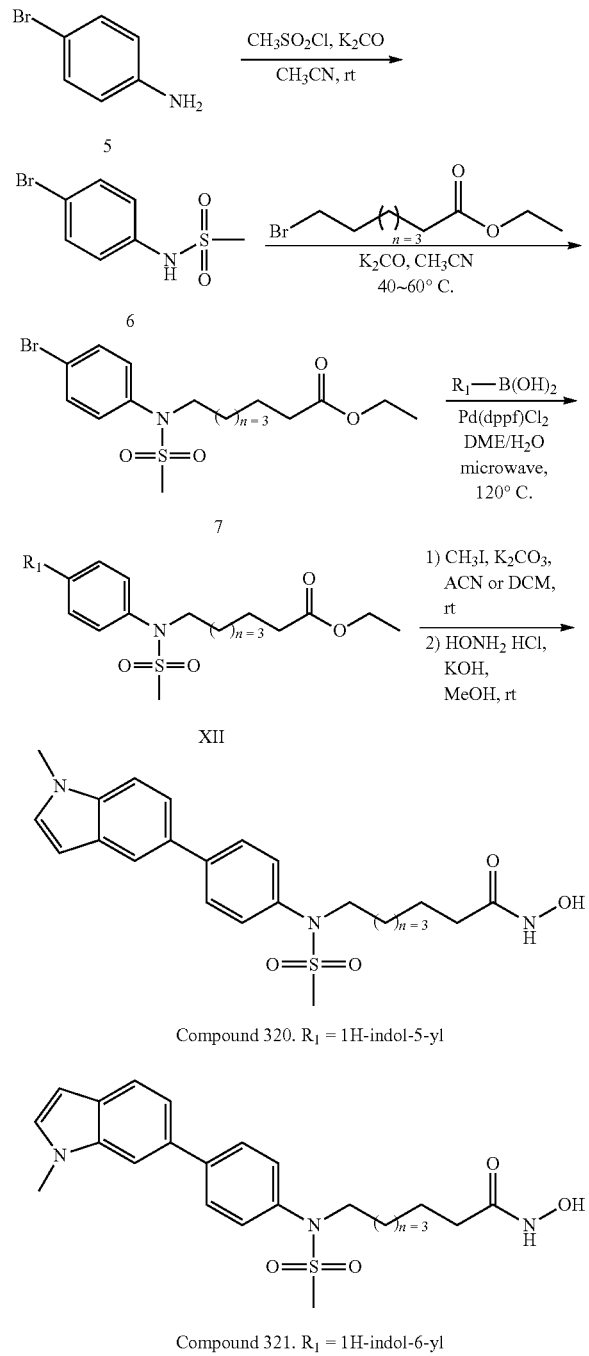

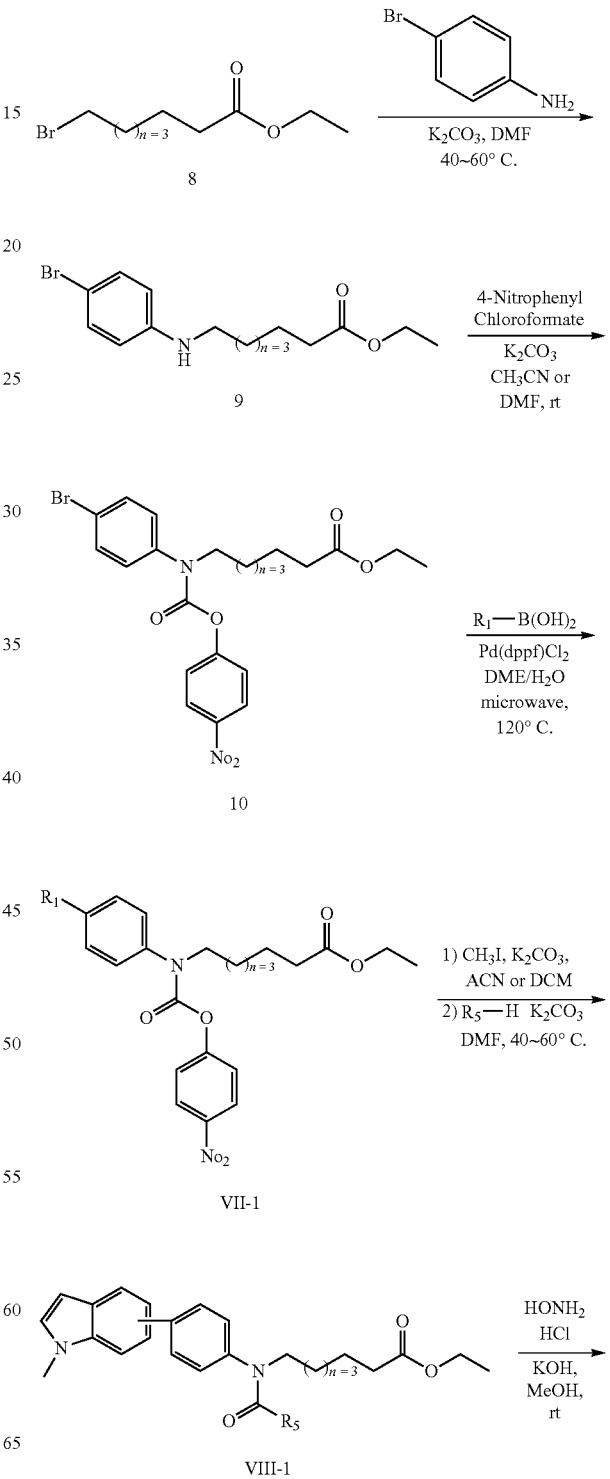

Reaction scheme 5 above shows a general process of synthesizing compounds by introducing methanesulfonyl into compound 5, and other compounds of the present invention can also be prepared according to reaction scheme 5. As -continued

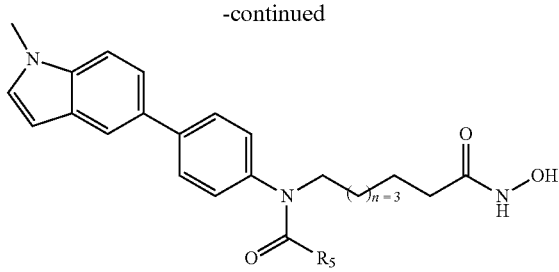

Compound 341. R₅ = 1-methylpiperazine

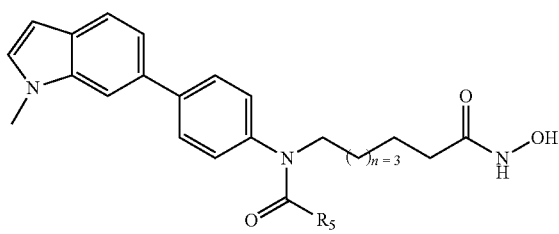

Compound 331. R₅ = 1-methylpiperazine

Reaction scheme 6 above shows a general process of synthesizing inventive compounds 331 and 341, and other compounds of the present invention can also be prepared according to reaction scheme 6. As shown in Reaction Scheme 6, the compound of formula VII-1 is synthesized in the same manner as in reaction scheme 2, after which the compound of formula VII-1 is N-methylated and substituted with piperazine to make the compound of formula VIII-1 which is then hydroxamated, thus synthesizing final compounds.

-continued

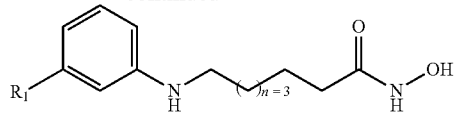

Compound
166. R₁ = 6-indole
169. R₁ = 5-indole
176. R₁ = 7-indole

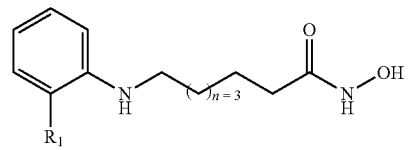

Compound 172.
R₁ = 5-indole

I-7

Reaction scheme 7 above shows a general process of synthesizing inventive compounds 166, 169, 172 and 176, and other compounds of the present invention can also be prepared according to reaction scheme 7. As shown in reaction scheme 7, the compound of formula XIII that is the starting material is subjected to the Suzuki reaction to synthesize the compound of formula XIV, which is then N-alkylated with ethyl 7-bromoheptanoate to synthesize the compound of formula XV, which is then hydroxamated, thus synthesizing final compounds.

[Reaction Scheme 7]

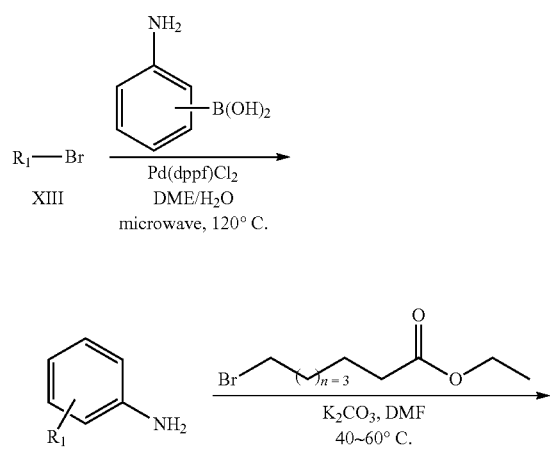

[Reaction Scheme 8]

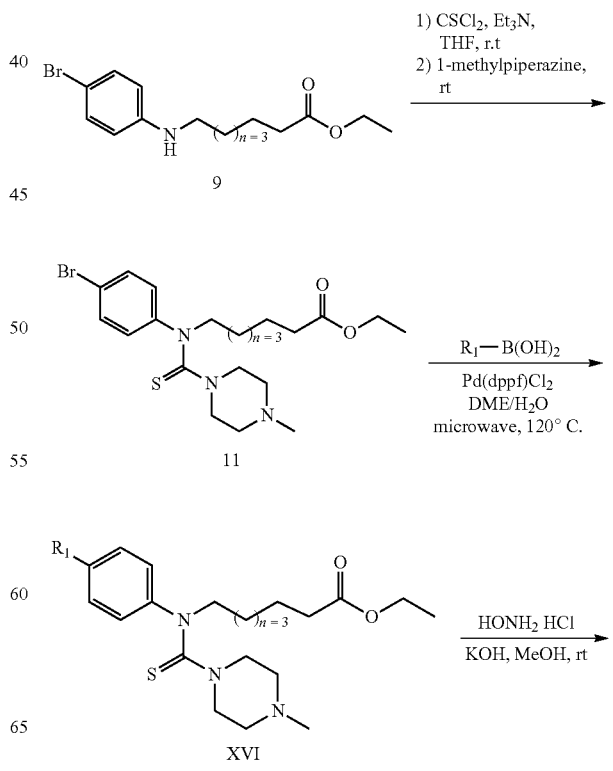

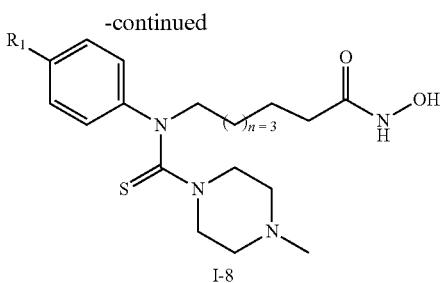

Compound 357. R₁ = 1H-indol-6-yl
Compound 358. R₁ = 1H-indol-5-yl
Compound 359. R₁ = 1-methyl-1H-indazol-5-yl Reaction scheme 8 above shows a general process of synthesizing inventive compounds 357, 358 and 359, and other compounds of the present invention can also be prepared according to reaction scheme 8. As shown in reaction scheme 9, compound 9 is allowed to react with thiophosgene and methylpiperazine so as to synthesize compound 11, which is then subjected to the Suzuki reaction to synthesize the compound of formula XVI, which is then hydroxamated, thus synthesizing final compounds.

EXAMPLES

Hereinafter, the present invention will be described in further detail with reference to examples. It is to be understood, however, that these examples are illustrative purposes only and are not construed to limit the scope of the present invention.

Compound 150

7-(4-(1H-indol-5-yl)phenylamino)-N-hydroxyheptanamide

As shown in reaction scheme 1, 4-bromoaniline and ethyl 7-bromoheptanoate were reacted with each other to obtain a compound of formula III, which was then subjected to the Suzuki reaction to obtain a compound of formula IV, which was then stirred with hydroxylamine and potassium hydroxide for 30 minutes. Then, a 50% water solution of hydroxylamine was added to the stirred solution until the undissolved solids were dissolved so that the solution became clear. Then, the reaction solution was stirred at mom temperature for 10 hours. After the completion of the reaction has been confirmed, the reaction product was distilled under reduced pressure to remove the solvent, and the remaining material was extracted using ethyl acetate, washed with brine, dried with anhydrous magnesium sulfate, filtered, and concentrated under reduced pressure. The residue was crystallized, thus obtaining compound 150 (30 mg, 62%).

$^1$H NMR (400 MHz, CD$_3$OD) δ 7.42 (m, 2H), 7.17 (m, 1H), 7.11 (m, 1H), 6.92 (dd, J=2.4, 0.5 Hz, 1H), 6.70 (d, J=8.7 Hz, 1H), 6.66 (dd, J=8.7, 2.3 Hz, 1H), 644 (dd, J=3.1, 0.8 Hz, 1H), 6.26 (dd, J=3.1, 0.8 Hz, 2H), 3.09 (t, J=7.1 Hz, 2H), 2.09 (t, J=7.3 Hz, 2H), 1.63 (m, 4H), 1.44 (m, 4H). MS (ESI) m/z 352 (M$^+$+H).

Compound 158

N-hydroxy-7-(4-(1-methyl-1H-indol-5-yl)phenylamino)heptanamide

As shown in reaction scheme 1, 4-bromoaniline and ethyl 7-bromoheptanoate were reacted with each other to obtain a compound of formula III, which was then subjected to the Suzuki reaction with boronic acid, and the resulting compound was stirred with hydroxylamine and potassium hydroxide for 30 minutes. Then, a 50% water solution of hydroxylamine was added to the stirred solution until the undissolved solids were dissolved so that the solution became clear. Then, the reaction solution was stirred at mom temperature for 10 hours, and after the completion of the reaction has been confirmed, the reaction product was concentrated under reduced pressure to remove the solvent. The remaining material was extracted using ethyl acetate, washed with brine, dried with anhydrous magnesium sulfate, filtered, and concentrated under reduced pressure. The residue was crystallized, thus obtaining 158 (39 mg, 41%).

$^1$H NMR (400 MHz, CD$_3$OD) δ 7.66 (s, 1H), 7.41 (d, J=8.7 Hz, 2H), 7.35 (s, 1H), 7.11 (d, J=3.1 Hz, 1H), 6.71 (d, J=8.7 Hz, 2H), 6.41 (d, J=3.1 Hz, 1H), 3.19 (s, 3H), 3.10 (t, J=7.2 Hz, 2H), 2.10 (t, J=7.5 Hz, 2H), 1.62 (m, 4H), 1.25 (m, 4H). MS (ESI) m/z 366 (M$^+$+H)

Compound 166

7-(3-(1H-indol-6-yl)phenylamino)-N-hydroxyheptanamide

As shown in reaction scheme 7, a compound of formula XIV was obtained through the Suzuki reaction and then was allowed to react with ethyl 7-bromoheptanoate so as to obtain a compound of formula XV, after which the compound of formula XV (10 mg, 0.03 mmol) was stirred with hydroxylamine and potassium hydroxide for 30 minutes. Then, a 50% water solution of hydroxylamine was added to the stirred solution until the undissolved solids were dissolved so that the solution became clear. Then, the reaction solution was stirred at mom temperature for 10 hours, and after the completion of the reaction has been confirmed, the reaction product was concentrated under reduced pressure to remove the solvent. The remaining material was extracted using ethyl acetate, washed with brine, dried with anhydrous magnesium sulfate, filtered, and concentrated under reduced pressure. The residue was crystallized, thus obtaining 166 (7 mg, 73%).

$^1$H NMR (400 MHz, CDCl$_3$) δ 7.56 (m, 2H), 7.31 (m, 3H), 6.92 (m, 2H), 6.63 (m, 1H), 6.37 (m, 1H), 3.14 (m, 2H), 2.14 (m, 2H), 1.67 (m, 4H), 1.41 (m, 4H). MS (ESI) m/z 352 (M$^+$+H).

Compound 167

7-(4-(1H-indol-6-yl)phenylamino)-N-hydroxyheptanamide

Compound 167 (35 mg, 52%) as a white solid was obtained according to the same method as the synthesis of compound 150.

$^1$H NMR (400 MHz, CD$_3$OD) δ 7.52 (d, J=8.3 Hz, 1H), 7.51 (s, 1H), 7.43 (dd, J=6.6, 2.0 Hz, 1H), 7.22 (dd, J=8.3, 1.6 Hz, 1H), 7.19 (d, J=3.1 Hz, 1H), 6.70 (dd, J=6.7, 2.0 Hz, 2H), 6.40 (dd, J=3.1, 0.8 Hz, 1H), 3.10 (t, J=7.1 Hz, 2H), 2.10 (t, J=7.4 Hz, 2H), 1.62 (m, 4H), 1.41 (m, 2H). MS (ESI) m/z 352 (M$^+$+H).

Compound 169

7-(3-(1H-indol-5-yl)phenylamino)-N-hydroxyheptanamide

Compound 169 (8 mg, 70%) as a white solid was obtained according to the same method as the synthesis of compound 166.

¹H NMR (400 MHz, CDCl₃) δ 7.74 (d, J=1.4 Hz, 1H), 7.38 (m, 2H), 7.24 (d, J=3.1 Hz, 1H), 7.15 (m, 2H), 6.92 (m, 2H), 6.60 (m, 1H), 6.47 (d, J=3.0 Hz, 1H), 3.14 (m, 2H), 2.11 (m, 2H), 1.66 (m, 4H), 1.42 (m, 4H). MS (ESI) m/z 352 (M⁺+H).

Compound 170

7-(4-(1H-indol-4-yl)phenylamino)-N-hydroxyheptanamide

As shown in reaction scheme 3, a compound of formula IX was subjected to the Suzuki reaction to obtain a compound of formula XI, which was then stirred with hydroxylamine and potassium hydroxide for 30 minutes. Then, a 50% water solution of hydroxylamine was added to the stirred solution until the undissolved solids were dissolved so that the solution became clear. Then, the reaction solution was stirred at mom temperature for 10 hours, and after the completion of the reaction has been confirmed, the reaction product was concentrated under reduced pressure to remove the solvent. The remaining material was extracted using ethyl acetate, washed with brine, dried with anhydrous magnesium sulfate, filtered, and concentrated under reduced pressure. The residue was crystallized, thus obtaining compound 170 (15 mg, 78%).

¹H NMR (400 MHz, CD₃OD) δ 7.45 (dd, J=6.5, 2.1 Hz, 2H), 7.29 (d, J=8.2 Hz, 1H), 7.19 (d, J=3.2 Hz, 1H), 7.17 (t, J=8.2 Hz, 1H), 7.01 (dd, J=7.2, 0.8 Hz, 1H), 6.87 (dd, J=6.5, 2.1 Hz, 2H), 6.55 (dd, J=3.2, 0.8 Hz, 1H), 4.17 (t, J=7.0 Hz, 2H), 2.05 (t, J=7.5 Hz, 2H), 1.58 (m, 2H), 1.33 (m, 6H). MS (ESI) m/z 352 (M⁺+H).

Compound 172

7-(2-(1H-indol-5-yl)phenylamino)-N-hydroxyheptanamide

Compound 172 (3 mg, 21%) as a white solid was obtained according to the same method as the synthesis of compound 166.

¹H NMR (400 MHz, CD₃OD) δ 7.50 (d, J=1.3, 1H), 7.45 (d, J=8.3 Hz, 1H), 7.27 (d, J=3.2, 1H), 7.15 (m, 1H), 7.06 (m, 2H), 6.71 (m, 2H), 6.46 (dd, J=3.1, 0.6 Hz, 1H), 3.07 (t, J=6.9 Hz, 2H), 2.02 (t, J=7.6 Hz, 2H), 1.51 (m, 4H), 1.29 (m, 4H). MS (ESI) m/z 352 (M⁺+H)

Compound 174

7-(5-(1H-indol-6-yl)pyridin-2-ylamino)-N-hydroxyheptanamode

Compound 174 (3 mg, 23%) as a white solid was obtained according to the same method as the synthesis of compound 170.

¹H NMR (400 MHz, CD₃OD) δ 8.19 (d, J=2.4 Hz, 1H), 7.75 (dd, J=8.7, 2.5 Hz, 1H), 7.57 (d, J=8.3 Hz, 1H), 7.50 (d, J=8.3 Hz, 1H), 7.50 (d, J=0.7 Hz, 1H), 7.23 (t, J=3.3 Hz, 1H), 7.18 (dd, J=8.3, 1.6 Hz, 1H), 6.60 (d, J=8.7 Hz, 1H), 6.43 (dd, J=3.1, 0.9 Hz, 1H), 3.31 (m, 2H), 2.10 (t, J=7.4 Hz, 2H), 1.65 (m, 4H), 1.43 (m, 4H). MS (ESI) m/z 353 (M⁺+H).

Compound 175

7-(6-(1H-indol-6-yl)pyridin-3-ylamino)-N-hydroxyheptanamide

Compound 175 (11 mg, 33%) as a white solid was obtained according to the same method as the synthesis of compound 170.

¹H NMR (400 MHz, CD₃OD) δ 7.95 (d, J=2.7 Hz, 1H), 7.79 (s, 1H), 7.59 (d, J=5.8 Hz, 1H), 7.57 (d, J=5.5 Hz, 1H), 7.45 (dd, J=8.3, 1.6 Hz, 1H), 7.25 (d, J=3.1 Hz, 1H), 7.08 (dd, J=8.7, 2.8 Hz, 1H), 6.44 (dd, J=3.1, 0.7 Hz, 1H), 3.12 (t, J=7.0 Hz, 2H), 2.10 (t, J=7.4 Hz, 2H), 1.64 (m, 4H), 1.42 (m, 4H). MS (EST) m/z 353 (M⁺+H).

Compound 176

7-(3-(1H-indol-7-yl)phenylamino)-N-hydroxyheptanamide

Compound 176 (22 mg, 56%) as a white solid was obtained according to the same method as the synthesis of compound 166.

¹H NMR (400 MHz, CD₃OD) δ 7.51 (d, J=8.8 Hz, 1H), 7.23 (m, 2H), 7.08 (m, 2H), 6.67 (d, J=1.4 Hz, 1H), 6.49 (d, J=3.1 Hz, 1H), 3.12 (t, J=7.1 Hz, 2H), 2.09 (t, J=7.4 Hz, 2H), 1.63 (m, 4H), 1.40 (m, 4H). MS (ESI) m/z 352 (M⁺+H).

Compound 178

7-(5-(1H-indol-6-yl)pyrimidin-2-ylamino)-N-hydroxyheptanamide

Compound 178 (39 mg, 84%) as a white solid was obtained according to the same method as the synthesis of compound 170.

¹H NMR (400 MHz, CD₃OD) δ 8.56 (s, 2H), 7.58 (d, J=8.2 Hz, 1H), 7.49 (s, 1H), 7.19 (d, J=3.1 Hz, 1H), 7.16 (dd, J=8.2, 1.4 Hz, 1H), 6.42 (d, J=2.9 Hz, 1H), 4.16 (t, J=6.9 Hz, 2H), 2.04 (t, J=7.4 Hz, 2H), 1.78 (m, 2H), 1.30 (m, 6H). MS (ESI) m/z 354 (M⁺+H).

Compound 179

7-(4-(1H-indol-7-yl)phenylamino)-N-hydroxyheptanamide

Compound 179 (12 mg, 82%) as a white solid was obtained according to the same method as the synthesis of compound 170.

¹H NMR (400 MHz, CD₃OD) δ 7.47 (dd, J=7.9, 1.0 Hz, 1H), 7.13 (d, J=8.3 Hz, 2H), 7.08 (d, J=3.1 Hz, 2H), 6.99 (t, J=7.8 Hz, 1H), 6.84 (d, J=6.2 Hz, 1H), 6.80 (d, J=8.4 Hz, 2H), 6.44 (d, J=3.2 Hz, 1H), 3.76 (t, J=7.6 Hz, 2H), 1.98 (t, J=7.6 Hz, 2H), 1.43 (m, 2H), 1.30 (m, 2H), 1.04 (m, 2H), 0.86 (m, 2H). MS (ESI) m/z 352 (M⁺+H).

Compound 180

N-(4-(1H-indol-6-yl)phenyl)-N-(7-(hydroxyamino)-7-oxoheptyl)-4-methoxybenzamide

As shown in reaction scheme 1,4-bromoaniline and ethyl 7-bromoheptanoate were reacted with each other to obtain a compound of formula III, which was then subjected to the Suzuki reaction with indole 6-boronic acid to obtain a compound of formula IV, which was then acylated with 4-methoxybenzoyl chloride to obtain a compound of formula V, after which the compound (31 mg, 0.06 mmol) of formula V was stirred with hydroxylamine and potassium hydroxide for 30 minutes. Then, a 50% water solution of hydroxylamine was added to the stirred solution until the undissolved solids were dissolved so that the solution became clear. Then, the reaction solution was stirred at mom temperature for 10 hours, and after the completion of the reaction has been confirmed, the reaction product was concentrated under reduced pressure to remove the solvent. The remaining material was extracted using ethyl acetate, washed with brine, dried with anhydrous magnesium sulfate, filtered, and concentrated under reduced pressure. The residue was crystallized, thus obtaining compound 180 (12 mg, 41%).

$^1$H NMR (400 MHz, CD$_3$OD) δ 7.57 (m, 4H), 7.27 (m, 4H), 7.13 (d, J=8.4 Hz, 2H), 6.74 (d, J=8.8 Hz, 2H), 6.43 (m, 1H), 3.93 (m, 2H), 3.70 (s, 3H), 2.05 (m, 2H), 1.60 (m, 4H), 1.36 (m, 4H). MS (ESI) m/z 352 (M$^+$+H).

Compound 181

N-(4-(1H-indol-6-yl)phenyl)-N-(7-(hydroxyamino)-7-oxoheptyl)nicotinamide

Compound 181 (10 mg, 45%) as a white solid was obtained according to the same method as the synthesis of compound 180.

$^1$H NMR (400 MHz, CD$_3$OD) δ 8.47 (s, 1H), 8.40 (d, J=3.9 Hz, 1H), 7.79 (d, J=7.5 Hz, 1H), 7.58 (m, 4H), 7.27 (m, 5H), 6.45 (d, J=2.9 Hz, 1H), 5.50 (s, 1H), 3.99 (t, J=6.8 Hz, 2H), 2.09 (t, J=7.4 Hz, 2H), 1.65 (m, 4H), 1.30 (m, 4H). MS (ESI) m/z 457 (M$^+$+H).

Compound 184

7-(N-(4-(1H-indol-6-yl)phenyl)-2-phenylacetamido)-N-hydroxyheptanamide

Compound 184 (27 mg, 82%) as a white solid was obtained according to the same method as the synthesis of compound 180.

$^1$H NMR (400 MHz, CD$_3$OD) δ 7.71 (d, J=8.4 Hz, 2H), 7.65 (m, 2H), 7.34 (m, 1H), 7.29 (d, J=3.1 Hz, 1H), 7.21 (m, 5H), 7.04 (d, J=6.8 Hz, 2H), 6.48 (d, J=3.1 Hz, 1H), 3.74 (t, J=7.4 Hz, 2H), 3.51 (s, 2H), 2.07 (t, J=7.4 Hz, 2H), 1.57 (m, 4H), 1.32 (m, 4H). MS (ESI) m/z 470 (M$^+$+H).

Compound 185

Phenyl 4-(1H-indol-6-yl)phenyl(7-(hydroxyamino)-7-oxoheptyl)carbamate

Compound 185 (20 mg, 51%) as a white solid was obtained according to the same method as the synthesis of compound 180.

$^1$H NMR (400 MHz, CD$_3$OD) δ 7.73 (d, J=1.9 Hz, 2H), 7.62 (m, 2H), 7.42 (m, 5H), 7.24 (m, 2H), 7.11 (m, 2H), 6.47 (d, J=1.9 Hz, 1H), 3.81 (m, 2H), 2.10 (m, 2H), 1.62 (m, 4H), 1.38 (m, 4H). MS (ESI) m/z 472 (M$^+$+H).

Compound 189

Benzyl 4-(1H-indol-6-yl)phenyl(7-(hydroxyamino)-7-oxoheptyl)carbamate

Compound 189 (12 mg, 51%) as a white solid was obtained according to the same method as the synthesis of compound 180.

$^1$H NMR (400 MHz, CD$_3$OD) δ 7.63 (m, 4H), 7.29 (m, 9H), 6.47 (s, 1H), 5.15 (s, 2H), 3.73 (t, J=7.5 Hz, 2H), 2.05 (t, J=7.5 Hz, 2H), 1.58 (m, 4H), 1.32 (m, 4H). MS (ESI) m/z 486 (M$^+$+H).

Compound 190

7-((4-(1H-indol-6-yl)phenyl)(2-hydroxyethyl)amino)-N-hydroxyheptanamide

Compound 190 (8 mg, 28%) as a white solid was obtained according to the same method as the synthesis of compound 180.

MS (ESI) m/z 396 (M$^+$+H).

Compound 191

N-hydroxy-7-(4-(1-(phenylsulfonyl)-1H-indol-2-yl)phenylamino)heptanamide

Compound 191 (320 mg, 39%) as a white solid was obtained according to the same method as the synthesis of compound 170.

$^1$H NMR (400 MHz, CD$_3$OD) δ 8.21 (d, J=8.3 Hz, 1H), 7.29 (m, 10H), 6.61 (d, J=8.6 Hz, 2H), 6.40 (s, 1H), 3.10 (t, J=7.0 Hz, 2H), 2.10 (t, J=7.4 Hz, 2H), 1.64 (m, 4H), 1.42 (m, 4H). MS (ESI) m/z 492 (M$^+$+H).

Compound 203

7-(N-(4-(1H-indol-6-yl)phenyl)thiophene-2-sulfonamido)-N-hydroxyheptanamide

Compound 203 (4 mg, 15%) as a yellow oil was obtained according to the same method as the synthesis of compound 180.

$^1$H NMR (400 MHz, CD$_3$OD) δ 7.79 (m, 2H), 7.64 (s, 1H), 7.61 (m, 2H), 7.43 (s, 1H), 7.26 (m, 4H), 6.48 (m, 1H), 6.31 (m, 1H), 5.94 (s, 1H), 3.86 (m, 2H), 2.07 (m, 2H), 1.64 (m, 4H), 1.35 (m, 4H). MS (EST) m/z 497 (M$^+$+H).

Compound 204

N-(4-(1H-indol-6-yl)phenyl)-N-(7-(hydroxyamino)-7-oxoheptyl)furan-2-carboxamide

Compound 204 (4 mg, 14%) as a yellow oil was obtained according to the same method as the synthesis of compound 180.

$^1$H NMR (400 MHz, CD$_3$OD) δ 7.82 (d, J=4.9 Hz, 1H), 7.62 (m, 4H), 7.43 (d, J=3.6 Hz, 1H), 7.29 (m, 2H), 7.15 (m, 3H), 6.47 (d, J=2.7 Hz, 1H), 3.66 (t, J=6.1 Hz, 2H), 3.07 (t, J=7.3 Hz, 2H), 1.58 (m, 2H), 1.46 (m, 2H), 1.32 (m, 4H). MS (EST) m/z 446 (M$^+$+H).

Compound 207

7-(N-(4-(1H-indol-6-yl)phenyl)-4-methoxyphenylsulfonamido)-N-hydroxyheptanamide

Compound 207 (54 mg, 6%) as a white solid was obtained according to the same method as the synthesis of compound 180.

$^1$H NMR (400 MHz, CD$_3$OD) δ 7.57 (m, 6H), 7.26 (m, 2H), 7.05 (d, J=8.4 Hz, 2H), 7.00 (d, J=8.9 Hz, 2H), 6.45 (d, J=3.1 Hz, 1H), 3.83 (s, 3H), 3.53 (t, J=6.2 Hz, 2H), 2.04 (t, J=7.4 Hz, 2H), 1.54 (m, 2H), 1.36 (m, 4H), 1.29 (m, 2H). MS (EST) m/z 522 (M$^+$+H).

Compound 208

N-(4-(1H-indol-5-yl)phenyl)-N-(7-(hydroxyamino)-7-oxoheptyl)-4-methoxybenzamide

Compound 208 (8 mg, 22%) as a white solid was obtained according to the same method as the synthesis of compound 180.

$^1$H NMR (400 MHz, CD$_3$OD) δ 7.75 (d, J=1.16 Hz, 1H), 7.56 (d, J=8.44 Hz, 1H), 7.41 (m, 1H), 7.32 (m, 2H), 7.24 (d, J=3.08 Hz, 1H), 7.13 (d, J=8.36 Hz, 1H), 6.75 (d, J=8.76 Hz, 1H), 6.47 (d, J=2.48 Hz, 1H), 3.94 (t, J=7.38 Hz, 2H), 2.07 (t, J=7.38 Hz, 2H), 1.62 (m, 4H), 1.28 (m, 4H). MS (ESI) m/z 486 (M$^+$+H).

Compound 209

N-(4-(1H-indol-6-yl)phenyl)-N-(7-(hydroxyamino)-7-oxoheptyl)-4-methylbenzamide

Compound 209 (52 mg, 98%) as a yellow oil was obtained according to the same method as the synthesis of compound 180.

$^1$H NMR (400 MHz, CD$_3$OD) δ 7.54 (m, 4H), 7.22 (m, 4H), 7.10 (d, J=8.1 Hz, 2H), 7.00 (d, J=7.6 Hz, 2H), 6.43 (d, J=2.9 Hz, 2H), 3.91 (t, J=7.2 Hz, 2H), 2.22 (s, 3H), 2.06 (t, J=7.2 Hz, 2H), 1.59 (m, 4H), 1.24 (m, 4H). MS (ESI) m/z 470 (M$^+$+H).

Compound 210

7-(N-(4-(1H-indol-6-yl)phenyl)phenylsulfonamido)-N-hydroxyheptanamide

Compound 210 (14 mg, 27%) as a white solid was obtained according to the same method as the synthesis of compound 180.

$^1$H NMR (400 MHz, CD$_3$OD) δ 7.61 (m, 8H), 7.54 (t, J=7.8 Hz, 1H), 7.28 (dd, J=8.3, 1.6 Hz, 1H), 7.27 (d, J=3.1 Hz, 1H), 7.08 (d, J=8.5 Hz, 2H), 6.45 (dd, J=3.1, 0.8 Hz, 1H), 3.61 (t, J=6.4 Hz, 2H), 2.06 (t, J=7.4 Hz, 2H), 1.57 (m, 2H), 1.42 (m, 4H), 1.31 (m, 2H). MS (ESI) m/z 492(M$^+$+H).

Compound 211

N-(4-(1H-indol-6-yl)phenyl)-N-(7-(hydroxyamino)-7-oxoheptyl)picolinamide

Compound 211 (10 mg, 74%) as a white solid was obtained according to the same method as the synthesis of compound 180.

$^1$H NMR (400 MHz, CD$_3$OD) δ 8.37 (d, J=3.8 Hz, 1H), 7.70 (t, J=7.2 Hz, 1H), 7.52 (m, 4H), 7.39 (d, J=7.8 Hz, 1H), 7.28 (m, 1H), 7.25 (d, J=3.0 Hz, 1H), 7.19 (d, J=8.4 Hz, 1H), 7.15 (d, J=7.9 Hz, 2H), 6.43 (d, J=2.6 Hz, 1H), 4.00 (t, J=7.2 Hz, 2H), 2.09 (t, J=7.3 Hz, 2H), 1.64 (m, 4H), 1.44 (m, 4H). MS (ESI) m/z 457 (M$^+$+H).

Compound 212

N-(4-(1H-indol-6-yl)phenyl)-N-(7-(hydroxyamino)-7-oxoheptyl)-3-methoxybenzamide

Compound 212 (52 mg, 98%) as a yellow oil was obtained according to the same method as the synthesis of compound 180.

$^1$H NMR (400 MHz, CD$_3$OD) δ 7.75 (d, J=1.2 Hz, 1H), 7.56 (d, J=8.4 Hz, 1H), 7.41 (m, 1H), 7.32 (m, 2H), 7.24 (d, J=3.1 Hz, 1H), 7.13 (d, J=8.4 Hz, 1H), 6.75 (d, J=8.8 Hz, 1H), 6.47 (d, J=2.5 Hz, 1H), 3.94 (t, J=7.4 Hz, 2H), 2.07 (t, J=7.4 Hz, 2H), 1.62 (m, 4H), 1.28 (m, 4H). MS (ESI) m/z 470 (M$^+$+H).

Compound 214

N-(4-(1H-indol-6-yl)phenyl)-N-(7-(hydroxyamino)-7-oxoheptyl)-3,4,5-trimethoxybenzamide Compound 214 (10 mg, 25%) as a yellow oil was obtained according to the same method as the synthesis of compound 180.

$^1$H NMR (400 MHz, CD$_3$OD) δ 7.59 (m, 4H), 7.23 (m, 4H), 6.63 (s, 2H), 6.44 (d, 1H, J=2.2 Hz), 3.96 (t, 2H, J=7.0 Hz), 3.68 (s, 3H), 3.49 (s, 6H), 2.08 (t, 2H, J=7.3 Hz), 1.63 (m, 4H), 1.37 (m, 4H). MS (EST) m/z 546 (M$^+$+H).

Compound 215

N-(4-(1H-indol-6-yl)phenyl)-4-(dimethylamino)-N-(7-(hydroxyamino)-7-oxoheptyl)benzamide Compound 215 (10 mg, 52%) as a yellow oil was obtained according to the same method as the synthesis of compound 180.

$^1$H NMR (400 MHz, CD$_3$OD) δ 7.57 (m, 4H), 7.24 (m, 4H), 7.13 (d, J=8.5 Hz, 2H), 6.48 (m, 2H), 6.43 (m, 1H), 3.92 (t, J=7.5 Hz, 2H), 2.87 (s, 6H), 2.05 (m, 2H), 1.61 (m, 4H), 1.36 (m, 4H). MS (ESI) m/z 451 (M$^+$+H).

Compound 218

7-(N-(4-(1H-indol-6-yl)phenyl)-2-aminoacetamido)-N-hydroxyheptanamide

Compound 218 (8 mg, 46%) as a yellow oil was obtained according to the same method as the synthesis of compound 180.

$^1$H NMR (400 MHz, CD$_3$OD) δ 7.78 (d, J=8.3 Hz, 2H), 7.66 (s, 1H), 7.63 (d, J=8.3 Hz, 1H), 7.32 (dd, J=8.3, 1.7 Hz, 2H), 7.31 (m, 1H), 7.28 (d, J=3.1 Hz, 1H), 6.47 (dd, J=3.1, 0.7 Hz, 1H), 3.77 (t, J=7.3 Hz, 2H), 2.07 (d, J=7.3 Hz, 2H), 1.59 (m, 4H), 1.36 (m, 4H). MS (ESI) m/z 409 (M$^+$+H).

Compound 221

N-(4-(1H-indol-6-yl)phenyl)-6-chloro-N-(7-(hydroxyamino)-7-oxoheptyl)nicotinamide Compound 221 (22 mg, 32%) as a yellow oil was obtained according to the same method as the synthesis of compound 180.

$^1$H NMR (400 MHz, CD$_3$OD) δ 8.29 (s, 1H), 7.72 (d, J=7.6 Hz, 1H), 7.62 (m, 4H), 7.25 (m, 5H), 644 (d, J=2.8 Hz, 2H), 3.97 (m, 2H), 2.08 (t, J=7.3 Hz, 2H), 1.62 (m, 4H), 1.28 (m, 4H). MS (ESI) m/z 491 (M$^+$+H).

Compound 222

N-(4-(1H-indol-6-yl)phenyl)-N-(7-(hydroxyamino)-7-oxoheptyl)isonicotinamide

Compound 222 (45 mg, 57%) as a yellow oil was obtained according to the same method as the synthesis of compound 180.

¹H NMR (400 MHz, CD₃OD) δ 8.40 (d, J=5.1 Hz, 2H), 7.56 (m, 4H), 7.27 (m, 3H), 7.16 (m, 3H), 644 (d, J=2.9 Hz, 1H), 3.95 (m, 2H), 2.07 (m, 2H), 1.61 (m, 4H), 1.27 (m, 4H). MS (ESI) m/z 457 (M⁺+H).

Compound 228

(Z)-N-(4-(1H-indol-6-yl)phenyl)-N-(7-(hydroxyamino)-7-oxoheptyl)-4-(N-hydroxycarbamimidoyl)benzamide Compound 228 (51 mg, 41%) as a yellow oil was obtained according to the same method as the synthesis of compound 180.
¹H NMR (400 MHz, CD₃OD) δ 7.70 (d, J=7.6 Hz, 1H), 7.49 (m, 5H), 7.40 (d, J=7.9 Hz, 1H), 7.35 (d, J=7.9 Hz, 1H), 7.25 (d, J=3.1 Hz, 1H), 7.14 (d, J=7.8 Hz, 1H), 6.43 (d, J=3.0 Hz, 1H), 3.95 (m, 2H), 2.07 (t, J=7.4 Hz, 2H), 1.62 (m, 4H), 1.28 (m, 4H). MS (ESI) m/z 514 (M⁺+H).

Compound 229

N-(4-(1H-indol-6-yl)phenyl)-2,6-difluoro-N-(7-(hydroxyamino)-7-oxoheptyl)benzamide Compound 229 (49 mg, 92%) as a yellow oil was obtained according to the same method as the synthesis of compound 180.
¹H NMR (400 MHz, CD₃OD) δ 7.55 (m, 4H), 7.25 (d, J=3.1 Hz, 1H), 7.20 (d, J=8.4 Hz, 1H), 7.16 (d, J=8.2 Hz, 1H), 6.81 (m, 2H), 6.43 (d, J=2.9 Hz, 1H), 3.94 (t, J=7.3 Hz, 2H), 2.04 (m, 2H), 1.61 (m, 4H), 1.31 (m, 4H). MS (ESI) m/z 492 (M⁺+H).

Compound 230

N-(4-(1H-indol-6-yl)phenyl)-4-fluoro-N-(7-(hydroxyamino)-7-oxoheptyl)benzamide

Compound 230 (47 mg, 74%) as a yellow oil was obtained according to the same method as the synthesis of compound 180.
¹H NMR (400 MHz, CD₃OD) δ 7.58 (s, 1H), 7.56 (d, J=2.8 Hz, 1H), 7.51 (d, J=8.4 Hz, 2H), 7.32 (m, 2H), 7.25 (d, J=3.1 Hz, 1H), 7.21 (dd, J=8.4, 1.0 Hz, 1H), 7.05 (d, J=8.2 Hz, 2H), 6.88 (t, J=8.6 Hz, 2H), 6.44 (d, J=3.0 Hz, 1H), 3.86 (t, J=7.4 Hz, 2H), 2.06 (t, J=7.4 Hz, 2H), 1.59 (m, 4H), 1.25 (m, 4H). MS (ESI) m/z 474 (M⁺+H).

Compound 231

N-(4-(1H-indol-6-yl)phenyl)-N-(7-(hydroxyamino)-7-oxoheptyl)-6-(trifluoromethyl)nicotinamide Compound 231 (52 mg, 52%) as a yellow oil was obtained according to the same method as the synthesis of compound 180.
¹H NMR (400 MHz, CD₃OD) δ 8.60 (s, 1H), 7.87 (d, J=7.9 Hz, 1H), 7.61 (d, J=8.2 Hz, 1H), 7.55 (m, 4H), 7.26 (d, J=3.1 Hz, 1H), 7.21 (d, J=9.4 Hz, 1H), 7.15 (d, J=8.0 Hz, 1H), 6.44 (d, J=2.9 Hz, 1H), 3.94 (t, J=6.8 Hz, 2H), 2.08 (t, J=7.4 Hz, 2H), 1.68 (m, 4H), 1.35 (m, 4H). MS (ESI) m/z 525 (M⁺+H).

Compound 234

6-(4-(1H-indol-6-yl)phenylamino)-N-hydroxyhexanamide

Compound 234 (33 mg, 73%) as a yellow oil was obtained according to the same method as the synthesis of compound 150.
¹H NMR (400 MHz, CD₃OD) δ 7.52 (m, 2H), 744 (d, J=6.6 Hz, 2H), 7.22 (m, 2H), 6.71 (d, J=8.5 Hz, 2H), 3.13 (t, J=7.0 Hz, 2H), 2.14 (t, J=7.3 Hz, 2H), 1.67 (m, 4H), 1.47 (m, 4H). MS (ESI) m/z 337 (M⁺+H).

Compound 235

8-(4-(1H-indol-6-yl)phenylamino)-N-hydroxyoctanamide

Compound 235 (33 mg, 73%) as a yellow oil was obtained according to the same method as the synthesis of compound 150.

Compound 236

N-(4-(1H-indol-6-yl)phenyl)-4-ethoxy-N-(7-(hydroxyamino)-7-oxoheptyl)benzamide

Compound 236 (10 mg, 50%) as a yellow oil was obtained according to the same method as the synthesis of compound 180.
¹H NMR (400 MHz, CD₃OD) δ 7.56 (m, 4H), 7.24 (m, 4H), 7.13 (d, J=8.5 Hz, 2H), 6.71 (d, J=8.8 Hz, 2H), 6.43 (m, 1H), 3.93 (q, J=7.0 Hz, 2H), 3.57 (t, J=6.4 Hz, 2H), 2.07 (t, J=7.5 Hz, 2H), 1.65 (m, 4H), 1.37 (m, 4H), 1.30 (t, J=7.0 Hz, 3H). MS (ESI) m/z 501 (M⁺+H).

Compound 237

7-((4-(1H-indol-6-yl)phenyl)(benzyl)amino)-N-hydroxyheptanamide

Compound 237 (40 mg, 29%) as a yellow solid was obtained according to the method as the synthesis of compound 180.
¹H NMR (400 MHz, CD₃OD) δ 7.44 (m, 4H), 7.22 (m, 7H), 6.72 (d, J=8.8 Hz, 2H), 6.39 (d, J=2.8 Hz, 1H), 4.53 (s, 2H), 3.40 (t, J=7.6 Hz, 2H), 2.06 (t, J=7.5 Hz, 2H), 1.60 (m, 4H), 1.32 (m, 4H). MS (ESI) m/z 442 (M⁺+H).

Compound 239

N-(4-(1H-indol-6-yl)phenyl)-2,4,6-trifluoro-N-(7-(hydroxyamino)-7-oxoheptyl)benzamide Compound 239 (50 mg, 90%) as a yellow oil was obtained according to the same method as the synthesis of compound 180.
¹H NMR (400 MHz, CD₃OD) δ 7.56 (m, 4H), 7.24 (m, 4H), 6.79 (m, 2H), 644 (m, 1H), 3.97 (t, J=7.3 Hz, 2H), 2.11 (t, J=7.3 Hz, 2H), 1.66 (m, 4H), 1.25 (m, 4H). MS (ESI) m/z 509 (M⁺+H).

Compound 242

N-(4-(1H-indol-6-yl)phenyl)-4-amino-N-(7-(hydroxyamino)-7-oxoheptyl)benzamide

Compound 242 (47 mg, 71%) as a yellow oil was obtained according to the same method as the synthesis of compound 180.

¹H NMR (400 MHz, CD₃OD) δ 7.56 (m, 4H), 7.25 (m, 2H), 7.12 (m, 4H), 644 (m, 3H), 3.91 (t, J=7.5 Hz, 2H), 2.06 (t, J=7.5 Hz, 2H), 1.59 (m, 4H), 1.33 (m, 4H). MS (ESI) m/z 471 (M⁺+H).

Compound 243

N-(4-(1H-indol-6-yl)phenyl)-N-(7-(hydroxyamino)-7-oxoheptyl)piperidine-1-carboxamide Compound 243 (46 mg, 62%) as a white solid was obtained according to the same method as the synthesis of compound 180.
¹H NMR (400 MHz, CD₃OD) δ 7.6 (m, 4H), 7.26 (m, 2H), 7.08 (d, J=8.0 Hz, 2H), 6.45 (d, J=2.7 Hz, 1H), 3.58 (t, J=7.8 Hz, 2H), 3.13 (m, 4H), 2.11 (t, J=7.5 Hz, 2H), 1.56 (m, 4H), 1.44 (m, 4H), 1.24 (m, 4H). MS (ESI) m/z 462 (M⁺+H).

Compound 244

N-(4-(1H-indol-6-yl)phenyl)-N-(7-(hydroxyamino)-7-oxoheptyl)-4-methoxy-3-(trifluoromethyl)benzamide Compound 244 (55 mg, 55%) as a yellow oil was obtained according to the same method as the synthesis of compound 180.
MS (ESI) m/z 555 (M⁺+H).

Compound 245

N-(4-(1H-indol-6-yl)phenyl)-N-(7-(hydroxyamino)-7-oxoheptyl)-4-(trifluoromethyl)benzamide Compound 245 (10 mg, 50%) as a yellow oil was obtained according to the same method as the synthesis of compound 180.
MS (ESI) m/z 524 (M⁺+H).

Compound 246

N-(4-(1H-indol-6-yl)phenyl)-N-(7-(hydroxyamino)-7-oxoheptyl)-3,4-dimethoxybenzamide Compound 246 (51 mg, 71%) as a yellow oil was obtained according to the same method as the synthesis of compound 180.
MS (ESI) m/z 517 (M⁺+H).

Compound 249

7-(N-(4-(1H-indol-6-yl)phenyl)-3,4-dimethoxyphenylsulfonamido)-N-hydroxyheptanamide Compound 249 (40 mg, 58%) as a yellow oil was obtained according to the same method as the synthesis of compound 180.
¹H NMR (400 MHz, CD₃OD) δ 7.60 (m, 4H), 7.27 (m, 3H), 7.06 (q, J=8.5, 3H), 6.93 (d, J=2.1 Hz, 1H), 6.45 (dd, J=3.1, 0.6 Hz, 1H), 3.87 (s, 3H), 3.67 (s, 3H), 3.56 (t, J=6.2 Hz, 2H), 2.07 (t, J=7.4 Hz, 2H), 1.57 (m, 2H), 1.34 (m, 6H). MS (ESI) m/z 551 (M⁺+H).

Compound 250

7-(N-(4-(1H-indol-6-yl)phenyl)-4-(methylsulfonyl)phenylsulfonamido)-N-hydroxyheptanamide Compound 250 (56 mg, 69%) as a yellow oil was obtained according to the same method as the synthesis of compound 180.
¹H NMR (400 MHz, CD₃OD) δ 8.12 (d, J=7.7 Hz, 2H), 7.86 (d, J=7.7 Hz, 2H), 7.61 (m, 4H), 7.29 (m, 2H), 7.1 (d, J=8.5 Hz, 2H), 6.46 (d, J=3.0 Hz, 1H), 3.64 (t, J=6.3 Hz, 2H), 2.08 (t, J=7.3 Hz, 2H), 1.58 (m, 2H), 1.44 (m, 4H), 1.30 (m, 2H). MS (ESI) m/z 569 (M⁺+H).

Compound 251

7-(4-(1H-indol-6-yl)-3-(trifluoromethyl)phenylamino)-N-hydroxyheptanamide

Compound 251 (15 mg, 33%) as a yellow oil was obtained according to the same method as the synthesis of compound 170.
¹H NMR (400 MHz, CD₃OD) δ 7.48 (d, J=7.7 Hz, 1H), 7.25 (s, 1H), 7.22 (d, J=3.1 Hz, 1H), 7.11 (d, J=8.4 Hz, 1H), 6.93 (d, J=2.4 Hz, 1H), 6.90 (dd, J=8.2, 0.7 Hz, 6.79 (dd, J=8.4, 2.4 Hz, 1H), 6.43 (dd, J=3.1, 0.8 Hz, 1H), 3.12 (t, J=7.0 Hz, 2H), 2.10 (t, J=7.4 Hz, 2H), 1.63 (m, 4H), 1.41 (m, 4H). MS (ESI) m/z 420 (M⁺+H).

Compound 252

N-(4-(1H-indol-6-yl)-3-(trifluoromethyl)phenyl)-N-(7-(hydroxyamino)-7-oxoheptyl)nicotinamide As shown in reaction scheme 3, a compound of formula IX was acylated with nicotinoyl chloride to obtain a compound of formula X, which was then subjected to the Suzuki reaction to obtain a compound of formula XI, which was then stirred with hydroxylamine and potassium hydroxide for 30 minutes. Then, a 50% water solution of hydroxylamine was added to the stirred solution until the undissolved solids were dissolved so that the solution became clear. Then, the reaction solution was stirred at mom temperature for 10 hours, and after the completion of the reaction has been confirmed, the reaction product was concentrated under reduced pressure to remove the solvent. The remaining material was extracted using ethyl acetate, washed with brine, dried with anhydrous magnesium sulfate, filtered, and concentrated under reduced pressure. The residue was crystallized, thus obtaining compound 252 (25 mg, 52%).
¹H NMR (400 MHz, CD₃OD) δ 8.47 (s, 2H), 7.84 (d, J=7.3 Hz, 1H), 7.57 (s, 1H), 744 (m, 4H), 7.27 (m, 1H), 7.24 (s, 1H), 6.86 (d, J=8.1 Hz, 1H), 6.46 (dd, J=3.1, 0.9 Hz, 1H), 4.00 (m, 2H), 2.09 (t, J=7.4 Hz, 2H), 1.62 (m, 4H), 1.23 (m, 4H). MS (ESI) m/z 525(M⁺+H).

Compound 253

7-(N-(4-(1H-indol-6-yl)phenyl)naphthalene-2-sulfonamido)-N-hydroxyheptanamide

Compound 253 (54 mg, 41%) as a yellow oil was obtained according to the same method as the synthesis of compound 180.
¹H NMR (400 MHz, CD₃OD) δ 8.18 (s, 1H), 7.95 (m, 3H), 7.59 (m, 7H), 7.24 (m, 2H), 7.02 (d, J=8.4 Hz, 2H), 6.44 (d, J=2.8 Hz, 1H), 3.61 (t, J=6.0 Hz, 2H), 2.06 (t, J=7.4 Hz, 2H), 1.58 (m, 2H), 1.37 (m, 4H), 1.24 (m, 2H). MS (ESI) m/z 541(M$^+$+H).

Compound 254

N-(4-(1H-indol-6-yl)-3-methylphenyl)-N-(7-(hydroxyamino)-7-oxoheptyl)-4-methoxybenzamide Compound 254 (49 mg, 94%) as a yellow oil was obtained according to the same method as the synthesis of compound 252.
$^1$H NMR (400 MHz, CD$_3$OD) δ 7.53 (d, J=7.8 Hz, 1H), 7.29 (d, J=6.8 Hz, 2H), 7.13 (d, J=8.0 Hz, 1H), 7.03 (d, J=1.8 Hz, 1H), 6.90 (m, 2H), 6.60 (d, J=8.8 Hz, 2H), 7.39 (dd, J=3.1, 0.8 Hz, 1H), 3.92 (t, J=7.4 Hz, 2H), 3.73 (s, 3H), 2.26 (s, 3H), 2.07 (t, J=7.2 Hz, 2H), 1.62 (m, 4H), 1.33 (m, 4H).
MS (ESI) m/z 499 (M$^+$+H).

Compound 255

7-(1-(4-(1H-indol-6-yl)phenyl)-3-(4-methoxyphenyl)ureido)-N-hydroxyheptanamide

As shown in reaction scheme 2,4-bromoaniline and ethyl 7-bromoheptanoate were reacted with each other to obtain a compound of formula III, which was then allowed to react with 4-nitrophenylchloroformate so as to obtain a compound of formula VI, which was then subjected to the Suzuki reaction with boronic acid to obtain a compound of formula VII, which was then allowed to react with 4-methoxybenzenamine so as to obtain a compound of formula VIII, after which the compound of formula VIII (31 mg, 0.06 mmol) was stirred with hydroxylamine and potassium hydroxide for 30 minutes. Then, a 50% water solution of hydroxylamine was added to the stirred solution until the undissolved solids were dissolved so that the solution became clear. Then, the reaction solution was stirred at mom temperature for 10 hours, and after the completion of the reaction has been confirmed, the reaction product was concentrated under reduced pressure to remove the solvent. The remaining material was extracted using ethyl acetate, washed with brine, dried with anhydrous magnesium sulfate, filtered, and concentrated under reduced pressure. The residue was crystallized, thus obtaining compound 255 (12 mg, 41%).
$^1$H NMR (400 MHz, CD$_3$OD) δ 7.80 (d, J=8.44 Hz, 2H), 7.68 (s, 1H), 7.64 (d, J=8.2 Hz, 1H), 7.38 (m, 3H), 7.29 (d, J=3.1 Hz, 1H), 7.19 (dd, J=6.8, 2.8 Hz, 2H), 6.82 (dd, J=6.8, 2.1 Hz, 2H), 6.48 (d, J=3.08 Hz, 1H), 3.74 (m, 5H), 2.08 (t, J=7.3 Hz, 2H), 1.62 (m, 4H), 1.36 (m, 4H). MS (ESI) m/z 500 (M$^+$+H).

Compound 256

7-(1-(4-(1H-indol-6-yl)phenyl)-3-(3-methoxyphenyl)ureido)-N-hydroxyheptanamide

Compound 256 (39 mg, 50%) as a yellow oil was obtained according to the same method as the synthesis of compound 255.
$^1$H NMR (400 MHz, CD$_3$OD) δ 7.78 (d, J=8.1 Hz, 2H), 7.69 (s, 1H), 7.63 (d, J=8.2 Hz, 1H), 7.36 (t, J=8.3 Hz, 3H), 7.28 (d, J=2.7 Hz, 1H), 7.11 (t, J=8.0 Hz, 1H), 7.05 (d, J=1.8 Hz, 1H), 6.82 (d, J=7.6 Hz, 1H), 6.58 (m, 1H), 6.47 (d, J=1.4 Hz, 1H), 3.76 (m, 5H), 2.07 (t, J=7.3 Hz, 2H), 1.61 (m, 4H), 1.35 (m, 4H). MS (ESI) m/z 500 (M$^+$+H).

Compound 257

7-(N-(4-(1H-indol-6-yl)phenyl)acetamido)-N-hydroxyheptanamide

Compound 257 (39 mg, 93%) as a yellow oil was obtained according to the same method as the synthesis of compound 180.
$^1$H NMR (400 MHz, CD$_3$OD) δ 7.75 (d, J=8.3 Hz, 2H), 7.65 (t, J=9.0 Hz, 2H), 7.32 (m, 4H), 6.48 (d, J=3.1 Hz, 1H), 6.48 (d, J=3.1 Hz, 1H), 3.74 (t, J=7.4 Hz, 2H), 3.36 (s, 1H), 2.09 (t, J=7.2 Hz, 2H), 1.58 (m, 4H), 1.34 (m, 4H). MS (EST) m/z 393 (M$^+$+H).

Compound 258

Methyl 4-(1H-indol-6-yl)phenyl(7-(hydroxyamino)-7-oxoheptyl)carbamate

Compound 258 (10 mg, 41%) as a yellow oil was obtained according to the same method as the synthesis of compound 180.
$^1$H NMR (400 MHz, CD$_3$OD) δ 7.64 (d, J=8.6 Hz, 1H), 7.61 (m, 1H), 7.59 (d, J=8.3 Hz, 1H), 7.28 (dd, J=8.3, 1.6 Hz, 1H), 7.25 (d, J=3.2 Hz, 1H), 7.23 (d, J=8.3 Hz, 2H), 6.45 (dd, J=3.1, 0.8 Hz, 1H), 3.67 (m, 5H), 2.05 (t, J=7.3 Hz, 2H), 1.56 (m, 4H), 1.30 (m, 4H). MS (ESI) m/z 410 (M$^+$+H).

Compound 259

7-(1-(4-(1H-indol-6-yl)phenyl)-3-(2-methoxyphenyl)ureido)-N-hydroxyheptanamide

Compound 259 (39 mg, 50%) as a yellow oil was obtained according to the same method as the synthesis of compound 255.
$^1$H NMR (400 MHz, CD$_3$OD) δ 7.99 (dd, J=7.5, 1.8 Hz, 1H), 7.77 (d, J=8.4 Hz, 2H), 7.68 (s, 1H), 7.61 (d, J=8.2 Hz, 1H), 7.30 (m, 4H), 7.06 (m, 4H), 7.06 (m, 1H), 6.87 (m, 2H), 6.77 (dd, J=7.3, 1.8 Hz, 1H), 6.46 (d, J=3.0 Hz, 1H), 3.70 (t, J=7.0 Hz, 2H), 3.52 (s, 3H), 2.06 (t, J=7.3 Hz, 2H), 1.56 (m, 4H), 1.26 (m, 4H). MS (ESI) m/z 500 (M$^+$+H).

Compound 260

7-(1-(4-(1H-indol-6-yl)phenyl)-3-(3,5-dimethoxyphenyl)ureido)-N-hydroxyheptanamide Compound 260 (35 mg, 75%) as a yellow oil was obtained according to the same method as the synthesis of compound 255.
$^1$H NMR (400 MHz, CD$_3$OD) δ 7.94 (d, J=4.3 Hz, 2H), 7.75 (s, 1H), 7.61 (d, J=8.1 Hz, 1H), 7.33 (d, J=7.8 Hz, 3H), 7.28 (s, 1H), 6.58 (s, 1H), 6.51 (s, 2H), 6.47 (s, 1H), 6.13 (s, 1H), 3.71 (m, 8H), 2.17 (t, J=7.0 Hz, 2H), 1.47 (m, 4H), 1.21 (m, 4H). MS (ESI) m/z 530 (M$^+$+H).

Compound 261

7-(N-(4-(1H-indol-6-yl)phenyl)-5-amino-2-methoxyphenylsulfonamido)-N-hydroxyheptanamide Compound 261 (53 mg, 63%) as a yellow oil was obtained according to the same method as the synthesis of compound 180.
MS (ESI) m/z 536 (M$^+$+H).

Compound 262

7-(1-(4-(1H-indol-6-yl)phenyl)-3-(thiophen-2-yl)ureido)-N-hydroxyheptanamide

Compound 262 (47 mg, 76%) as a yellow oil was obtained according to the same method as the synthesis of compound 255.

$^1$H NMR (400 MHz, CD$_3$OD) δ 7.76 (d, J=8.2 Hz, 2H), 7.68 (s, 1H), 7.62 (d, J=8.2 Hz, 1H), 7.33 (m, 3H), 7.28 (d, J=3.0 Hz, 1H), 6.79 (dd, J=5.4, 1.1 Hz, 1H), 6.73 (m, 1H), 6.51 (dd, J=3.6, 1.1 Hz, 1H), 6.46 (d, J=2.9 Hz, 1H), 3.72 (t, J=7.5 Hz, 2H), 2.07 (t, J=7.2 Hz, 2H), 1.58 (m, 4H), 1.33 (m, 4H). MS (ESI) m/z 476 (M$^+$+H).

Compound 263

7-(N-(4-(1H-indol-6-yl)phenyl)pyridine-3-sulfonamido)-N-hydroxyheptanamide

Compound 263 (29 mg, 49%) as a yellow oil was obtained according to the same method as the synthesis of compound 180.

$^1$H NMR (400 MHz, CD$_3$OD) δ 8.72 (m, 2H), 7.96 (m, 1H), 7.58 (m, 4H), 7.51 (m, 1H), 7.16 (m, 2H), 7.04 (m, 2H), 6.40 (d, J=3.1 Hz, 1H), 3.56 (t, J=5.9 Hz, 2H), 2.05 (t, J=3.1 Hz, 2H), 1.56 (m, 4H), 1.34 (m, 4H). MS (ESI) m/z 492 (M$^+$+H).

Compound 264

7-(N-(4-(1H-indol-6-yl)phenyl)methylsulfonamido)-N-hydroxyheptanamide

Compound 264 (30 mg, 43%) as a yellow oil was obtained according to the same method as the synthesis of compound 180.

$^1$H NMR (400 MHz, CD$_3$OD) δ 7.66 (d, J=8.5 Hz, 2H), 7.63 (s, 1H), 7.60 (d, J=8.2 Hz, 1H), 7.37 (d, J=8.5 Hz, 2H), 7.29 (dd, J=8.3, 1.5 Hz, 1H), 7.27 (d, J=3.1 Hz, 1H), 6.46 (d, J=3.0 Hz, 1H), 3.63 (t, J=6.8 Hz, 2H), 2.88 (s, 3H), 2.03 (t, J=7.4 Hz, 2H), 1.52 (m, 2H), 1.40 (m, 2H), 1.29 (m, 4H). MS (ESI) m/z 430 (M$^+$+H).

Compound 265

7-(N-(4-(1H-indol-6-yl)phenyl)-2-(dimethylamino)acetamido)-N-hydroxyheptanamide

Compound 265 (43 mg, 83%) as a yellow oil was obtained according to the same method as the synthesis of compound 180.

$^1$H NMR (400 MHz, CD$_3$OD) δ 7.75 (d, J=8.2 Hz, 1H), 7.67 (s, 1H), 7.62 (d, J=8.2 Hz, 1H), 7.31 (m, 4H), 6.47 (d, J=2.9 Hz, 1H), 3.71 (t, J=7.3 Hz, 2H), 3.06 (s, 2H), 2.30 (s, 6H), 2.07 (t, J=7.3 Hz, 2H), 1.55 (m, 4H), 1.33 (m, 4H). MS (ESI) m/z 438 (M$^+$+H).

Compound 266

4-methoxyphenyl 4-(1H-indol-6-yl)phenyl(7-(hydroxyamino)-7-oxoheptyl)carbamate

Compound 266 (5 mg, 20%) as a yellow oil was obtained according to the same method as the synthesis of compound 180.

$^1$H NMR (400 MHz, CD$_3$OD) δ 7.70 (d, J=8.4 Hz, 2H), 7.61 (m, 2H), 7.37 (d, J=8.5 Hz, 2H), 7.30 (dd, J=1.5, 8.3 Hz, 1H), 7.26 (d, J=3.1 Hz, 2H), 6.99 (m, 2H), 6.87 (m, 2H), 6.45 (d, J=3.0 Hz, 1H), 4.09 (m, 2H), 4.08 (s, 3H), 2.06 (m, 2H), 1.61 (m, 4H), 1.20 (m, 4H). MS (ESI) m/z 502 (M$^+$+H).

Compound 267

Ethyl 4-(1H-indol-6-yl)phenyl(7-(hydroxyamino)-7-oxoheptyl)carbamate

Compound 267 (42 mg, 32%) as a yellow oil was obtained according to the same method as the synthesis of compound 180.

$^1$H NMR (400 MHz, CD$_3$OD) δ 7.63 (m, 4H), 7.38 (m, 4H), 6.45 (s, 1H), 4.12 (q, J=6.9 Hz, 2H), 3.69 (t, J=7.1 Hz, 2H), 2.07 (t, J=7.2 Hz, 2H), 1.56 (m, 4H), 1.44 (m, 4H), 1.23 (m, 3H). MS (ESI) m/z 423 (M$^+$+H).

Compound 268

7-(1-(4-(1H-indol-6-yl)phenyl)-3,3-dimethylureido)-N-hydroxyheptanamide

Compound 268 (20 mg, 83%) as a white solid was obtained according to the same method as the synthesis of compound 255.

$^1$H NMR (400 MHz, CD$_3$OD) δ 7.65 (d, J=6.7 Hz, 2H), 7.61 (s, 1H), 7.59 (d, J=8.3 Hz, 1H), 7.28 (dd, J=8.3, 1.6 Hz, 1H), 7.25 (d, J=3.1 Hz, 1H), 7.10 (dd, J=6.7, 2.0 Hz, 2H), 6.44 (dd, J=3.1, 0.8 Hz, 1H), 3.61 (t, J=7.5 Hz, 2H), 2.69 (s, 6H), 2.06 (t, J=7.4 Hz, 2H), 1.59 (m, 4H), 1.32 (m, 4H). MS (ESI) m/z 423 (M$^+$+H).

Compound 269

2-methoxyethyl 4-(1H-indol-6-yl)phenyl(7-(hydroxyamino)-7-oxoheptyl)carbamate

Compound 269 (45 mg, 54%) as a yellow oil was obtained according to the same method as the synthesis of compound 180.

$^1$H NMR (400 MHz, CD$_3$OD) δ 7.65 (m, 4H), 7.27 (m, 4H), 6.43 (d, J=8.24 Hz, 1H), 4.22 (m, 2H), 3.71 (m, 2H), 3.54 (m, 2H), 3.30 (s, 3H), 2.07 (m, 2H), 1.60 (m, 4H), 1.34 (m, 4H). MS (ESI) m/z 454 (M$^+$+H).

Compound 270

N-(7-(hydroxyamino)-7-oxoheptyl)-N-(4-(1-methyl-1H-indazol-6-yl)phenyl)nicotinamide Compound 270 (42 mg, 72%) as a yellow oil was obtained according to the same method as the synthesis of compound 180.

$^1$H NMR (400 MHz, CD$_3$OD) δ 8.46 (s, 1H), 8.40 (d, J=4.6 Hz, 1H), 7.99 (s, 1H), 7.78 (m, 2H), 7.68 (m, 3H), 7.36 (dd, J=1.3, 8.5 Hz, 1H), 7.30 (m, 3H), 4.08 (s, 3H), 4.00 (t, J=7.3 Hz, 2H), 2.23 (t, J=7.4 Hz, 2H), 1.63 (m, 4H), 1.27 (m, 4H). MS (ESI) m/z 472 (M$^+$+H).

Compound 271

N-hydroxy-7-(4-(1-methyl-1H-indazol-6-yl)phenylamino)heptanamide

Compound 271 (36 mg, 68%) as a yellow oil was obtained according to the same method as the synthesis of compound 150.

¹H NMR (400 MHz, CD₃OD) δ 7.93 (s, 1H), 7.71 (d, J=8.4 Hz, 1H), 7.60 (s, 1H), 7.51 (d, J=8.2 Hz, 2H), 7.39 (d, J=8.4 Hz, 1H), 6.72 (d, J=8.2 Hz, 2H), 4.06 (s, 3H), 3.12 (t, J=6.9 Hz, 2H), 2.10 (t, J=7.3 Hz, 2H), 1.65 (m, 4H), 1.42 (m, 4H). MS (ESI) m/z 368 (M⁺+H).

Compound 272

7-(N-(4-(1H-indol-6-yl)phenyl)propionamido)-N-hydroxyheptanamide

Compound 272 (40 mg, 70%) as a yellow oil was obtained according to the same method as the synthesis of compound 180.
¹H NMR (400 MHz, CD₃OD) δ 7.64 (m, 4H), 7.28 (d, J=8.5 Hz, 2H), 7.16 (d, J=8.1 Hz, 2H), 6.46 (s, 1H), 3.64 (t, J=7.1 Hz, 2H), 2.03 (m, 4H), 1.47 (m, 4H), 1.26 (m, 4H), 0.99 (t, J=7.4 Hz, 3H). MS (ESI) m/z 407 (M⁺+H).

Compound 273

N-(4-(1H-indol-6-yl)phenyl)-N-(7-(hydroxyamino)-7-oxoheptyl)-1-methyl-1,2,5,6-tetrahydropyridine-3-carboxamide Compound 273 (47 mg, 74%) as a yellow oil was obtained according to the same method as the synthesis of compound 180.
¹H NMR (400 MHz, DMSO-d₆) δ 11.17 (s, 1H), 10.31 (s, 1H), 7.62 (m, 4H), 7.29 (m, 4H), 6.43 (s, 1H), 5.66 (s, 1H), 3.77 (t, J=7.4 Hz, 2H), 2.98 (S, 2H), 2.35 (t, J=5.2 Hz, 2H), 2.24 (s, 3H), 2.03 (m, 4H), 1.55 (m, 4H), 1.22 (m, 4H). MS (EST) m/z 474 (M⁺+H).

Compound 274

7-(1-(4-(1H-indol-6-yl)phenyl)-3-(pyridin-3-yl)ureido)-N-hydroxyheptanamide

Compound 274 (47 mg, 72%) as a white solid was obtained according to the same method as the synthesis of compound 255.
MS (EST) m/z 472 (M⁺+H).

Compound 275

7-(1-(4-(1H-indol-6-yl)phenyl)-3-methylureido)-N-hydroxyheptanamide

Compound 275 (40 mg, 90%) as a white solid was obtained according to the same method as the synthesis of compound 255.
¹H NMR (400 MHz, CD₃OD) δ 7.73 (d, J=8.3 Hz, 2H), 7.64 (s, 1H), 7.60 (d, J=8.2 Hz, 1H), 7.31 (dd, J=8.2, 1.0 Hz, 1H), 7.26 (m, 3H), 6.45 (d, J=3.0 Hz, 1H), 3.66 (t, J=7.4 Hz, 2H), 2.65 (s, 3H), 2.06 (t, J=7.4 Hz, 2H), 1.53 (m, 4H), 1.39 (m, 4H). MS (ESI) m/z 409 (M⁺+H).

Compound 276

7-(N-(4-(1H-indol-6-yl)phenyl)ethylsulfonamido)-N-hydroxyheptanamide

Compound 276 (44 mg, 43%) as a yellow oil was obtained according to the same method as the synthesis of compound 180.
¹H NMR (400 MHz, CD₃OD) δ 7.68 (d, J=8.4 Hz, 2H), 7.63 (s, 1H), 7.60 (d, J=8.2 Hz 1H), 7.42 (d, J=8.4 Hz, 2H), 7.30 (dd, J=8.2, 1.4 Hz, 2H), 7.27 (d, J=3.1 Hz, 2H), 6.45 (d, J=3.0 Hz, 1H), 3.72 (t, J=6.7 Hz, 2H), 3.09 (q, J=7.4 Hz, 2H), 2.06 (t, J=7.3 Hz, 2H), 1.57 (m, 2H), 1.47 (m, 2H), 1.34 (m, 7H). MS (ESI) m/z 443 (M⁺+H).

Compound 277

7-((4-(1H-indol-6-yl)phenyl)(N,N-dimethylsulfamoyl)amino)-N-hydroxyheptanamide

Compound 277 (45 mg, 58%) as a yellow oil was obtained according to the same method as the synthesis of compound 180.
¹H NMR (400 MHz, CD₃OD) δ 7.69 (d, J=8.4 Hz, 2H), 7.64 (s, 1H), 7.60 (d, J=8.2 Hz 1H), 7.45 (d, J=8.3 Hz, 2H), 7.31 (d, J=8.2 Hz, 1H), 7.27 (d, J=3.0 Hz, 1H), 6.46 (d, J=2.9 Hz, 1H), 3.67 (t, J=6.8 Hz, 2H), 2.76 (s, 6H), 2.06 (t, J=8.0 Hz, 2H), 1.58 (m, 2H), 1.48 (m, 2H), 1.36 (m, 4H). MS (ESI) m/z 458 (M⁺+H).

Compound 278

N-(4-(1H-indol-6-yl)phenyl)-N-(7-(hydroxyamino)-7-oxoheptyl)cyclohexanecarboxamide Compound 278 (46 mg, 62%) as a yellow oil was obtained according to the same method as the synthesis of compound 180.
MS (ESI) m/z 462 (M⁺+H).

Compound 279

N-(4-(1H-indol-6-yl)phenyl)-N-(7-(hydroxyamino)-7-oxoheptyl)cyclopropanecarboxamide Compound 279 (20 mg, 42%) as a yellow oil was obtained according to the same method as the synthesis of compound 180.
MS (ESI) m/z 420 (M⁺+H).

Compound 280

7-(N-(4-(1H-indol-6-yl)phenyl)-2-morpholinoacetamido)-N-hydroxyheptanamide

Compound 280 (47 mg, 79%) as a yellow oil was obtained according to the same method as the synthesis of compound 180.
MS (ESI) m/z 479 (M⁺+H).

Compound 281

(S)—N-(4-(1H-indol-6-yl)phenyl)-N-(7-(hydroxyamino)-7-oxoheptyl)pyrrolidine-2-carboxamide Compound 281 (44 mg, 84%) as a yellow oil was obtained according to the same method as the synthesis of compound 180.
¹H NMR (400 MHz, CD₃OD) δ 7.76 (d, J=8.3 Hz, 2H), 7.67 (s, 1H), 7.62 (d, J=8.2 Hz 1H), 7.30 (m, 4H), 6.46 (d, J=3.0 Hz, 1H), 3.82 (m, 1H), 3.66 (m, 2H), 3.15 (m, 1H), 2.75 (m, 1H), 2.07 (t, J=7.2 Hz, 2H), 1.89 (m, 3H), 1.74 (m, 4H), 1.53 (m, 4H), 1.33 (m, 4H). MS (ESI) m/z 448 (M⁺+H).

Compound 282

7-(1-(4-(1H-indol-6-yl)phenyl)-3-isopropylureido)-N-hydroxyheptanamide

Compound 282 (43 mg, 73%) as a white solid was obtained according to the same method as the synthesis of compound 255.
$^1$H NMR (400 MHz, CD$_3$OD) δ 7.75 (d, J=8.5 Hz, 2H), 7.65 (d, J=0.7 Hz, 1H), 7.61 (d, J=8.3 Hz, 1H), 7.32 (dd, J=8.3, 1.6 Hz, 1H), 7.28 (d, J=8.6 Hz, 2H), 7.27 (d, J=3.2 Hz, 1H), 6.45 (dd, J=3.1, 0.8 Hz, 1H), 3.88 (m, 1H), 3.66 (t, J=7.6 Hz, 2H), 2.06 (t, J=7.2 Hz, 2H), 1.59 (m, 4H), 1.32 (m, 4H), 1.05 (d, J=6.6 Hz, 6H). MS (ESI) m/z 437 (M$^+$+H).

Compound 283

7-(1-(4-(1H-indol-6-yl)phenyl)-3-isobutylureido)-N-hydroxyheptanamide

Compound 283 (45 mg, 51%) as a white solid was obtained according to the same method as the synthesis of compound 255.
$^1$H NMR (400 MHz, CD$_3$OD) δ 7.74 (d, J=8.5 Hz, 2H), 7.65 (s, 1H), 7.60 (d, J=8.2 Hz, 1H), 7.31 (dd, J=8.3, 1.6 Hz, 1H), 7.28 (d, J=7.4 Hz, 2H), 7.26 (d, J=2.1 Hz, 1H), 6.45 (dd, J=3.1, 0.8 Hz, 1H), 3.65 (t, J=7.4 Hz, 2H), 2.91 (t, J=6.7 Hz, 2H), 2.05 (t, J=7.5 Hz, 2H), 1.67 (m, 1H), 1.54 (m, 4H), 1.30 (m, 4H), 0.81 (d, J=6.7 Hz, 6H). MS (ESI) m/z 451 (M$^+$+H).

Compound 284

N-hydroxy-7-(N-(4-(1-methyl-1H-indazol-6-yl)phenyl)methylsulfonamido)heptanamide Compound 284 (44 mg, 77%) as a yellow oil was obtained according to the same method as the synthesis of compound 180.
$^1$H NMR (400 MHz, CD$_3$OD) δ 8.00 (s, 1H), 7.77 (m, 4H), 7.49 (d, J=8.2 Hz, 2H), 7.42 (d, J=8.4 Hz, 3H), 4.08 (s, 3H), 3.72 (t, J=6.6 Hz, 2H), 2.94 (s, 3H), 2.05 (t, J=7.2 Hz, 2H), 1.56 (m, 2H), 1.45 (m, 2H), 1.33 (m, 2H), 1.25 (m, 2H). MS (ESI) m/z 444 (M$^+$+H).

Compound 285

7-((4-(1H-indol-6-yl)phenyl)(propyl)amino)-N-hydroxyheptanamide

Compound 285 (34 mg, 89%) as a yellow oil was obtained according to the same method as the synthesis of compound 180.
MS (ESI) m/z 444 (M$^+$+H).

Compound 286

7-(N-(4-(1H-indol-6-yl)phenyl)-2-(4-methylpiperazin-1-yl)acetamido)-N-hydroxyheptanamide Compound 286 (56 mg, 69%) as a yellow oil was obtained according to the same method as the synthesis of compound 180.
$^1$H NMR (400 MHz, CD$_3$OD) δ 7.75 (d, J=8.4 Hz, 2H), 7.66 (s, 1H), 6.46 (d, J=2.7 Hz, 1H), 3.73 (t, J=7.4 Hz, 2H), 3.00 (s, 2H), 2.48 (m, 8H), 2.27 (s, 3H), 2.07 (t, J=7.4 Hz, 2H), 1.57 (m, 4H), 1.25 (m, 4H). MS (ESI) m/z 492 (M$^+$+H).

Compound 287

7-(1-(4-(1H-indol-6-yl)phenyl)-3-butylureido)-N-hydroxyheptanamide

Compound 287 (45 mg, 51%) as a white solid was obtained according to the same method as the synthesis of compound 255.
$^1$H NMR (400 MHz, CD$_3$OD) δ 7.73 (d, J=8.5 Hz, 2H), 7.65 (s, 1H), 7.60 (d, J=8.3 Hz, 1H), 7.31 (dd, J=8.3, 1.6 Hz, 1H), 7.27 (d, J=8.3 Hz, 2H), 7.26 (d, J=3.2 Hz, 1H), 6.45 (dd, J=3.1, 0.6 Hz, 1H), 3.65 (t, J=7.4 Hz, 2H), 3.09 (t, J=7.0 Hz, 2H), 2.06 (t, J=7.5 Hz, 2H), 1.54 (m, 4H), 1.39 (m, 4H), 1.25 (m 4H), 0.89 (t, J=7.3 Hz, 3H). MS (ESI) m/z 451 (M$^+$+H).

Compound 288

7-(1-(4-(1H-indol-6-yl)phenyl)-3-(4-methylpentyl)ureido)-N-hydroxyheptanamide

Compound 288 (46 mg, 65%) as a white solid was obtained according to the same method as the synthesis of compound 255.
$^1$H NMR (400 MHz, CD$_3$OD) δ 7.74 (d, J=8.5 Hz, 2H), 7.64 (s, 1H), 7.61 (d, J=8.3 Hz, 1H), 7.31 (dd, J=8.2, 1.6 Hz, 1H), 7.27 (d, J=8.4 Hz, 2H), 7.26 (d, J=3.1 Hz, 1H), 6.45 (dd, J=3.1, 0.8 Hz, 1H), 3.66 (t, J=7.4 Hz, 2H), 3.12 (m, 2H), 2.06 (t, J=7.5 Hz, 2H), 1.55 (m, 4H), 1.51 (m, 2H), 1.31 (m, 7H), 0.88 (d, J=6.6 Hz, 6H). MS (ESI) m/z 465 (M$^+$+H).

Compound 289

7-(1-(4-(1H-indol-6-yl)phenyl)-3-(3-(dimethylamino)propyl)ureido)-N-hydroxyheptanamide Compound 289 (49 mg, 90%) as a white solid was obtained according to the same method as the synthesis of compound 255.
$^1$H NMR (400 MHz, CD$_3$OD) δ 7.74 (d, J=8.4 Hz, 2H), 7.64 (s, 1H), 7.61 (d, J=8.6 Hz, 1H), 7.31 (dd, J=8.3, 1.6 Hz, 1H), 7.27 (d, J=8.6 Hz, 2H), 7.27 (m, 1H), 6.46 (dd, J=3.1, 0.8 Hz, 1H), 3.66 (t, J=7.4 Hz, 2H), 3.15 (t, J=6.5 Hz, 2H), 2.30 (t, J=7.1 Hz, 2H), 2.10 (s, 6H), 2.06 (t, J=7.5 Hz, 2H), 1.57 (m, 6H), 1.27 (m, 6H). MS (ESI) m/z 480 (M$^+$+H).

Compound 290

7-(1-(4-(1H-indol-6-yl)phenyl)-3-(cyclohexylmethyl)ureido)-N-hydroxyheptanamide

Compound 290 (41 mg, 94%) as a white solid was obtained according to the same method as the synthesis of compound 255.
$^1$H NMR (400 MHz, CD$_3$OD) δ 7.74 (d, J=8.4 Hz, 2H), 7.65 (s, 1H), 7.60 (d, J=8.2 Hz, 1H), 7.31 (dd, J=8.3, 1.4 Hz, 1H), 7.27 (m, 3H), 6.45 (d, J=3.0 Hz, 1H), 3.65 (t, J=7.5 Hz, 2H), 2.92 (d, J=6.9 Hz, 2H), 2.05 (t, J=7.4 Hz, 2H), 1.66 (m, 8H), 1.31 (m, 8H), 0.83 (m, 3H). MS (ESI) m/z 491 (M$^+$+H).

Compound 291

7-(N-(4-(1H-indol-6-yl)phenyl)pentanamido)-N-hydroxyheptanamide

Compound 291 (54 mg, 63%) as a yellow oil was obtained according to the same method as the synthesis of compound 180.

¹H NMR (400 MHz, CD₃OD) δ 7.73 (d, J=8.4 Hz, 2H), 7.66 (s, 1H), 7.62 (d, J=8.24 Hz, 2H), 6.46 (d, J=2.5 Hz, 1H), 3.70 (t, J=7.4 Hz, 2H), 2.15 (m, 4H), 1.56 (m, 6H), 1.31 (m, 6H), 0.80 (m, 3H). MS (ESI) m/z 436 (M⁺+H).

Compound 292

7-(N-(4-(1H-indol-6-yl)phenyl)isobutylamido)-N-hydroxyheptanamide

Compound 292 (46 mg, 79%) as a yellow oil was obtained according to the same method as the synthesis of compound 180.
¹H NMR (400 MHz, CD₃OD) δ 7.75 (d, J=8.4 Hz, 2H), 7.67 (s, 1H), 7.62 (d, J=8.2 Hz, 2H), 7.31 (m, 4H), 6.46 (d, J=2.4 Hz, 1H), 3.69 (t, J=7.5 Hz, 2H), 2.05 (m, 2H), 1.58 (m, 4H), 1.02 (s, 3H), 1.01 (s, 3H). MS (ESI) m/z 422 (M⁺+H).

Compound 293

7-(N-(4-(1H-indol-6-yl)phenyl)-2-(4-(2-methoxyethyl)piperazin-1-yl)acetamido)-N-hydroxyheptanamide Compound 293 (52 mg, 56%) as a yellow oil was obtained according to the same method as the synthesis of compound 180.
MS (ESI) m/z 536 (M⁺+H).

Compound 294

7-(1-(4-(1H-indol-6-yl)phenyl)-3,3-diethylureido)-N-hydroxyheptanamide

Compound 294 (45 mg, 51%) as a white solid was obtained according to the same method as the synthesis of compound 255.
¹H NMR (400 MHz, CD₃OD) δ 7.65 (d, J=8.6 Hz, 2H), 7.61 (t, J=0.8 Hz, 1H), 7.59 (dd, J=8.3, 0.5 Hz, 1H), 7.28 (dd, J=8.3, 1.6 Hz, 1H), 7.25 (d, J=3.2 Hz, 1H), 7.14 (d, J=8.6 Hz, 2H), 6.44 (dd, J=3.1, 0.8 Hz, 1H), 3.56 (t, J=7.5 Hz, 2H), 3.14 (q, J=7.0 Hz, 4H), 2.06 (t, J=7.5 Hz, 2H), 1.59 (m, 4H), 1.33 (m, 4H), 0.94 (t, J=7.1 Hz, 6H). MS (ESI) m/z 451 (M⁺+H).

Compound 295

7-(1-(4-(1H-indol-6-yl)phenyl)-3-ethylureido)-N-hydroxyheptanamide

Compound 295 (42 mg, 76%) as a white solid was obtained according to the same method as the synthesis of compound 255.
¹H NMR (400 MHz, CD₃OD) δ 7.71 (d, J=8.4 Hz, 2H), 7.65 (s, 1H), 7.60 (d, J=8.3 Hz, 1H), 7.30 (dd, J=8.3, 1.2 Hz, 1H), 7.25 (m, 3H), 6.45 (d, J=2.9 Hz, 1H), 3.64 (t, J=7.5 Hz, 2H), 3.14 (m, 2H), 2.05 (t, J=7.4 Hz, 2H), 1.55 (m, 4H), 1.29 (m, 4H), 1.01 (t, J=7.1 Hz, 3H). MS (ESI) m/z 423 (M⁺+H).

Compound 296

N-hydroxy-7-(N-(4-(2-methyl-1H-indol-5-yl)phenyl)methylsulfonamido)heptanamide

As shown in reaction scheme 4,6-bromo-2-methyl-1H-indole and 4-nitrophenylboronic acid were subjected to the Suzuki reaction to obtain compound 2, which was then reduced with palladium/activated carbon to obtain compound 3. Then, compound 3 is allowed to react with ethyl 7-bromoheptanoate to obtain compound 4, which was then allowed to react with methanesulfonyl chloride to obtain a compound of formula V-1, after which the compound of formula V-1 (16 mg, 0.035 mmol) was stirred with hydroxylamine and potassium hydroxide for 30 minutes. Then, a 50% water solution of hydroxylamine was added to the stirred solution until the undissolved solids were dissolved so that the solution became clear. Then, the reaction solution was stirred at mom temperature for 10 hours, and after the completion of the reaction has been confirmed, the reaction product was concentrated under reduced pressure to remove the solvent. The remaining material was extracted using ethyl acetate, washed with brine, dried with anhydrous magnesium sulfate, filtered, and concentrated under reduced pressure. The residue was crystalized, thus obtaining compound 296 (12 mg, 77.3%).
¹H NMR (400 MHz, CD₃OD) δ 7.67 (d, J=1.9 Hz, 2H), 7.65 (s, 1H), 7.41 (d, J=6.6 Hz, 2H), 7.30 (d, J=3.5 Hz, 2H), 6.17 (s, 1H), 3.71 (t, J=6.7 Hz, 2H), 2.93 (s, 3H), 2.42 (s, 3H), 2.05 (t, J=7.3 Hz, 2H), 1.57 (m, 4H), 1.31 (m, 4H). MS (ESI) m/z 443 (M⁺+H).

Compound 299

Isobutyl 4-(1H-indol-6-yl)phenyl(7-(hydroxyamino)-7-oxoheptyl)carbamate

Compound 299 (45 mg, 52%) as a yellow oil was obtained according to the same method as the synthesis of compound 180.
¹H NMR (400 MHz, CD₃OD) δ 7.63 (m, 4H), 7.28 (m, 4H), 6.45 (d, J=2.7 Hz, 1H), 3.85 (d, J=5.9 Hz, 2H), 3.67 (t, J=7.4 Hz, 2H), 1.59 (m, 4H), 1.23 (m, 4H), 0.87 (m, 6H). MS (ESI) m/z 452 (M⁺+H).

Compound 300

N-(4-(1H-indol-6-yl)phenyl)-N-(7-(hydroxyamino)-7-oxoheptyl)thiophene-2-carboxamide Compound 300 (26 mg, 64%) as a yellow oil was obtained according to the same method as the synthesis of compound 180.
¹H NMR (400 MHz, CD₃OD) δ 7.70 (d, J=8.4 Hz, 2H), 7.66 (s, 1H), 7.61 (d, J=8.2 Hz, 2H), 7.43 (d, J=4.7 Hz, 1H), 7.32 (d, J=8.5 Hz, 1H), 7.27 (m, 3H), 6.81 (m, 2H), 6.46 (d, J=3.0 Hz, 1H), 3.65 (t, J=7.4 Hz, 2H), 2.06 (m, 2H), 1.63 (m, 4H), 1.30 (m, 4H). MS (ESI) m/z 462 (M⁺+H).

Compound 302

N-(7-(hydroxyamino)-7-oxoheptyl)-N-(4-(1-methyl-1H-indazol-6-yl)phenyl)picolinamide Compound 302 (47 mg, 71%) as a yellow oil was obtained according to the same method as the synthesis of compound 180.
¹H NMR (400 MHz, CD₃OD) δ 8.37 (s, 1H), 7.98 (s, 1H), 7.77 (d, J=8.4 Hz, 2H), 7.66 (m, 3H), 7.35 (m, 5H), 4.07 (s, 3H), 3.69 (t, J=7.1 Hz, 2H), 2.07 (t, J=7.2 Hz, 2H), 1.56 (m, 4H), 1.44 (m, 4H). MS (ESI) m/z 471 (M⁺+H).

Compound 303

7-(N-(4-(1H-indol-5-yl)phenyl)methylsulfonamido)-N-hydroxyheptanamide

Compound 303 (42 mg, 92%) as a yellow oil was obtained according to the same method as the synthesis of compound 180.

¹H NMR (400 MHz, CD₃OD) δ 7.81 (t, J=1.3 Hz, 1H), 7.67 (m, 2H), 7.45 (d, J=4.3 Hz, 1H), 7.39 (m, 3H), 7.28 (d, J=3.1 Hz, 1H), 6.51 (t, J=3.2 Hz, 1H), 3.66 (t, J=6.6 Hz, 2H), 2.91 (s, 3H), 2.06 (t, J=7.3 Hz, 2H), 1.56 (m, 2H), 1.44 (m, 2H), 1.33 (m, 2H), 1.29 (m, 2H). MS (ESI) m/z 429 (M⁺+H).

Compound 304

N-(4-(1H-indol-6-yl)phenyl)-N-(7-(hydroxyamino)-7-oxoheptyl)-1-methylpiperidine-4-carboxamide Compound 304 (47 mg, 77%) as a yellow oil was obtained according to the same method as the synthesis of compound 180.
¹H NMR (400 MHz, CD₃OD) δ 7.78 (d, J=8.4 Hz, 2H), 7.67 (s, 1H), 7.62 (d, J=8.2 Hz, 1H), 7.33 (m, 1H), 7.31 (d, J=8.4 Hz, 2H), 7.28 (d, J=3.1 Hz, 1H), 6.46 (d, J=2.4 Hz, 1H), 3.70 (t, J=7.7 Hz, 2H), 2.94 (d, J=11.5 Hz, 2H), 2.38 (m, 1H), 2.28 (s, 3H), 2.06 (t, J=7.3 Hz, 2H), 1.50 (m, 6H), 1.20 (m, 8H). MS (ESI) m/z 477 (M⁺+H).

Compound 305

N-(4-(1H-indol-5-yl)phenyl)-N-(7-(hydroxyamino)-7-ooxheptyl)picolinamide

Compound 305 (45 mg, 66%) as a yellow oil was obtained according to the same method as the synthesis of compound 180.
¹H NMR (400 MHz, CD₃OD) δ 8.85 (d, J=3.8 Hz, 1H), 7.65 (m, 2H), 7.47 (d, J=7.9 Hz, 2H), 7.41 (d, J=8.4 Hz, 1H), 7.33 (d, J=7.6 Hz, 1H), 7.22 (m, 3H), 7.10 (d, J=8.0 Hz, 2H), 6.47 (d, J=2.5 Hz, 1H), 3.96 (t, J=6.9 Hz, 2H), 2.08 (t, J=7.2 Hz, 2H), 1.62 (m, 4H), 1.33 (m, 4H). MS (ESI) m/z 456 (M⁺+H).

Compound 306

N-(4-(1H-indol-6-yl)phenyl)-N-(7-(hydroxyamino)-7-oxoheptyl)morpholine-4-carboxamide Compound 306 (43 mg, 65%) as a white solid was obtained according to the same method as the synthesis of compound 255.
¹H NMR (400 MHz, DMSO-d₆) δ 11.13 (s, 1H), 10.29 (s, 1H), 8.63 (s, 1H), 7.64 (d, J=6.5 Hz, 2H), 7.60 (s, 1H), 7.57 (d, J=8.2 Hz, 2H), 7.35 (m, 1H), 7.28 (dd, J=8.2, 1.4 Hz, 1H), 7.16 (d, J=8.5 Hz, 2H), 6.41 (s, 1H), 3.54 (t, J=7.6 Hz, 2H), 3.38 (m, 4H), 3.08 (m, 4H), 1.89 (t, J=7.2 Hz, 2H), 1.47 (m, 4H), 1.22 (m, 4H). MS (EST) m/z 465 (M⁺+H).

Compound 307

7-(N-(4-(1,2-dimethyl-1H-indol-5-yl)phenyl)methyl-sulfonamido)-N-hydroxyheptanamide Compound 307 (90 mg, 93%) as a white solid was obtained according to the same method as the synthesis of compound 296.
¹H NMR (400 MHz, CD₃OD) δ 7.69 (m, 3H), 7.41 (m, 4H), 6.25 (s, 1H), 3.58 (m, 5H), 2.95 (s, 3H), 2.39 (s, 3H), 1.88 (t, J=6.9 Hz, 2H), 1.46 (m, 4H), 1.16 (m, 4H). MS (EST) m/z 458 (M⁺+H).

Compound 309

N-(4-(1H-indol-6-yl)phenyl)-N-(7-(hydroxyamino)-7-oxoheptyl)-4-methylpiperazine-1-carboxamide Compound 309 (47 mg, 78%) as a white solid was obtained according to the same method as the synthesis of compound 255.
¹H NMR (400 MHz, DMSO-d₆) δ 11.13 (s, 1H), 10.30 (s, 1H), 8.63 (s, 1H), 7.63 (d, J=6.5 Hz, 2H), 7.60 (s, 1H), 7.57 (d, J=8.3 Hz, 1H), 7.35 (t, J=2.6 Hz, 1H), 7.28 (dd, J=8.3, 1.3 Hz, 1H), 7.12 (d, J=8.5 Hz, 2H), 6.41 (s, 1H), 3.52 (t, J=7.2 Hz, 2H), 3.09 (s, 4H), 2.09 (s, 4H), 2.05 (s, 3H), 1.90 (t, J=7.3 Hz, 2H), 1.45 (m, 4H), 1.22 (m, 4H). MS (ESI) m/z 478 (M⁺+H).

Compound 310

N-hydroxy-7-(N-(4-(1-methyl-1H-indazol-6-yl)phenyl)ethylsulfonamido)heptanamide

Compound 310 (45 mg, 85%) as a yellow oil was obtained according to the same method as the synthesis of compound 180.
¹H NMR (400 MHz, CD₃OD) δ 8.00 (s, 1H), 7.78 (m, 4H), 7.52 (d, J=7.4 Hz, 1H), 7.50 (d, J=8.4 Hz, 1H), 7.44 (d, J=8.4 Hz, 1H), 4.09 (s, 3H), 3.76 (t, J=6.6 Hz, 2H), 3.12 (q, J=8.4 Hz, 2H), 2.06 (t, J=7.3 Hz, 2H), 1.59 (m, 2H), 1.47 (m, 2H), 1.27 (m, 7H). MS (ESI) m/z 458 (M⁺+H).

Compound 311

N-(4-(1H-indol-5-yl)phenyl)-N-(7-(hydroxyamino)-7-oxoheptyl)nicotinamide

Compound 311 (45 mg, 65%) as a yellow oil was obtained according to the same method as the synthesis of compound 180.
¹H NMR (400 MHz, CD₃OD) δ 8.45 (s, 1H), 8.38 (d, J=3.4 Hz, 1H), 7.75 (d, J=7.7 Hz, 1H), 7.72 (s, 1H), 7.55 (d, J=8.2 Hz, 2H), 7.42 (d, J=8.4 Hz, 1H), 7.30 (d, J=8.6 Hz, 2H), 7.25 (d, J=3.1 Hz, 1H), 7.15 (d, J=8.0 Hz, 2H), 6.48 (d, J=3.0 Hz, 1H), 3.95 (t, J=6.9 Hz, 2H), 2.08 (t, J=7.3 Hz, 2H), 1.59 (m, 4H), 1.37 (m, 4H). MS (ESI) m/z 456 (M⁺+H).

Compound 312

N-(7-(hydroxyamino)-7-oxoheptyl)-4-methyl-N-(4-(1-methyl-1H-indazol-6-yl)phenyl)piperazine-1-carboxamide Compound 312 (42 mg, 93%) as a yellow oil was obtained according to the same method as the synthesis of compound 255.
¹H NMR (400 MHz, CD₃OD) δ 7.99 (s, 1H), 7.80 (d, J=8.4 Hz, 1H), 7.76 (d, J=8.2 Hz, 2H), 7.75 (s, 1H), 7.45 (dd, J=8.5, 1.2 Hz, 1H), 7.23 (d, J=8.5 Hz, 2H), 4.10 (s, 3H), 3.66 (t, J=7.6 Hz, 2H), 3.24 (m, 4H), 2.27 (t, J=4.5 Hz, 4H), 2.21 (s, 3H), 2.06 (t, J=7.3 Hz, 2H), 1.42 (m, 4H), 1.28 (m, 4H). MS (ESI) m/z 493 (M⁺+H).

Compound 313

N-(4-(1H-indol-5-yl)phenyl)-N-(7-(hydroxyamino)-7-oxoheptyl)-4-methylpiperazine-1-carboxamide Compound 313 (47 mg, 78%) as a yellow oil was obtained according to the same method as the synthesis of compound 255.

¹H NMR (400 MHz, CD₃OD) δ 7.78 (s, 1H), 7.65 (d, J=8.6 Hz, 2H), 744 (d, J=8.5 Hz, 1H), 7.37 (dd, J=8.5, 1.7 Hz, 1H), 7.25 (d, J=3.1 Hz, 1H), 7.15 (d, J=8.5 Hz, 2H), 6.49 (dd, J=3.1, 0.7 Hz, 1H), 3.63 (t, J=7.5 Hz, 2H), 3.21 (m, 4H), 2.24 (t, J=4.7 Hz, 4H), 2.19 (s, 3H), 2.06 (t, J=7.4 Hz, 2H), 1.58 (m, 4H), 1.28 (m, 4H). MS (ESI) m/z 478 (M⁺+H).

Compound 314

7-(N-(4-(1H-indol-5-yl)phenyl)ethylsulfonamido)-N-hydroxyheptanamide

Compound 314 (44 mg, 43%) as a yellow oil was obtained according to the same method as the synthesis of compound 180.
¹H NMR (400 MHz, CD₃OD) δ 7.81 (s, 1H), 7.67 (d, J=8.4 Hz, 2H), 7.46 (d, J=8.4 Hz, 1H), 7.40 (m, 3H), 7.27 (d, J=3.0 Hz, 1H), 6.51 (d, J=2.9 Hz, 1H), 3.71 (t, J=6.6 Hz, 2H), 3.07 (q, J=7.4 Hz, 2H), 2.05 (t, J=7.3 Hz, 2H), 1.56 (m, 2H), 1.43 (m, 2H), 1.30 (m, 7H). MS (ESI) m/z 443 (M⁺+H).

Compound 315

N-(7-(hydroxyamino)-7-oxoheptyl)-N-(4-(1-methyl-1H-indazol-6-yl)phenyl)morpholine-4-carboxamide Compound 315 (9 mg, 40%) as a yellow oil was obtained according to the same method as the synthesis of compound 255.
¹H NMR (400 MHz, CD₃OD) δ 7.99 (s, 1H), 7.80 (d, J=8.6 Hz, 1H), 7.72 (d, J=6.9 Hz, 2H), 7.71 (s, 1H), 744 (dd, J=8.5, 1.2 Hz, 1H), 7.24 (d, J=8.5 Hz, 2H), 4.09 (s, 3H), 3.66 (t, J=7.4 Hz, 2H), 3.47 (m, 4H), 3.20 (m, 4H), 2.06 (t, J=7.3 Hz, 2H), 1.58 (m, 4H), 1.26 (m, 4H). MS (ESI) m/z 480 (M⁺+H).

Compound 316

N-(4-(1H-indol-5-yl)phenyl)-N-(7-(hydroxyamino)-7-oxoheptyl)morpholine-4-carboxamide Compound 316 (45 mg, 65%) as a yellow oil was obtained according to the same method as the synthesis of compound 255.
¹H NMR (400 MHz, CD₃OD) δ 7.78 (d, J=1.2 Hz, 1H), 7.65 (d, J=8.4 Hz, 2H), 7.44 (d, J=8.4 Hz, 1H), 7.37 (d, J=8.4 Hz, 1H), 7.25 (d, J=2.9 Hz, 1H), 7.15 (d, J=8.4 Hz, 2H), 6.49 (d, J=2.8 Hz, 1H), 3.62 (t, J=7.4 Hz, 2H), 3A4 (m, 4H), 3.17 (m, 4H), 2.06 (t, J=7.4 Hz, 2H), 1.57 (m, 4H), 1.27 (m, 4H). MS (ESI) m/z 465 (M⁺+H).

Compound 317

N-(4-(1H-indol-6-yl)phenyl)-N-(7-(hydroxyamino)-7-oxoheptyl)-2,6-dimethylmorpholine-4-carboxamide Compound 317 (43 mg, 86%) as a white solid was obtained according to the same method as the synthesis of compound 255.
¹H NMR (400 MHz, CD₃OD) δ 7.67 (d, J=8.4 Hz, 2H), 7.62 (s, 1H), 7.60 (d, J=8.3 Hz, 1H), 7.29 (dd, J=8.3, 1.2 Hz, 1H), 7.26 (d, J=3.1 Hz, 1H), 7.16 (d, J=8.4 Hz, 2H), 6.45 (d, J=3.0 Hz, 1H), 3.65 (m, 4H), 3.41 (m, 2H), 2.31 (m, 2H), 2.06 (t, J=7.4 Hz, 2H), 1.58 (m, 4H), 1.17 (m, 4H). MS (ESI) m/z 493 (M⁺+H).

Compound 318

N-(7-(hydroxyamino)-7-oxoheptyl)-2,6-dimethyl-N-(4-(1-methyl-1H-indazol-6-yl)phenyl)morpholine-4-carboxamide Compound 318 (50 mg, 80%) as a yellow oil was obtained according to the same method as the synthesis of compound 255.
¹H NMR (400 MHz, CD₃OD) δ 7.99 (s, 1H), 7.80 (d, J=8.5 Hz, 1H), 7.76 (m, 3H), 7.44 (dd, J=8.5, 1.1 Hz, 1H), 7.22 (d, J=8.51 Hz, 2H), 4.09 (s, 3H), 3.67 (m, 4H), 3.41 (m, 2H), 2.32 (m, 2H), 2.06 (t, J=7.3 Hz, 2H), 1.58 (m, 4H), 1.27 (m, 4H), 0.98 (d, J=6.2 Hz, 6H). MS (ESI) m/z 508 (M⁺+H).

Compound 319

N-(4-(1H-indol-5-yl)phenyl)-N-(7-(hydroxyamino)-7-oxoheptyl)-2,6-dimethylmorpholine-4-carboxamide Compound 319 (49 mg, 39%) as a yellow oil was obtained according to the same method as the synthesis of compound 255.
¹H NMR (400 MHz, CD₃OD) δ 7.79 (d, J=1.1 Hz, 1H), 7.66 (d, J=8.4 Hz, 2H), 7.44 (d, J=8.4 Hz, 1H), 7.37 (dd, J=8.4, 1.3 Hz, 1H), 7.25 (d, J=3.0 Hz, 1H), 7.15 (d, J=8.4 Hz, 2H), 6.49 (d, J=2.9 Hz, 1H), 3.61 (m, 4H), 3.40 (m, 2H), 2.06 (m, 2H), 1.58 (m, 4H), 1.19 (m, 4H), 0.97 (d, J=6.2 Hz, 6H). MS (ESI) m/z 493 (M⁺+H).

Compound 320

N-hydroxy-7-(N-(4-(1-methyl-1H-indol-5-yl)phenyl)methylsulfonamido)heptanamide

As shown in reaction scheme 5,4-bromoaniline and methanesulfonyl chloride were reacted with each other to obtain compound 6, which was then allowed to react with ethyl 7-bromoheptanoate to obtain compound 7. Then, compound 7 was subjected to the Suzuki reaction to obtain a compound of formula XII, after which the compound of formula XII was methylated on the indole ring, and then stirred with hydroxylamine and potassium hydroxide for 30 minutes. Then, a 50% water solution of hydroxylamine was added to the stirred solution until the undissolved solids were dissolved so that the solution became clear. Then, the reaction solution was stirred at mom temperature for 10 hours, and after the completion of the reaction has been confirmed, the reaction product was concentrated under reduced pressure to remove the solvent. The remaining material was extracted using ethyl acetate, washed with brine, dried with anhydrous magnesium sulfate, filtered, and concentrated under reduced pressure. The residue was crystallized, thus obtaining compound 320 (3 mg, 61%).
MS (ESI) m/z 444 (M⁺+H).

Compound 321

N-hydroxy-7-(N-(4-(1-methyl-1H-indol-6-yl)phenyl)methylsulfonamido)heptanamide

Compound 321 (8 mg, 69%) as a white solid was obtained according to the same method as the synthesis of compound 320.
MS (ESI) m/z 444 (M⁺+H).

Compound 323

N-(4-(1H-indol-6-yl)phenyl)-N-(7-(hydroxyamino)-7-oxoheptyl)-4-isopropylpiperazine-1-carboxamide Compound 323 (50 mg, 79%) as a white solid was obtained according to the same method as the synthesis of compound 255.
$^1$H NMR (400 MHz, CD$_3$OD) δ 7.69 (d, J=8.4 Hz, 2H), 7.62 (m, 2H), 7.30 (dd, J=8.2, 1.4 Hz, 1H), 7.27 (d, J=3.0 Hz, 1H), 7.19 (d, J=4.6, 2H), 6.46 (d, J=2.9 Hz, 1H), 3.68 (t, J=7.2 Hz, 2H), 3.28 (m, 5H), 2.44 (m, 4H), 2.08 (t, J=7.2 Hz, 2H), 1.62 (m, 4H), 1.34 (m, 4H), 1.23 (m, 3H), 0.90 (m, 3H). MS (ESI) m/z 505 (M$^+$+H).

Compound 324

N-(4-(1H-indol-6-yl)phenyl)-N-(7-(hydroxyamino)-7-oxoheptyl)pyrrolidine-1-carboxamide Compound 324 (44 mg, 84%) as a white solid was obtained according to the same method as the synthesis of compound 255.
$^1$H NMR (400 MHz, CD$_3$OD) δ 7.67 (s, 1H), 7.65 (d, J=4.2 Hz, 2H), 7.60 (d, J=8.2 Hz, 1H), 7.30 (dd, J=8.2, 1.4 Hz, 1H), 7.27 (d, J=3.1 Hz, 1H), 7.15 (m, J=8.4 Hz 2H), 6.46 (d, J=2.4 Hz, 1H), 3.62 (t, J=7.4 Hz, 2H), 3.05 (m, 4H), 2.06 (t, J=7.2 Hz, 2H), 1.69 (m, 4H), 1.59 (m, 4H), 1.31 (m, 4H). MS (ESI) m/z 448 (M$^+$+H).

Compound 325

N-(4-(1H-indol-5-yl)phenyl)-N-(7-(hydroxyamino)-7-oxoheptyl)isonicotinamide

Compound 325 (45 mg, 57%) as a yellow oil was obtained according to the same method as the synthesis of compound 180.
MS (ESI) m/z 457 (M$^+$+H).

Compound 326

7-(N-(6-(1H-indol-6-yl)pyridin-3-yl)methylsulfonamido)-N-hydroxyheptanamide

Compound 326 (34 mg, 84%) as a yellow oil was obtained according to the same method as the synthesis of compound 252.
$^1$H NMR (400 MHz, CD$_3$OD) δ 8.57 (d, J=1.7 Hz, 1H), 8.06 (s, 1H), 7.91 (d, J=8.4 Hz, 1H), 7.85 (d, J=6.6 Hz, 1H), 7.65 (m, 2H), 7.34 (d, J=2.6 Hz, 1H), 6.50 (d, J=2.6 Hz, 1H), 3.72 (t, J=6.7 Hz, 2H), 2.97 (s, 3H), 2.05 (t, J=7.3 Hz, 2H), 1.56 (m, 4H), 1.33 (m, 4H). MS (ESI) m/z 430 (M$^+$+H).

Compound 327

N-hydroxy-7-(N-(6-(1-methyl-1H-indazol-6-yl)pyridin-3-yl)methylsulfonamido)heptanamide Compound 327 (44 mg, 64%) as a yellow oil was obtained according to the same method as the synthesis of compound 252.
$^1$H NMR (400 MHz, DMSO-d$_6$) δ 10.31 (s, 1H), 8.67 (d, J=2.2 Hz, 1H), 8.64 (s, 1H), 8.36 (s, 1H), 8.18 (d, J=8.4 Hz, 1H), 8.00 (s, 1H), 7.99 (dd, J=8.4, 2.2 Hz, 1H), 7.90 (d, J=7.3 Hz, 1H), 7.85 (d, J=8.4 Hz, 1H), 4.12 (s, 3H), 3.71 (t, J=6.6 Hz, 2H), 3.05 (s, 3H), 1.89 (t, J=7.3 Hz, 2H), 1.39 (m, 4H), 1.18 (m, 4H). MS (ESI) m/z 445 (M$^+$+H).

Compound 328

7-(N-(6-(1H-indol-5-yl)pyridin-3-yl)methylsulfonamido)-N-hydroxyheptanamide

Compound 328 (29 mg, 91%) as a yellow oil was obtained according to the same method as the synthesis of compound 252.
$^1$H NMR (400 MHz, CD$_3$OD) δ 8.56 (d, J=2.0 Hz, 1H), 8.20 (d, J=1.2 Hz, 1H), 7.88 (d, J=6.4 Hz, 1H), 7.84 (d, J=6.0 Hz, 1H), 7.76 (d, J=6.8 Hz, 1H), 7.49 (d, J=8.5 Hz, 1H), 7.30 (d, J=3.1 Hz, 1H), 6.57 (d, J=2.6 Hz, 1H), 3.72 (t, J=6.8 Hz, 2H), 2.97 (s, 3H), 2.05 (t, J=7.3 Hz, 2H), 1.56 (m, 4H), 1.33 (m, 4H). MS (ESI) m/z 430 (M$^+$+H).

Compound 329

N-(4-(1H-indol-6-yl)phenyl)-4-acetyl-N-(7-(hydroxyamino)-7-oxoheptyl)piperazine-1-carboxamide Compound 329 (50 mg, 60%) as a white solid was obtained according to the same method as the synthesis of compound 255.
$^1$H NMR (400 MHz, DMSO-d$_6$) δ 7.69 (d, J=8.6 Hz, 2H), 7.62 (s, 1H), 7.59 (d, J=8.3 Hz, 1H), 7.29 (dd, J=8.2, 1.5 Hz, 1H), 7.26 (d, J=3.1 Hz, 1H), 7.22 (d, J=8.6 Hz, 2H), 6.44 (m, 1H), 3.66 (t, J=7.5 Hz, 2H), 3.37 (m, 4H), 3.25 (m, 4H), 2.06 (t, J=7.4 Hz, 2H), 2.01 (s, 3H), 1.59 (m, 4H), 1.28 (m, 4H). MS (EST) m/z 506 (M$^+$+H).

Compound 330

N-(4-(1H-indol-6-yl)phenyl)-N-(7-(hydroxyamino)-7-oxoheptyl)-4-methyl-1,4-diazepane-1-carboxamide Compound 330 (49 mg, 92%) as a white solid was obtained according to the same method as the synthesis of compound 255.
$^1$H NMR (400 MHz, DMSO-d$_6$) δ 7.66-7.58 (m, 4H), 7.29-7.25 (m, 2H), 7.11 (d, J=8.6 Hz, 2H), 644 (d, J=3.1 Hz, 1H), 3.61 (t, J=7.4 Hz, 2H), 3.35 (m, 2H), 3.18 (t, J=6.0 Hz, 2H), 2.59 (m, 2H), 2.53 (m, 2H), 2.30 (s, 3H), 2.07 (t, J=7.3 Hz, 2H), 1.76 (m, 2H), 1.61 (m, 4H), 1.33 (m, 4H). MS (ESI) m/z 492 (M$^+$+H).

Compound 331

N-(7-(hydroxyamino)-7-oxoheptyl)-4-methyl-N-(4-(1-methyl-1H-indol-6-yl)phenyl)piperazine-1-carboxamide As shown in reaction scheme 6,4-bromoaniline and ethyl 7-bromoheptanoate were allowed to react with each other so as to obtain compound 9, which was then allowed to react with 4-nitrophenyl chloroformate so as to obtain compound 10. Then, compound 10 was subjected to the Suzuki reaction with boronic acid to obtain a compound of formula VII-1, which was then methylated on the indole ring and allowed to react with 4-methylpiperazine, thus obtaining a compound of formula VIII-1. Then, the compound of formula VIII-1 (201 mg, 0.398 mmol) was stirred with hydroxylamine and potassium hydroxide for 30 minutes. Then, a 50% water solution of hydroxylamine was added to the stirred solution until the undissolved solids were dissolved so that the solution became clear. Then, the reaction solution was stirred at mom temperature for 10 hours, and after the completion of the reaction has been confirmed, the reaction product was concentrated under reduced pressure to remove the solvent. The remaining material was extracted using ethyl acetate, washed with brine, dried with anhydrous magnesium sulfate, filtered, and concentrated under reduced pressure. The residue was crystallized, thus obtaining compound 331 (106 mg 54%).

$^1$H NMR (400 MHz, DMSO-$d_6$) δ 7.72 (d, J=8.6 Hz, 2H), 7.60-7.58 (m, 2H), 7.32 (d, J=8.3 Hz, 1H), 7.19-7.17 (m, 3H), 6.43 (d, J=3.1 Hz, 1H), 3.84 (s, 3H), 3.64 (t, J=7.4 Hz, 2H), 3.24 (m, 4H), 2.26 (m, 4H), 2.20 (s, 3H), 2.06 (t, J=7.4 Hz, 2H), 1.59 (m, 4H), 1.35 (m, 4H). MS (ESI) m/z 492 (M$^+$+H).

Compound 332

7-(N-(4-(1H-indol-2-yl)phenyl)methylsulfonamido)-N-hydroxyheptanamide

Compound 332 (29 mg, 44%) as a yellow oil was obtained according to the same method as the synthesis of compound 252.
MS (ESI) m/z 429 (M$^+$+H).

Compound 333

Tert-butyl 2-(4-(N-(7-(hydroxyamino)-7-oxoheptyl)methylsulfonamido)phenyl)-1H-indole-1-carboxylate Compound 333 (52 mg, 24%) as a yellow oil was obtained according to the same method as the synthesis of compound 252.
MS (ESI) m/z 529 (M$^+$+H).

Compound 334

N-(7-(hydroxyamino)-7-oxoheptyl)-4-methyl-N-(4-(2-methyl-1H-indol-5-yl)phenyl)piperazine-1-carboxamide Compound 334 (235 mg, 97%) as a white solid was obtained according to the same method as the synthesis of compound 296.
$^1$H NMR (400 MHz, DMSO-$d_6$) δ 7.64-7.62 (m, 3H), 7.32-7.30 (m, 2H), 7.15 (d, J=6.7 Hz, 2H), 6.16 (s, 1H), 3.63 (t, J=7.5 Hz, 2H), 3.23 (m, 4H), 2.42 (s, 3H), 2.25 (m, 4H), 2.20 (s, 3H), 2.06 (t, J=7.4 Hz, 2H), 1.59 (m, 4H), 1.32 (m, 4H). MS (ESI) m/z 493 (M$^+$+H).

Compound 335

N-(4-(1H-indol-6-yl)phenyl)-4-benzyl-N-(7-(hydroxyamino)-7-oxoheptyl)piperazine-1-carboxamide Compound 335 (5 mg, 54%) as a white solid was obtained according to the same method as the synthesis of compound 255.
$^1$H NMR (400 MHz, CD$_3$OD) δ 7.64 (d, J=8.6 Hz, 2H), 7.61 (m, 2H), 7.29 (dd, J=8.3, 1.6 Hz, 1H), 7.23 (m, 6H), 7.13 (d, J=8.6 Hz, 2H), 6.45 (dd, J=3.1, 0.8 Hz, 1H), 3.61 (t, J=7.5 Hz, 2H), 3.43 (s, 2H), 3.21 (m, 4H), 2.25 (t, J=4.8 Hz, 4H), 2.05 (t, J=7.5 Hz, 2H), 1.58 (m, 4H), 1.31 (m, 4H). MS (ESI) m/z 554 (M$^+$+H).

Compound 336

4-ethyl-N-(7-(hydroxyamino)-7-oxoheptyl)-N-(4-(1-methyl-1H-indazol-6-yl)phenyl)piperazine-1-carboxamide Compound 336 (39 mg, 70%) as a yellow oil was obtained according to the same method as the synthesis of compound 255.
$^1$H NMR (400 MHz, CD$_3$OD) δ 8.00 (d, J=0.9 Hz, 1H), 7.80 (dd, J=8.4, 0.6 Hz, 1H), 7.76 (m, 3H), 7.45 (dd, J=8.5, 1.4 Hz, 1H), 7.23 (d, J=8.6 Hz, 2H), 4.10 (s, 3H), 3.66 (t, J=7.5 Hz, 2H), 3.26 (m, 4H), 2.37 (q, J=7.2 Hz, 2H), 2.31 (m, 4H), 2.06 (t, J=7.4 Hz, 2H), 1.60 (m, 4H), 1.32 (m, 4H), 1.03 (t, J=7.2 Hz, 3H). MS (ESI) m/z 507 (M$^+$+H).

Compound 337

7-(N-(4-(5-bromo-1H-indol-2-yl)phenyl)methylsulfonamido)-N-hydroxyheptanamide

Compound 337 (45 mg, 70%) as a yellow oil was obtained according to the same method as the synthesis of compound 252.
MS (ESI) m/z 507 (M$^+$+H).

Compound 338

Tert-butyl 5-bromo-2-(4-(N-(7-(hydroxyamino)-7-oxoheptyl)methylsulfonamido)phenyl)-1H-indazole-1-carboxylate Compound 338 (60 mg, 70%) as a yellow oil was obtained according to the same method as the synthesis of compound 252.
MS (ESI) m/z 607 (M$^+$+H).

Compound 339

N-(4-(1H-indol-6-yl)phenyl)-4-ethyl-N-(7-(hydroxyamino)-7-oxoheptyl)piperazine-1-carboxamide Compound 339 (29 mg, 49%) as a white solid was obtained according to the same method as the synthesis of compound 255.
$^1$H NMR (400 MHz, CD$_3$OD) δ 7.55 (m, 5H), 7.29 (d, J=7.9 Hz, 1H), 7.26 (s, 1H), 7.16 (d, J=6.7 Hz, 1H), 6.44 (m, 1H), 3.63 (t, J=7.0 Hz, 2H), 3.24 (m, 4H), 2.35 (m, 2H), 2.29 (m, 4H), 2.15 (t, J=7.2 Hz, 2H), 1.58 (m, 4H), 1.28 (m, 4H), 1.02 (t, J=6.8 Hz, 3H). MS (ESI) m/z 492 (M$^+$+H).

Compound 340

N-(4-(1H-indol-5-yl)phenyl)-4-ethyl-N-(7-(hydroxyamino)-7-oxoheptyl)piperazine-1-carboxamide Compound 340 (42 mg, 90%) as a yellow oil was obtained according to the same method as the synthesis of compound 255.
$^1$H NMR (400 MHz, CD$_3$OD) δ 7.78 (s, 1H), 7.66 (d, J=7.5 Hz, 2H), 7.56 (m, 2H), 7.43 (m, 1H), 7.25 (m, 1H), 7.16 (d, J=7.4 Hz, 2H), 6.49 (s, 1H), 3.63 (t, J=6.6 Hz, 2H), 3.25 (m, 4H), 2.36 (m, 2H), 2.30 (m, 4H), 2.06 (m, 2H), 1.58 (m, 4H), 1.27 (m, 4H), 1.02 (t, J=6.8 Hz, 3H)). MS (ESI) m/z 492 (M$^+$+H).

Compound 341

N-(7-(hydroxyamino)-7-oxoheptyl)-4-methyl-N-(4-(1-methyl-1H-indol-5-yl)phenyl)piperazine-1-carboxamide Compound 341 (7 mg, 77%) as a yellow oil was obtained according to the same method as the synthesis of compound 331.

$^1$H NMR (400 MHz, DMSO-d$_6$) δ 7.78 (s, 1H), 7.67 (d, J=6.6 Hz, 2H), 7.44 (s, 2H), 7.18-7.16 (m, 3H), 6.48 (d, J=3.1 Hz, 1H), 3.82 (s, 3H), 3.64 (t, J=7.4 Hz, 2H), 3.25 (m, 4H), 2.26 (m, 4H), 2.21 (s, 3H), 2.06 (t, J=7.4 Hz, 2H), 1.60 (m, 4H), 1.33 (m, 4H). MS (ESI) m/z 492 (M$^+$+H).

Compound 342

N-hydroxy-7-(4-methyl-N-(4-(1-methyl-1H-indazol-6-yl)phenyl)piperazine-1-sulfonamido)heptanamide Compound 342 (0.4 g, 42%) as a yellow oil was obtained according to the same method as the synthesis of compound 180.

$^1$H NMR (400 MHz, CD$_3$OD) δ 7.99 (s, 1H), 7.79 (d, J=8.4 Hz, 1H), 7.75 (d, J=8.3 Hz, 2H), 7.74 (s, 1H), 7.51 (d, J=8.4 Hz, 2H), 7.42 (d, J=8.4 Hz, 1H), 4.08 (s, 3H), 3.70 (t, J=6.9 Hz, 2H), 3.23 (t, J=4.8 Hz, 4H), 2.40 (t, J=4.6 Hz, 4H), 2.24 (s, 3H), 2.05 (t, J=7.4 Hz, 2H), 1.52 (m, 2H), 1.44 (m, 2H), 1.32 (m, 4H). MS (ESI) m/z 529 (M$^+$+H).

Compound 343

N-(4-(1H-indol-6-yl)phenyl)-N-(7-(hydroxyamino)-7-oxoheptyl)-4-(2-methoxyphenyl)piperazine-1-carboxamide Compound 343 (30 mg, 76%) as a yellow liquid was obtained according to the same method as the synthesis of compound 255.

$^1$H NMR (400 MHz, CD$_3$OD) δ 7.95 (s, 1H), 7.65 (d, J=8.5 Hz, 2H), 7.62 (s, 1H), 7.58 (d, J=8.3 Hz, 1H), 7.28 (dd, J=8.3, 1.2 Hz, 1H), 7.24 (d, J=3.1 Hz, 1H), 7.14 (d, J=8.5 Hz, 2H), 6.44 (d, J=2.9 Hz, 1H), 3.74 (s, 3H), 3.62 (t, J=7.6 Hz, 2H), 3.32 (m, 4H), 2.77 (m, 4H), 2.05 (t, J=7.5 Hz, 2H), 1.58 (m, 4H), 1.28 (m, 4H). MS (EST) m/z 507 (M$^+$+H).

Compound 344

N-(4-(1H-indol-6-yl)phenyl)-N-(7-(hydroxyamino)-7-oxoheptyl)-4-(3-methoxyphenyl)piperazine-1-carboxamide Compound 344 (35 mg, 92%) as a white solid was obtained according to the same method as the synthesis of compound 255.

$^1$H NMR (400 MHz, CD$_3$OD) δ 7.64 (d, J=8.5 Hz, 2H), 7.61 (s, 1H), 7.58 (d, J=8.2 Hz, 1H), 7.28 (dd, J=8.3, 1.4 Hz, 1H), 7.25 (d, J=3.1 Hz, 1H), 7.14 (d, J=8.5 Hz, 2H), 7.05 (d, J=8.2 Hz, 1H), 3.68 (s, 3H), 3.62 (t, J=7.5 Hz, 2H), 3.28 (m, 4H), 2.88 (m, 4H), 2.05 (t, J=7.4 Hz, 2H), 1.57 (m, 4H), 1.30 (m, 4H). MS (ESI) m/z 507 (M$^+$+H).

Compound 345

N-(4-(3H-benzo[d]imidazol-5-yl)phenyl)-N-(7-(hydroxyamino)-7-oxoheptyl)-4-methylpiperazine-1-carboxamide Compound 345 (39 mg, 50%) as a yellow oil was obtained according to the same method as the synthesis of compound 255.

$^1$H NMR (400 MHz, CD$_3$OD) δ 8.19 (s, 1H), 7.83 (s, 1H), 7.68 (m, 3H), 7.55 (m, 1H), 7.20 (m, 2H), 3.65 (t, J=8.0 Hz, 2H), 3.24 (m, 4H), 2.24 (m, 4H), 2.21 (s, 3H), 2.06 (m, 2H), 1.59 (m, 4H), 1.33 (m, 4H). MS (ESI) m/z 479 (M$^+$+H).

Compound 346

N-(4-(1H-indol-6-yl)phenyl)-N-(7-(hydroxyamino)-7-oxoheptyl)-4-(2-hydroxyethyl)piperazine-1-carboxamide Compound 346 (23 mg, 39%) as a white solid was obtained according to the same method as the synthesis of compound 255.

$^1$H NMR (400 MHz, CD$_3$OD) δ 7.66 (d, J=8.6 Hz, 2H), 7.61 (s, 1H), 7.59 (d, J=8.3 Hz, 1H), 7.29 (dd, J=6.7, 1.6 Hz, 1H), 7.26 (d, J=3.1 Hz, 1H), 7.16 (d, J=8.6 Hz, 2H), 6.44 (dd, J=3.1, 0.8 Hz, 1H), 3.62 (m, 2H), 3.59 (t, J=5.9 Hz, 2H), 3.24 (m, 4H), 2.45 (t, J=5.9 Hz, 2H), 2.35 (m, 4H), 2.06 (t, J=7.3 Hz, 2H), 1.58 (m, 4H), 1.32 (m, 4H). MS (ESI) m/z 508 (M$^+$+H).

Compound 347

7-(3-(2-(dimethylamino)ethyl)-1-(4-(1-methyl-1H-indzol-6-yl)phenyl)ureido)-N-hydroxyheptanamide Compound 347 (15 mg, 52%) as a yellow oil was obtained according to the same method as the synthesis of compound 255.

$^1$H NMR (400 MHz, CD$_3$OD) δ 8.01 (s, 1H), 7.82 (d, J=8.5 Hz, 2H), 7.79 (s, 1H), 7.47 (dd, J=8.5, 1.3 Hz, 1H), 7.37 (d, J=8.4 Hz, 2H), 4.11 (s, 3H), 3.69 (t, J=7.4 Hz, 2H), 3.26 (t, J=6.7 Hz, 2H), 2.26 (s, 6H), 2.08 (t, J=7.2 Hz, 2H), 1.65 (m, 4H), 1.32 (m, 4H). MS (ESI) m/z 481 (M$^+$+H).

Compound 348

N-hydroxy-7-(1-(4-(1-methyl-1H-indazol-6-yl)phenyl)-3-(2-(1-methylpyrrolidin-2-yl)ethyl)ureido)heptanamide Compound 348 (38 mg, 96%) as a yellow oil was obtained according to the same method as the synthesis of compound 255.

$^1$H NMR (400 MHz, CD$_3$OD) δ 8.00 (s, 1H), 7.83 (d, J=8.5 Hz, 2H), 7.82 (m, 1H), 7.78 (s, 1H), 7.47 (dd, J=8.5, 1.4 Hz, 1H), 7.34 (d, J=8.5 Hz, 2H), 4.10 (s, 3H), 3.68 (t, J=7.9 Hz, 2H), 3.18 (m, 2H), 2.93 (m, 1H), 2.20 (s, 3H), 2.06 (t, J=7.4 Hz, 2H), 2.00 (m, 4H), 1.60 (m, 4H), 1.51 (m, 4H), 1.27 (m, 4H). MS (ESI) m/z 521 (M$^+$+H).

Compound 349

N-(4-(1H-indol-6-yl)phenyl)-4-butyl-N-(7-(hydroxyamino)-7-oxoheptyl)piperazine-1-carboxamide Compound 349 (82 mg, 74%) as a white solid was obtained according to the same method as the synthesis of compound 255.

$^1$H NMR (400 MHz, CD$_3$OD) δ 7.64 (d, J=8.6 Hz, 2H), 7.62 (s, 1H), 7.59 (d, J=8.3 Hz, 1H), 7.28 (d, J=8.3 Hz, 1H), 7.25 (d, J=3.0 Hz, 1H), 7.10 (d, J=8.4 Hz, 2H), 3.59 (t, J=7.6 Hz, 2H), 3.11 (m, 4H), 2.05 (t, J=7.4 Hz, 2H), 1.54 (m, 4H), 1.34 (m, 6H), 1.21 (m, 4H), 0.86 (t, J=7.3 Hz, 3H). MS (ESI) m/z 520 (M$^+$+H).

Compound 350

N-(7-(hydroxyamino)-7-oxoheptyl)-4-methyl-N-(4-(1-methyl-1H-indazol-5-yl)phenyl)piperazine-1-carboxamide Compound 350 (39 mg, 50%) as a yellow oil was obtained according to the same method as the synthesis of compound 255.
$^1$H NMR (400 MHz, CD$_3$OD) δ 8.04 (s, 1H), 7.97 (s, 1H), 7.71 (m, 3H), 7.60 (d, J=8.8 Hz, 1H), 7.19 (d, J=8.5 Hz, 2H), 4.06 (s, 3H), 3.64 (t, J=7.5 Hz, 2H), 3.18 (m, 4H), 2.29 (m, 4H), 2.20 (s, 3H), 2.04 (m, 2H), 1.58 (m, 4H), 1.39 (m, 4H). MS (ESI) m/z 493 (M$^+$+H).

Compound 351

4-ethyl-N-(7-(hydroxyamino)-7-oxoheptyl)-N-(4-(1-methyl-1H-indazol-5-yl)phenyl)piperazine-1-carboxamide Compound 351 (39 mg, 50%) as a yellow oil was obtained according to the same method as the synthesis of compound 255.
$^1$H NMR (400 MHz, CD$_3$OD) δ 8.04 (s, 1H), 7.97 (s, 1H), 7.69 (m, 3H), 7.60 (m, 1H), 7.17 (d, J=13.3 Hz, 2H), 7.07 (s, 3H), 3.64 (t, J=7.2 Hz, 2H), 3.24 (s, 4H), 2.37 (m, 2H), 2.30 (m, 4H), 2.04 (t, J=6.4 Hz, 2H), 1.58 (m, 4H), 1.32 (m, 4H), 1.17 (t, J=7.1 Hz, 3H). MS (ESI) m/z 507 (M$^+$+H).

Compound 352

N-(4-(1H-indol-6-yl)phenyl)-4-(2-(dimethylamino)ethyl)-N-(7-(hydroxyamino)-7-oxoheptyl)piperazine-1-carboxamide Compound 352 (60 mg, 44%) as a yellow oil was obtained according to the same method as the synthesis of compound 255.
$^1$H NMR (400 MHz, CD$_3$OD) δ 7.68 (dd, J=8.6, 2.4 Hz, 2H), 7.61 (s, 1H), 7.59 (d, J=8.3 Hz, 1H), 7.29 (dd, J=8.3, 1.6 Hz, 1H), 7.26 (m, 1H), 7.19 (d, J=4.6 Hz, 1H), 7.17 (d, J=4.6, 1H), 6.45 (d, J=3.1 Hz, 1H), 3.65 (t, J=6.0 Hz, 2H), 3.25 (m, 4H), 2.39 (m, 2H), 2.34 (m, 2H), 2.06 (t, J=7.3 Hz, 2H), 2.04 (m, 4H), 1.84 (s, 6H), 1.58 (m, 4H), 1.33 (m, 4H). MS (ESI) m/z 535 (M$^+$+H).

Compound 353

7-(3-((1-ethylpyrrolidin-2-yl)methyl)-1-(4-(1-methyl-1H-indazol-6-yl)phenyl)ureido)-N-hydroxyheptanamide Compound 353 (40 mg, 51%) as a yellow oil was obtained according to the same method as the synthesis of compound 255.
$^1$H NMR (400 MHz, CD$_3$OD) δ 8.01 (s, 1H), 7.83 (m, 3H), 7.79 (s, 1H), 7.47 (dd, J=8.5, 1.4 Hz, 1H), 7.36 (d, J=8.5 Hz, 2H), 4.11 (s, 3H), 3.70 (t, J=6.6 Hz, 2H), 3.16 (m, 2H), 2.94 (m, 1H), 2.82 (m, 1H), 2.39 (m, 2H), 2.08 (m, 2H), 1.88 (m, 4H), 1.52 (m, 6H), 1.32 (m 4H), 1.11 (t, J=7.2 Hz, 3H). MS (ESI) m/z 521 (M$^+$+H).

Compound 354

7-(N-(4-(1H-indol-6-yl)phenyl)-4-methylpiperazine-1-sulfonamido)-N-hydroxyheptanamide Compound 354 (45 mg, 36%) as a white solid was obtained according to the same method as the synthesis of compound 180.
$^1$H NMR (400 MHz, CD$_3$OD) δ 7.69 (d, J=8.6 Hz, 2H), 7.63 (s, 1H), 7.60 (d, J=8.2 Hz, 1H), 7.46 (d, J=8.6 Hz, 2H), 7.30 (dd, J=8.3, 1.6 Hz, 1H), 7.27 (d, J=3.1 Hz, 1H), 6.45 (dd, J=3.1, 0.8 Hz, 1H), 3.69 (t, J=7.0 Hz, 2H), 3.22 (m, 4H), 2.42 (m, 4H), 2.26 (s, 3H), 2.05 (t, J=7.4 Hz, 2H), 1.57 (m, 2H), 1.45 (m, 2H), 1.30 (m, 4H). MS (ESI) m/z 514 (M$^+$+H).

Compound 355

7-(N-(4-(1H-indol-5-yl)phenyl)-4-methylpiperazine-1-sulfonamido)-N-hydroxyheptanamide Compound 355 (38 mg, 44%) as a white solid was obtained according to the same method as the synthesis of compound 180.
$^1$H NMR (400 MHz, CD$_3$OD) δ 7.80 (d, J=1.3 Hz, 1H), 7.66 (d, J=8.5 Hz, 2H), 7.43 (m, 3H), 7.38 (dd, J=8.5, 1.6 Hz, 1H), 7.26 (d, J=3.1 Hz, 1H), 3.66 (t, J=7.0 Hz, 2H), 3.21 (m, 4H), 2.40 (m, 4H), 2.24 (s, 3H), 2.05 (t, J=7.2 Hz, 2H), 1.56 (m, 2H), 1.44 (m, 2H), 1.31 (m, 4H). MS (ESI) m/z 514 (M$^+$+H).

Compound 356

N-(4-(1H-indol-6-yl)phenyl)-N-(7-(hydroxyamino)-7-oxoheptyl)-4-methylpiperidine-1-carboxamide Compound 356 (300 mg, 94%) as a white solid was obtained according to the same method as the synthesis of compound 255.
$^1$H NMR (400 MHz, CD$_3$OD) δ 7.65 (dd, J=6.7, 1.9 Hz, 2H), 7.61 (m, 1H), 7.28 (dd, J=8.2, 1.6 Hz, 1H), 7.25 (m, 1H), 7.13 (d, J=8.6 Hz, 2H), 6.44 (dd, J=3.1, 0.8 Hz, 1H), 3.82 (s, 1H), 3.79 (s, 1H), 3.62 (t, J=7.2 Hz, 2H), 2.57 (m, 2H), 2.06 (t, J=7.2 Hz, 2H), 1.57 (m, 4H), 1.42 (m, 4H), 0.91 (m, 1H), 0.90 (d, J=7.2 Hz, 3H). MS (ESI) m/z 477 (M$^+$+H).

Compound 357

7-(N-(4-(1H-indol-6-yl)phenyl)-4-methylpiperazine-1-carbothioamido)-N-hydroxyheptanamide As shown in reaction scheme 8, thiophosgene was added dropwise to compound 9, and then 1-methylpiperazine was added thereto, thus synthesizing compound 11. Then, compound 11 was subjected to the Suzuki reaction to obtain a compound of formula XVI, which was then stirred with hydroxylamine and potassium hydroxide for 30 minutes. Then, a 50% water solution of hydroxylamine was added to the stirred solution until the undissolved solids were dissolved so that the solution became clear. Then, the reaction solution was stirred at mom temperature for 10 hours, and after the completion of the reaction has been confirmed, the reaction product was concentrated under reduced pressure to remove the solvent. The remaining material was extracted using ethyl acetate, washed with brine, dried with anhydrous magnesium sulfate, filtered, and concentrated under reduced pressure. The residue was crystallized, thus obtaining compound 357 (146 mg, 95%).

¹H NMR (400 MHz, CD₃OD) δ 7.69 (d, J=6.6 Hz, 2H), 7.60 (m, 2H), 7.29 (m, 2H), 7.14 (d, J=8.6 Hz, 2H), 6.45 (d, J=3.1 Hz, 1H), 4.09 (m, 2H), 3.58 (m, 4H), 2.28 (m, 4H), 2.20 (s, 3H), 2.07 (t, J=7.4 Hz, 2H), 1.73 (m, 2H), 1.59 (m, 2H), 1.34 (m, 4H). MS (ESI) m/z 494 (M⁺+H).

Compound 358

7-(N-(4-(1H-indol-5-yl)phenyl)-4-methylpiperazine-1-carbothioamido)-N-hydroxyheptanamide Compound 358 (168 mg, 98%) as a brown solid was obtained according to the same method as the synthesis of compound 357.
¹H NMR (400 MHz, CD₃OD) δ 7.79 (s, 1H), 7.67 (d, J=6.6 Hz, 2H), 7A4 (d, J=8.5 Hz, 1H), 7.38 (d, J=8.5 Hz, 1H), 7.25 (d, J=3.2 Hz, 1H), 7.14 (m, 2H), 6.49 (d, J=3.1 Hz, 1H), 4.09 (m, 2H), 3.58 (m, 4H), 2.28 (m, 4H), 2.20 (s, 3H), 2.07 (t, J=7.4 Hz, 2H), 1.72 (m, 2H), 1.59 (m, 2H), 1.33 (m, 4H). MS (ESI) m/z 494 (M⁺+H).

Compound 359

N-hydroxy-7-(4-methyl-N-(4-(1-methyl-1H-indazol-5-yl)phenyl)piperazine-1-thiocarboamido)heptanamide Compound 359 (30 mg, 38%) as a brown oil was obtained according to the same method as the synthesis of compound 357.
¹H NMR (400 MHz, CD₃OD) δ 8.05 (s, 1H), 7.99 (s, 1H), 7.72 (m, 3H), 7.62 (d, J=8.8 Hz, 1H), 7.17 (d, J=8.6 Hz, 2H), 4.09 (m, 5H), 3.59 (m, 4H), 2.29 (m, 4H), 2.21 (s, 3H), 2.07 (t, J=7.5 Hz, 2H), 1.73 (m, 2H), 1.60 (m, 2H), 1.34 (m, 4H). MS (ESI) m/z 509 (M⁺+H).

The chemical structures of compounds 150 to 359 as described above are shown in Tables 1 to 15 below.

TABLE 1

| Compound | Structure |
| --- | --- |
| 150 | 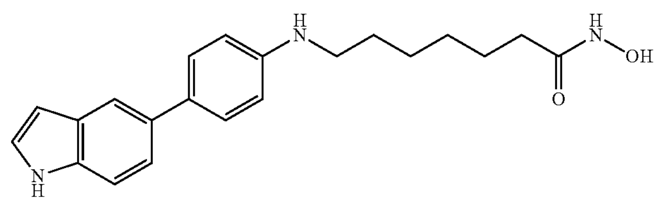 [SMILES: O=C(CCCCCCNc1ccc(-c2ccc3[nH]ccc3c2)cc1)NO] |
| 158 | 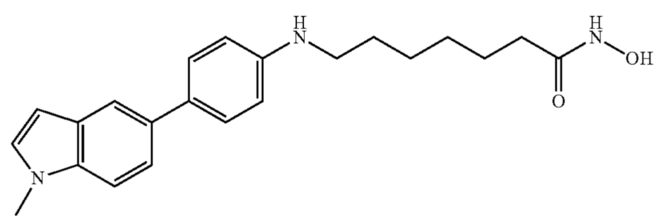 [SMILES: Cn1ccc2cc(-c3ccc(NCCCCCCC(=O)NO)cc3)ccc21] |
| 166 | 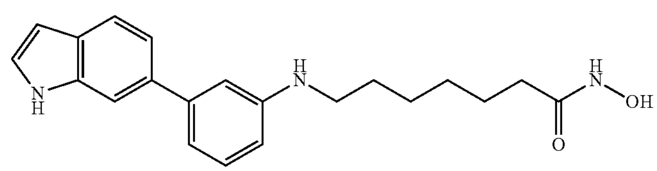 [SMILES: O=C(CCCCCCNc1cccc(-c2ccc3cc[nH]c3c2)c1)NO] |
| 167 | 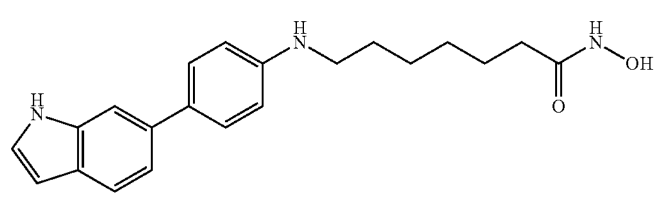 [SMILES: O=C(CCCCCCNc1ccc(-c2ccc3cc[nH]c3c2)cc1)NO] |
| 169 | 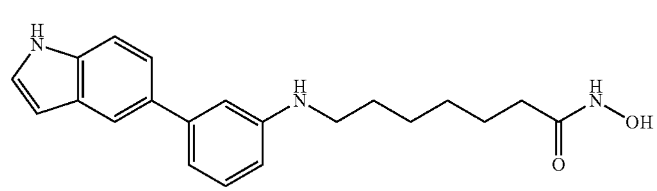 [SMILES: O=C(CCCCCCNc1cccc(-c2ccc3[nH]ccc3c2)c1)NO] |

TABLE 1-continued

| Compound | Structure |
|---|---|
| 170 | 4-(1H-indol-4-yl)phenyl-NH-(CH2)5-C(=O)-NHOH |
| 172 | 2-(1H-indol-5-yl)phenyl-NH-(CH2)5-C(=O)-NHOH |
| 174 | 5-(1H-indol-6-yl)pyridin-2-yl-NH-(CH2)5-C(=O)-NHOH |
| 175 | 6-(1H-indol-6-yl)pyridin-3-yl-NH-(CH2)5-C(=O)-NHOH |
| 176 | 3-(1H-indol-7-yl)phenyl-NH-(CH2)5-C(=O)-NHOH |

TABLE 2

| Compound | Structure |
|---|---|
| 178 | 5-(1H-indol-6-yl)pyrimidin-2-yl-NH-(CH2)5-C(=O)-NHOH |
| 179 | 4-(1H-indol-7-yl)phenyl-NH-(CH2)5-C(=O)-NHOH |

TABLE 2-continued
| Compound | Structure |
|---|---|
| 180 | 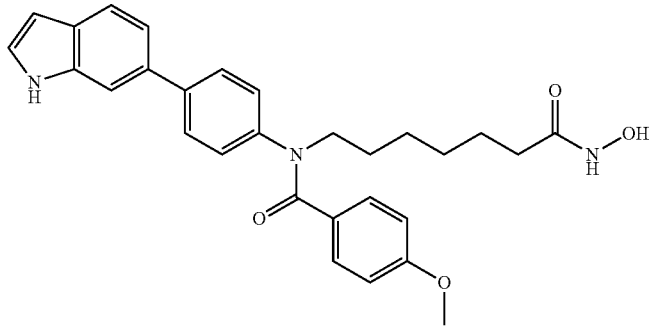 [SMILES: COc1ccc(C(=O)N(CCCCCCC(=O)NO)c2ccc(-c3ccc4cc[nH]c4c3)cc2)cc1] |
| 181 | 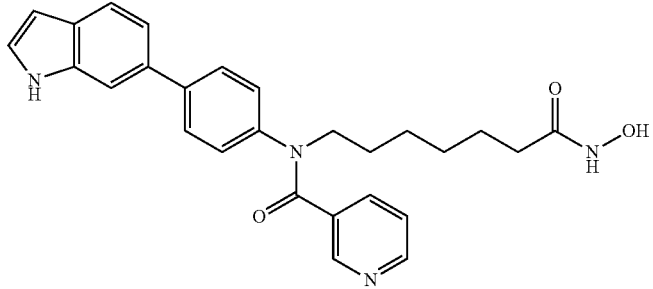 [SMILES: O=C(CCCCCCN(C(=O)c1cccnc1)c1ccc(-c2ccc3cc[nH]c3c2)cc1)NO] |
| 184 | 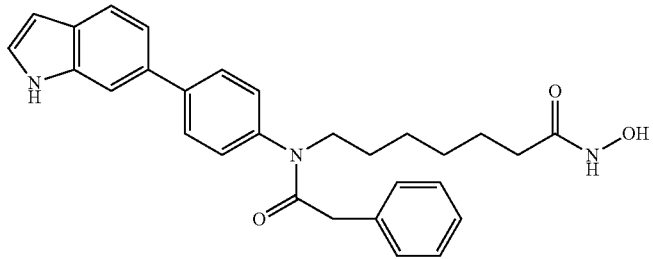 [SMILES: O=C(CCCCCCN(C(=O)Cc1ccccc1)c1ccc(-c2ccc3cc[nH]c3c2)cc1)NO] |
| 185 | 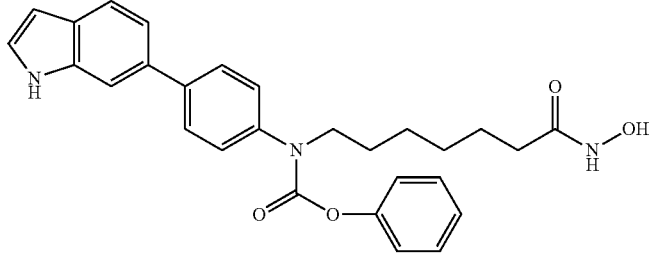 [SMILES: O=C(CCCCCCN(C(=O)Oc1ccccc1)c1ccc(-c2ccc3cc[nH]c3c2)cc1)NO] |
| 189 | 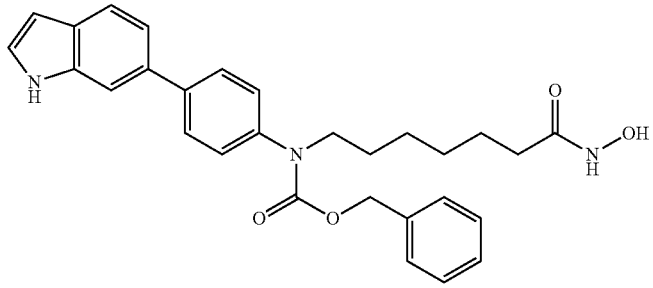 [SMILES: O=C(CCCCCCN(C(=O)OCc1ccccc1)c1ccc(-c2ccc3cc[nH]c3c2)cc1)NO] |

TABLE 2-continued

| Compound | Structure |
|---|---|
| 190 | (structure) |
| 191 | (structure) |
| 203 | (structure) |

TABLE 3

| Compound | Structure |
|---|---|
| 204 | (structure) |
| 207 | (structure) |

TABLE 3-continued

| Compound | Structure |
|---|---|
| 208 | *1H-indol-5-yl-phenyl, N-(6-(hydroxyamino)-6-oxohexyl), N-(4-methoxybenzoyl)* |
| 209 | *1H-indol-6-yl-phenyl, N-(6-(hydroxyamino)-6-oxohexyl), N-(4-methylbenzoyl)* |
| 210 | *1H-indol-6-yl-phenyl, N-(6-(hydroxyamino)-6-oxohexyl), N-(phenylsulfonyl)* |
| 211 | *1H-indol-6-yl-phenyl, N-(6-(hydroxyamino)-6-oxohexyl), N-(pyridine-2-carbonyl)* |
| 212 | *1H-indol-6-yl-phenyl, N-(6-(hydroxyamino)-6-oxohexyl), N-(3-methoxybenzoyl)* |

TABLE 3-continued
| Compound | Structure |
|---|---|
| 214 | 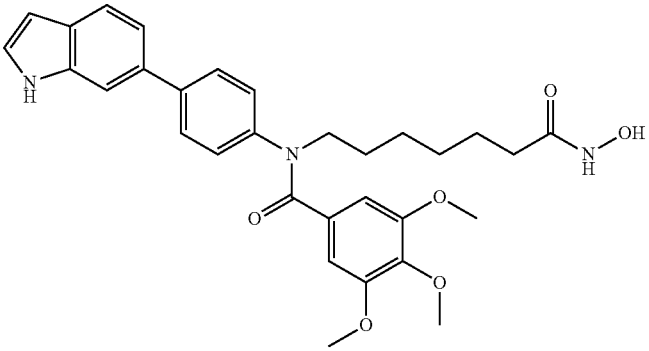 [SMILES: COc1cc(C(=O)N(CCCCCCC(=O)NO)c2ccc(-c3ccc4cc[nH]c4c3)cc2)cc(OC)c1OC] |
| 215 | 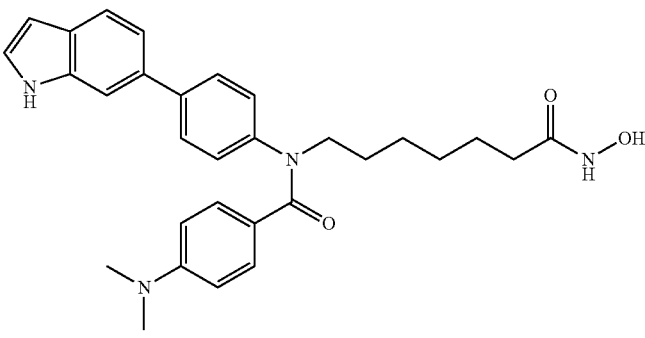 [SMILES: CN(C)c1ccc(C(=O)N(CCCCCCC(=O)NO)c2ccc(-c3ccc4cc[nH]c4c3)cc2)cc1] |
| 218 | 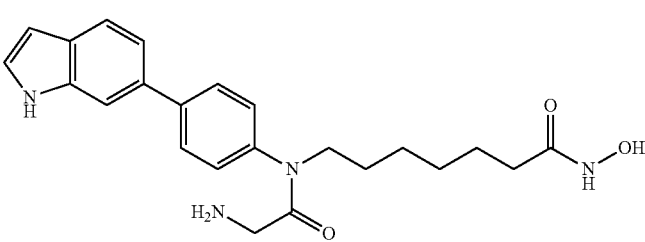 [SMILES: NCC(=O)N(CCCCCCC(=O)NO)c1ccc(-c2ccc3cc[nH]c3c2)cc1] |
TABLE 4
| Compound | Structure |
|---|---|
| 221 | 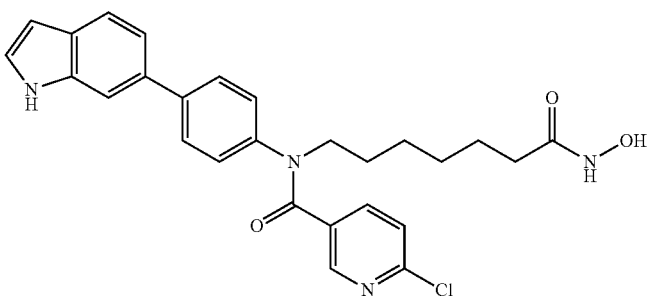 [SMILES: O=C(CCCCCCN(C(=O)c1ccc(F)cc1)c1ccc(-c2ccc3cc[nH]c3c2)cc1)NO] |

TABLE 4-continued

| Compound | Structure |
|---|---|
| 222 | (6-(1H-indol-6-yl)phenyl)-N-(6-(hydroxyamino)-6-oxohexyl)-N-(isonicotinoyl) aniline derivative |
| 228 | 4-((N-(4-(1H-indol-6-yl)phenyl)-N-(6-(hydroxyamino)-6-oxohexyl)carbamoyl)-N'-hydroxybenzimidamide |
| 229 | N-(4-(1H-indol-6-yl)phenyl)-2,6-difluoro-N-(6-(hydroxyamino)-6-oxohexyl)benzamide |
| 230 | N-(4-(1H-indol-6-yl)phenyl)-4-fluoro-N-(6-(hydroxyamino)-6-oxohexyl)benzamide |
| 231 | N-(4-(1H-indol-6-yl)phenyl)-N-(6-(hydroxyamino)-6-oxohexyl)-6-(trifluoromethyl)nicotinamide |

TABLE 4-continued

| Compound | Structure |
|---|---|
| 234 | 6-(1H-indol-6-yl)phenyl-NH-(CH2)5-C(O)NHOH |
| 235 | 6-(1H-indol-6-yl)phenyl-NH-(CH2)6-C(O)NHOH |
| 236 | 6-(1H-indol-6-yl)phenyl-N[(CH2)6C(O)NHOH]-C(O)-(4-ethoxyphenyl) |
| 237 | 6-(1H-indol-6-yl)phenyl-N[(CH2)6C(O)NHOH]-CH2-phenyl |

TABLE 5

| Compound | Structure |
|---|---|
| 239 | 6-(1H-indol-6-yl)phenyl-N[(CH2)6C(O)NHOH]-C(O)-(2,4,6-trifluorophenyl) |

TABLE 5-continued

| Compound | Structure |
|---|---|
| 242 | 1H-indol-6-yl-phenyl-N(C(O)-C6H4-4-NH2)-N-(CH2)5-C(O)NHOH |
| 243 | 1H-indol-6-yl-phenyl-N(C(O)-piperidin-1-yl)-N-(CH2)5-C(O)NHOH |
| 244 | 1H-indol-6-yl-phenyl-N(C(O)-C6H3-3-CF3-4-OMe)-N-(CH2)6-C(O)NHOH |
| 245 | 1H-indol-6-yl-phenyl-N(C(O)-C6H4-4-CF3)-N-(CH2)6-C(O)NHOH |
| 246 | 1H-indol-6-yl-phenyl-N(C(O)-C6H3-3,4-diOMe)-N-(CH2)6-C(O)NHOH |

TABLE 5-continued

| Compound | Structure |
|---|---|
| 249 | 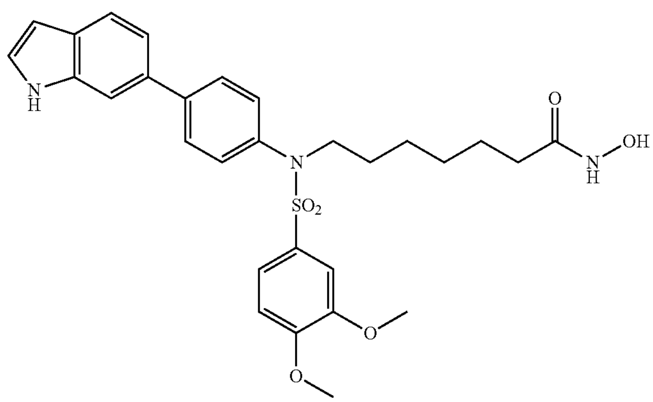 [SMILES: COc1ccc(S(=O)(=O)N(CCCCCCC(=O)NO)c2ccc(-c3ccc4cc[nH]c4c3)cc2)cc1OC] |
| 250 | 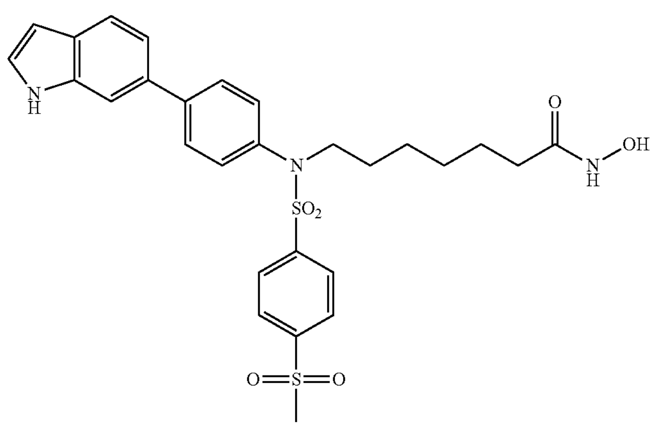 [SMILES: CS(=O)(=O)c1ccc(S(=O)(=O)N(CCCCCCC(=O)NO)c2ccc(-c3ccc4cc[nH]c4c3)cc2)cc1] |
| 251 | 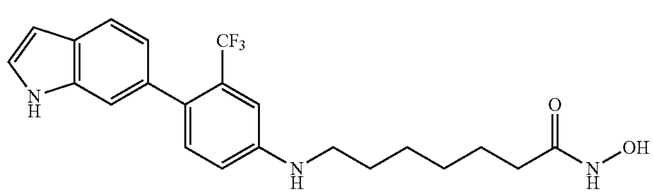 [SMILES: O=C(CCCCCCNc1ccc(-c2ccc3cc[nH]c3c2)c(C(F)(F)F)c1)NO] |
| 252 | 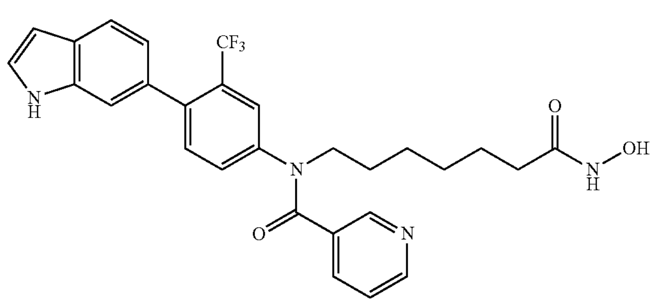 [SMILES: O=C(CCCCCCN(C(=O)c1cccnc1)c1ccc(-c2ccc3cc[nH]c3c2)c(C(F)(F)F)c1)NO] |

TABLE 6

| Compound | Structure |
|---|---|
| 253 | 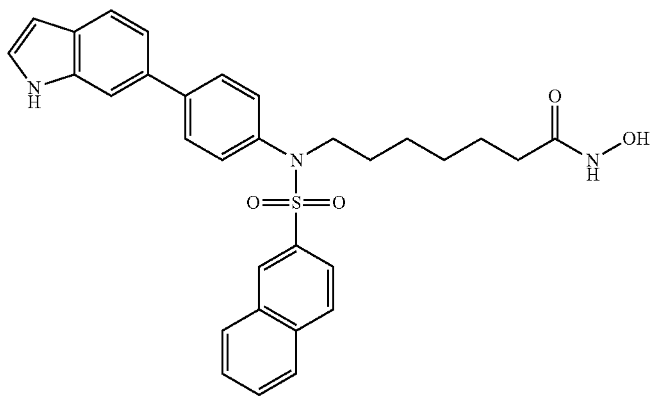 [SMILES: O=C(CCCCCCN(c1ccc(-c2ccc3cc[nH]c3c2)cc1)S(=O)(=O)c1ccc2ccccc2c1)NO] |
| 254 | 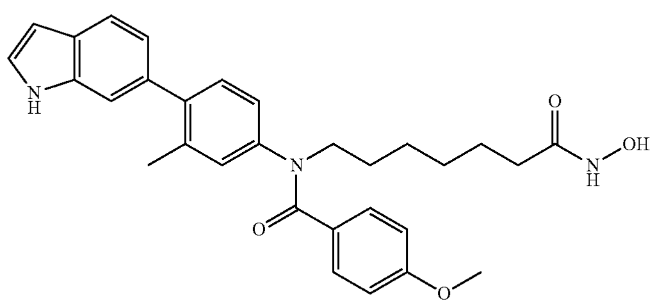 [SMILES: COc1ccc(C(=O)N(CCCCCCC(=O)NO)c2ccc(-c3ccc4cc[nH]c4c3)c(C)c2)cc1] |
| 255 | 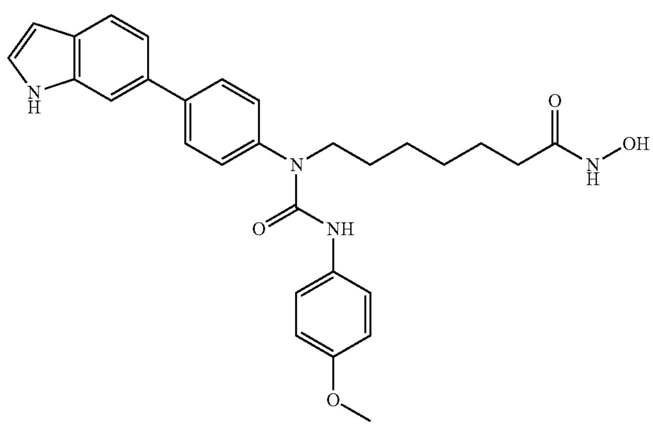 [SMILES: COc1ccc(NC(=O)N(CCCCCCC(=O)NO)c2ccc(-c3ccc4cc[nH]c4c3)cc2)cc1] |
| 256 | 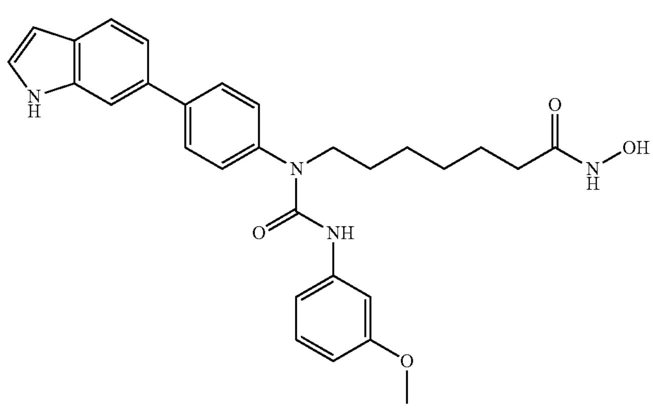 [SMILES: COc1cccc(NC(=O)N(CCCCCCC(=O)NO)c2ccc(-c3ccc4cc[nH]c4c3)cc2)c1] |

TABLE 6-continued

| Compound | Structure |
|---|---|
| 257 | (indol-6-yl)-phenyl-N(acetyl)-N-(hexyl)-C(O)NHOH |
| 258 | (indol-6-yl)-phenyl-N(C(O)OMe)-N-(hexyl)-C(O)NHOH |
| 259 | (indol-6-yl)-phenyl-N[C(O)NH-(2-methoxyphenyl)]-N-(hexyl)-C(O)NHOH |
| 260 | (indol-6-yl)-phenyl-N[C(O)NH-(3,5-dimethoxyphenyl)]-N-(hexyl)-C(O)NHOH |
| 261 | (indol-6-yl)-phenyl-N[SO$_2$-(5-amino-2-methoxyphenyl)]-N-(hexyl)-C(O)NHOH |

TABLE 6-continued
| Compound | Structure |
|---|---|
| 262 | 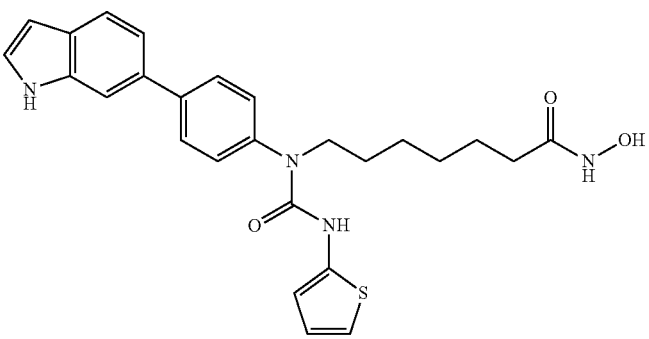 [SMILES: O=C(CCCCCCN(C(=O)Nc1cccs1)c1ccc(-c2ccc3cc[nH]c3c2)cc1)NO] |
TABLE 7
| Compound | Structure |
|---|---|
| 263 | 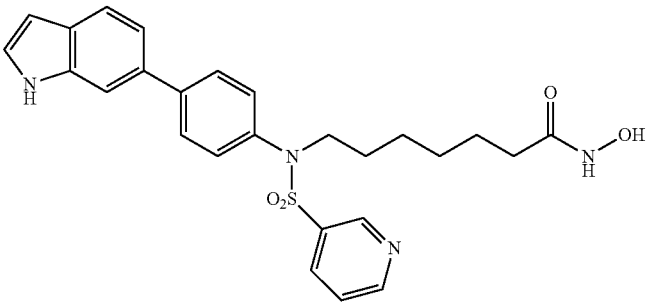 [SMILES: O=C(CCCCCCN(c1ccc(-c2ccc3cc[nH]c3c2)cc1)S(=O)(=O)c1cccnc1)NO] |
| 264 | 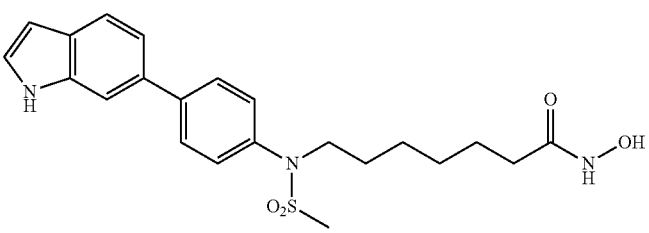 |
| 265 | 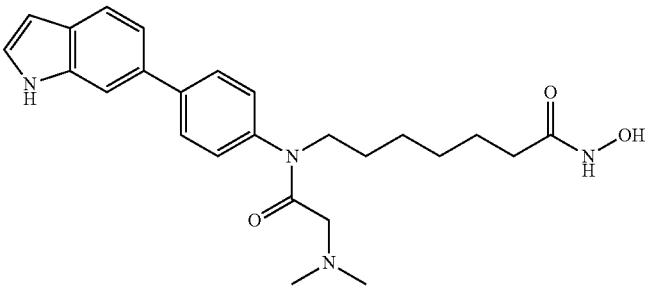 [SMILES: CN(C)CC(=O)N(CCCCCCC(=O)NO)c1ccc(-c2ccc3cc[nH]c3c2)cc1] |

TABLE 7-continued
| Compound | Structure |
|---|---|
| 266 | 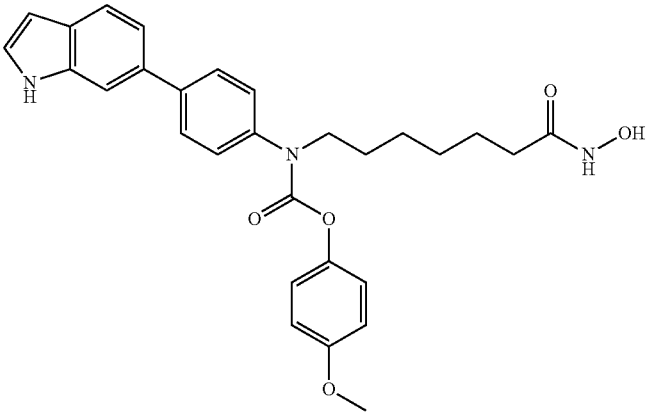 [SMILES: COc1ccc(OC(=O)N(CCCCCCC(=O)NO)c2ccc(-c3ccc4cc[nH]c4c3)cc2)cc1] |
| 267 | 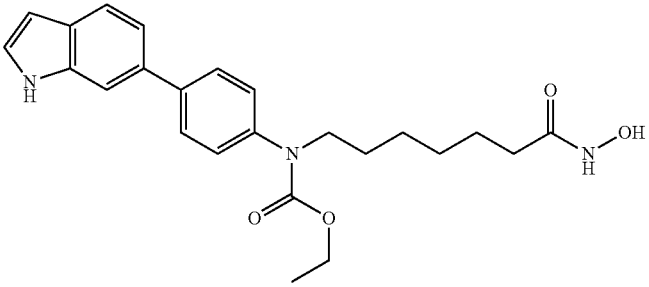 [SMILES: CCOC(=O)N(CCCCCCC(=O)NO)c1ccc(-c2ccc3cc[nH]c3c2)cc1] |
| 268 | 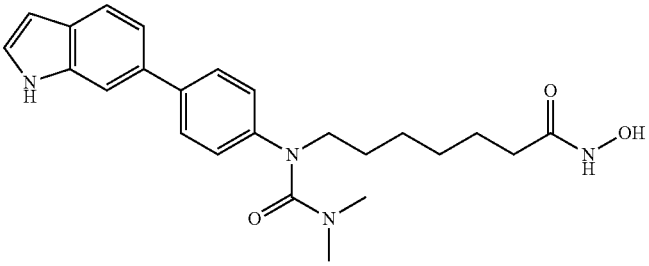 [SMILES: CN(C)C(=O)N(CCCCCCC(=O)NO)c1ccc(-c2ccc3cc[nH]c3c2)cc1] |
| 269 | 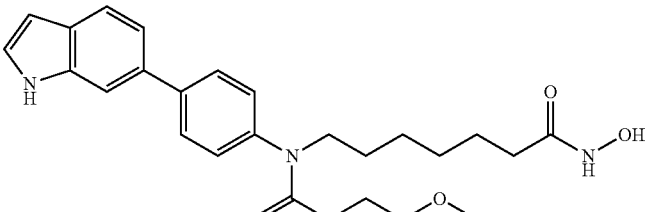 |
| 270 | 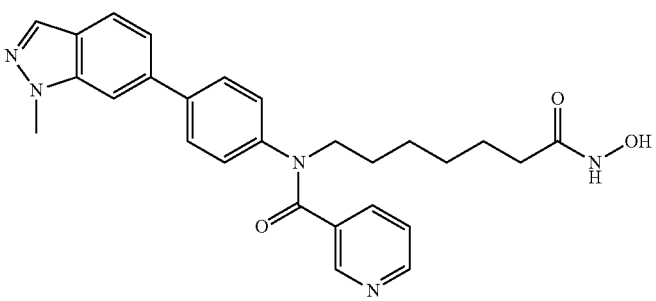 [SMILES: Cn1ncc2ccc(-c3ccc(N(CCCCCCC(=O)NO)C(=O)c4cccnc4)cc3)cc21] |

TABLE 7-continued
| Compound | Structure |
|---|---|
| 271 | 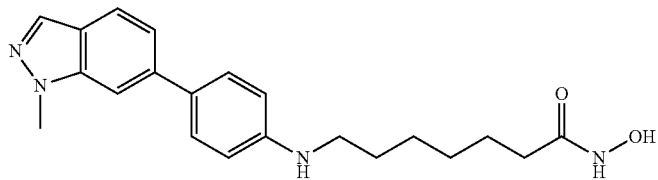 [SMILES: Cn1ncc2ccc(-c3ccc(NCCCCCCC(=O)NO)cc3)cc21] |
| 272 | 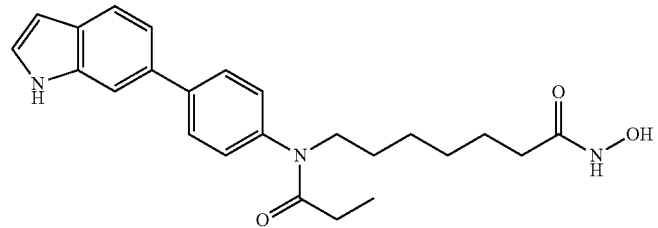 |
TABLE 8
| Compound | Structure |
|---|---|
| 273 | 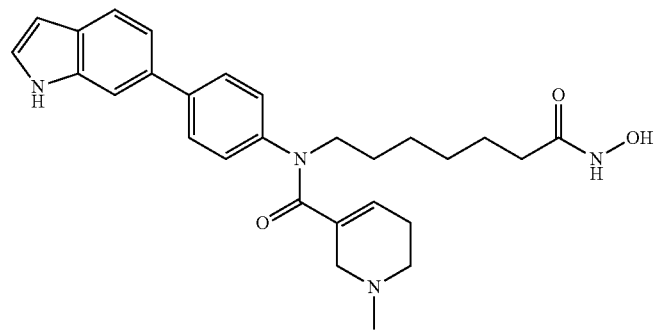 [SMILES: CN1CCC=C(C(=O)N(CCCCCCC(=O)NO)c2ccc(-c3ccc4cc[nH]c4c3)cc2)C1] |
| 274 | 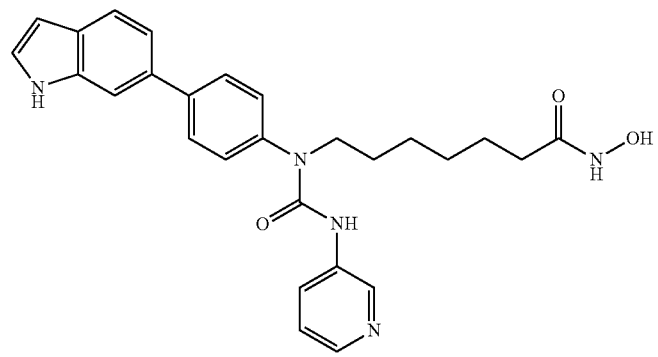 [SMILES: O=C(CCCCCCN(C(=O)Nc1cccnc1)c1ccc(-c2ccc3cc[nH]c3c2)cc1)NO] |
| 275 | 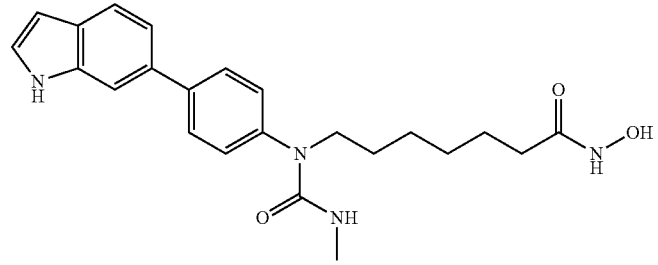 [SMILES: CNC(=O)N(CCCCCCC(=O)NO)c1ccc(-c2ccc3cc[nH]c3c2)cc1] |

TABLE 8-continued
| Compound | Structure |
|---|---|
| 276 | 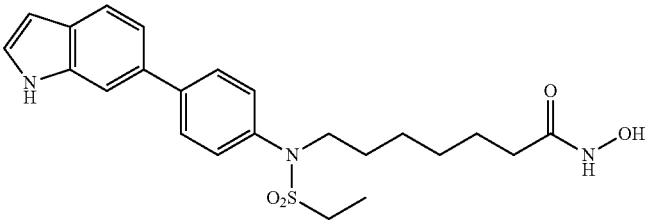 [SMILES: CCS(=O)(=O)N(CCCCCCC(=O)NO)c1ccc(-c2ccc3cc[nH]c3c2)cc1] |
| 277 | 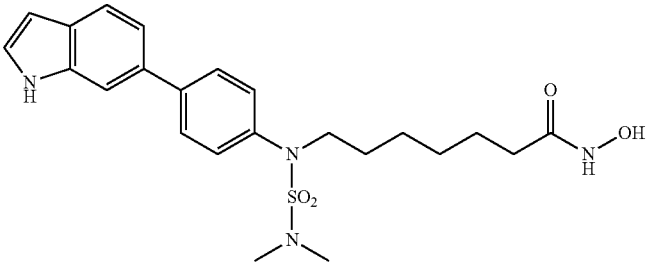 [SMILES: CN(C)S(=O)(=O)N(CCCCCCC(=O)NO)c1ccc(-c2ccc3cc[nH]c3c2)cc1] |
| 278 | 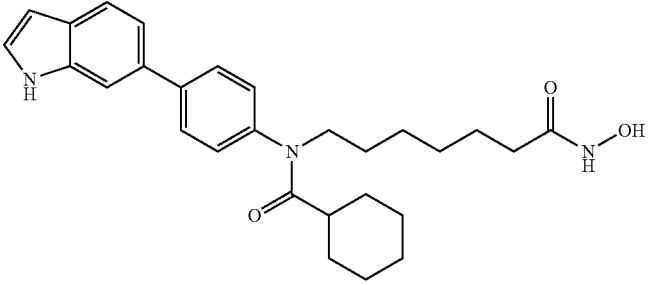 [SMILES: O=C(CCCCCCN(C(=O)C1CCCCC1)c1ccc(-c2ccc3cc[nH]c3c2)cc1)NO] |
| 279 | 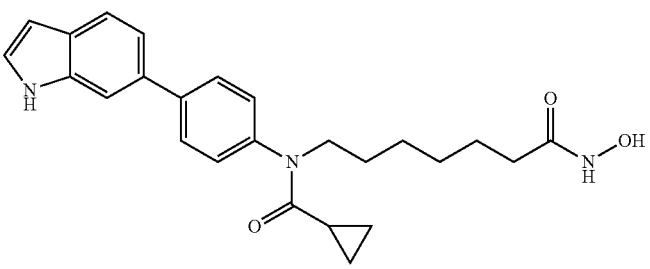 [SMILES: O=C(CCCCCCN(C(=O)C1CC1)c1ccc(-c2ccc3cc[nH]c3c2)cc1)NO] |
| 280 | 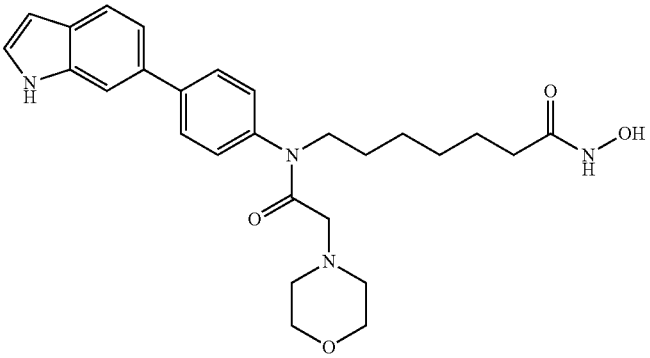 [SMILES: O=C(CCCCCCN(C(=O)CN1CCOCC1)c1ccc(-c2ccc3cc[nH]c3c2)cc1)NO] |

TABLE 8-continued

| Compound | Structure |
|---|---|
| 281 | 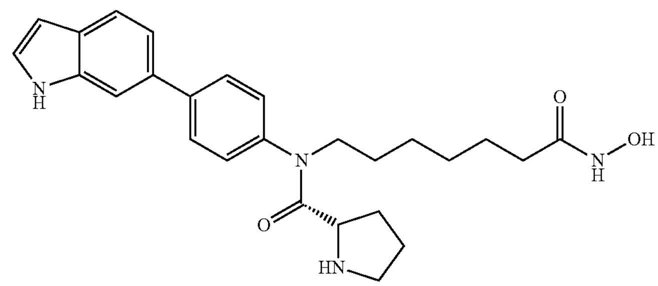 |
| 282 | 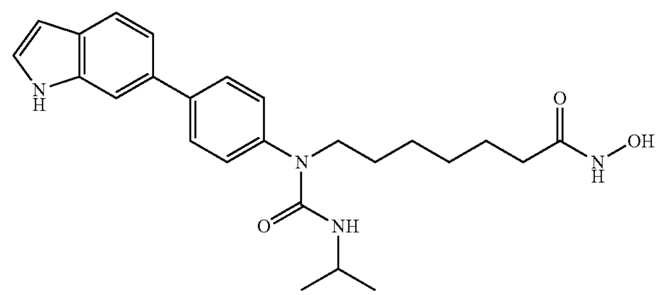 [SMILES: CC(C)NC(=O)N(CCCCCCC(=O)NO)c1ccc(-c2ccc3cc[nH]c3c2)cc1] |

TABLE 9

| Compound | Structure |
|---|---|
| 283 | 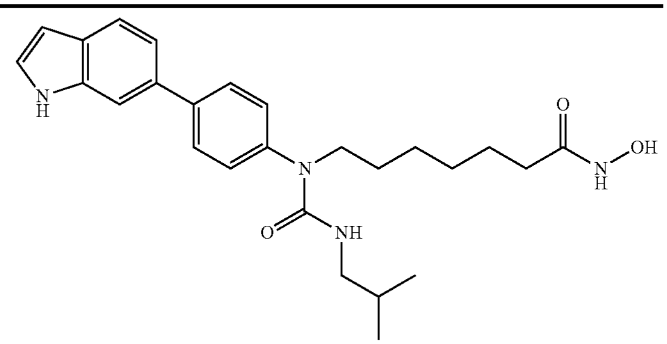 |
| 284 | 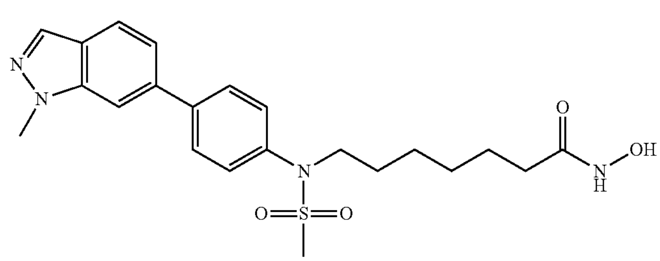 [SMILES: Cn1ncc2ccc(-c3ccc(N(CCCCCCC(=O)NO)S(C)(=O)=O)cc3)cc21] |
| 285 | 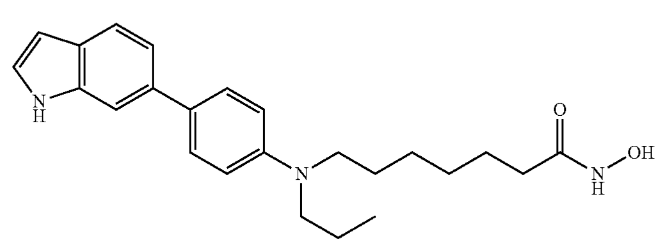 [SMILES: CCCN(CCCCCCC(=O)NO)c1ccc(-c2ccc3cc[nH]c3c2)cc1] |

TABLE 9-continued
| Compound | Structure |
|---|---|
| 286 | 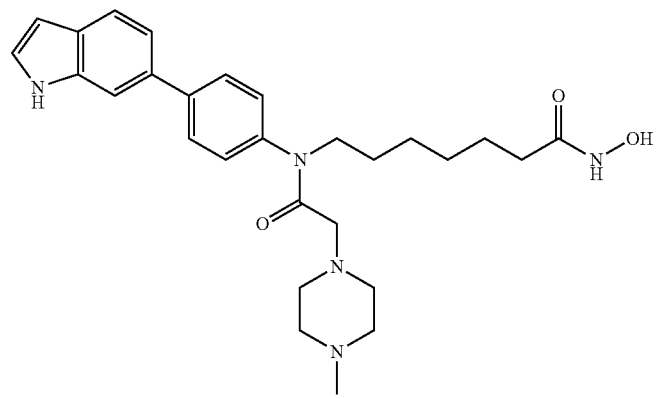 [SMILES: CN1CCN(CC(=O)N(CCCCCCC(=O)NO)c2ccc(-c3ccc4cc[nH]c4c3)cc2)CC1] |
| 287 | 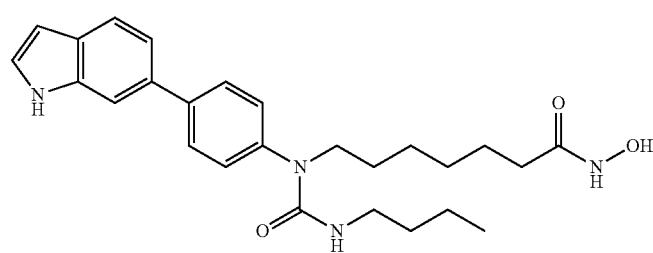 [SMILES: CCCCNC(=O)N(CCCCCCC(=O)NO)c1ccc(-c2ccc3cc[nH]c3c2)cc1] |
| 288 | 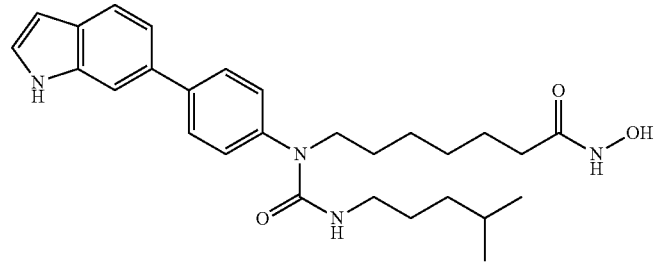 [SMILES: CC(C)CCCNC(=O)N(CCCCCCC(=O)NO)c1ccc(-c2ccc3cc[nH]c3c2)cc1] |
| 289 | 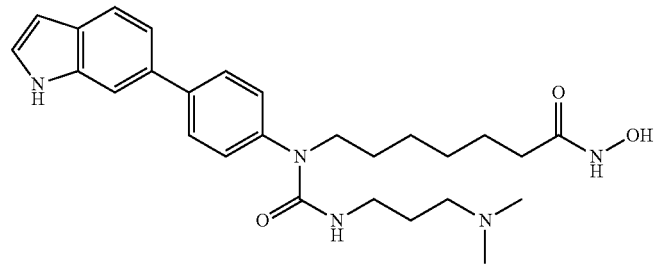 |
| 290 | 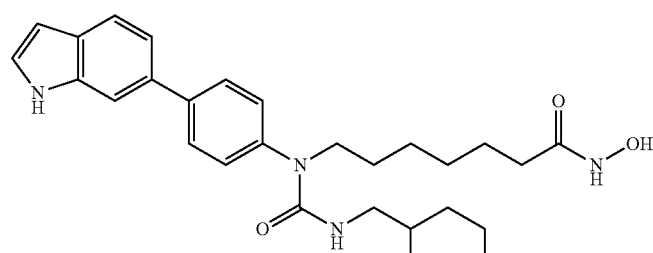 |

TABLE 9-continued

| Compound | Structure |
|---|---|
| 291 | (structure) |
| 292 | (structure) |

TABLE 10

| Compound | Structure |
|---|---|
| 293 | (structure) |
| 294 | (structure) |
| 295 | (structure) |

TABLE 10-continued

| Compound | Structure |
| --- | --- |
| 296 | 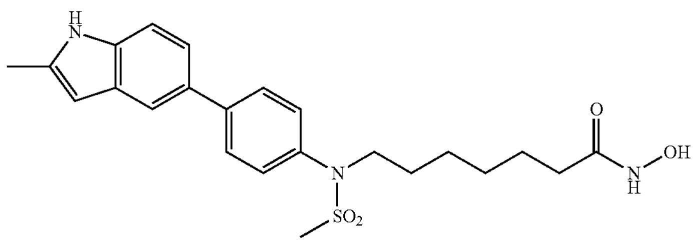 [SMILES: Cc1cc2cc(-c3ccc(N(CCCCCCC(=O)NO)S(C)(=O)=O)cc3)ccc2[nH]1] |
| 299 | 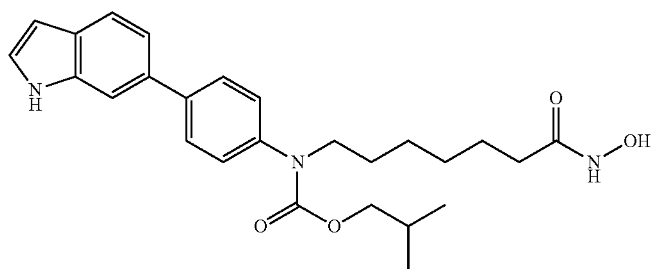 [SMILES: CC(C)COC(=O)N(CCCCCCC(=O)NO)c1ccc(-c2ccc3cc[nH]c3c2)cc1] |
| 300 | 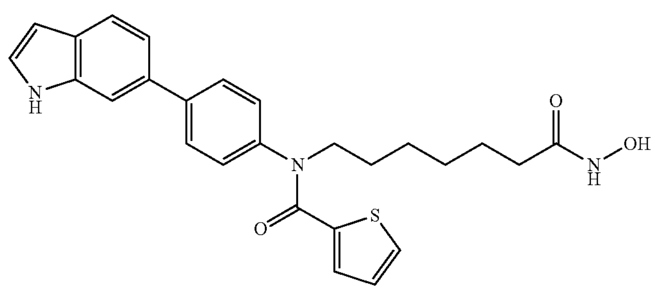 [SMILES: O=C(CCCCCCN(C(=O)c1cccs1)c1ccc(-c2ccc3cc[nH]c3c2)cc1)NO] |
| 302 | 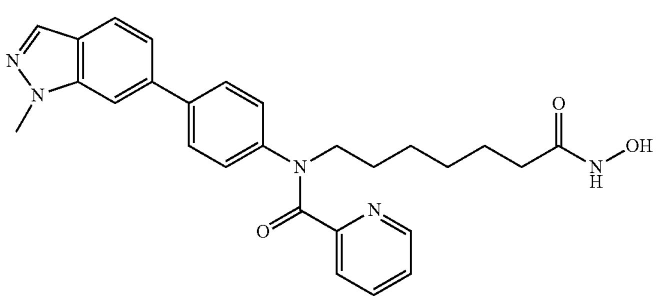 [SMILES: Cn1ncc2ccc(-c3ccc(N(CCCCCCC(=O)NO)C(=O)c4ccccn4)cc3)cc21] |
| 303 | 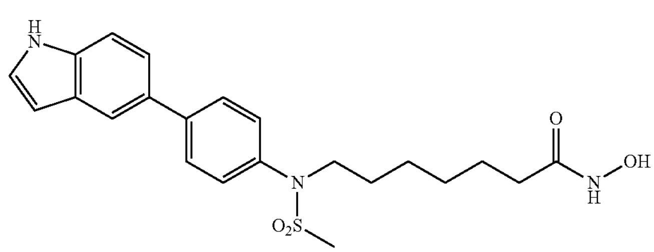 [SMILES: CS(=O)(=O)N(CCCCCCC(=O)NO)c1ccc(-c2ccc3[nH]ccc3c2)cc1] |

TABLE 10-continued

| Compound | Structure |
|---|---|
| 304 | 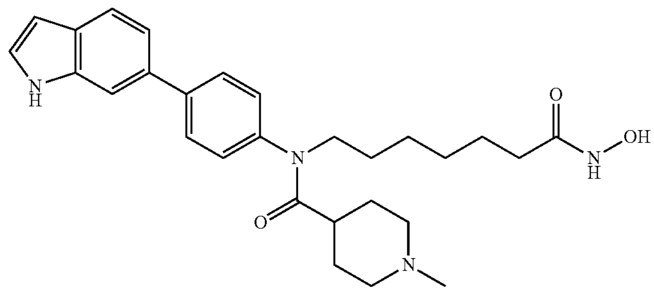 [SMILES: CN1CCC(C(=O)N(CCCCCCC(=O)NO)c2ccc(-c3ccc4cc[nH]c4c3)cc2)CC1] |
| 305 | 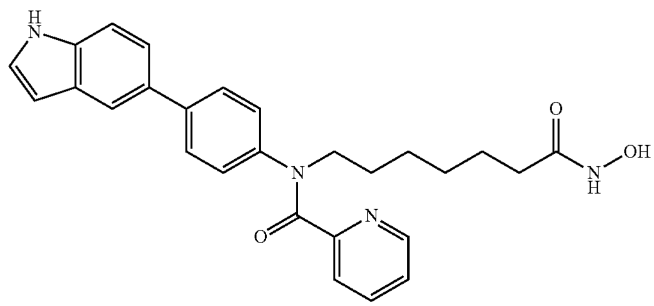 [SMILES: O=C(CCCCCCN(C(=O)c1ccccn1)c1ccc(-c2ccc3[nH]ccc3c2)cc1)NO] |

TABLE 11

| Compound | Structure |
|---|---|
| 306 | 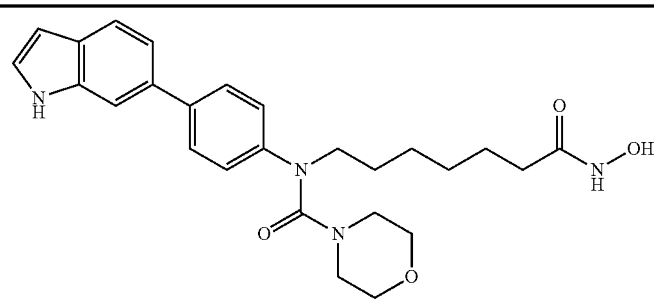 |
| 307 | 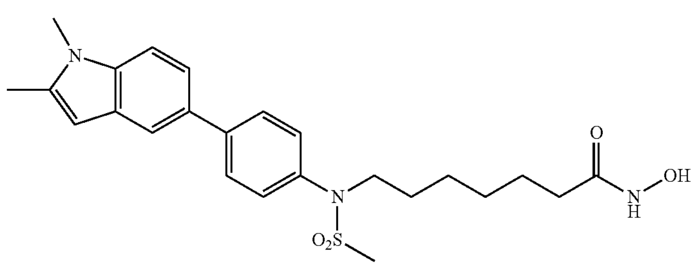 [SMILES: Cc1cc2cc(-c3ccc(N(CCCCCCC(=O)NO)S(C)(=O)=O)cc3)ccc2n1C] |
| 309 | 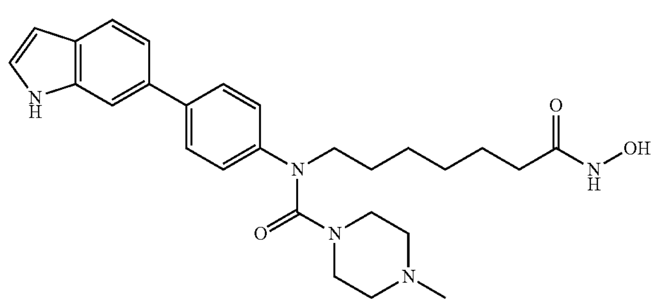 |

TABLE 11-continued

| Compound | Structure |
|---|---|
| 310 | 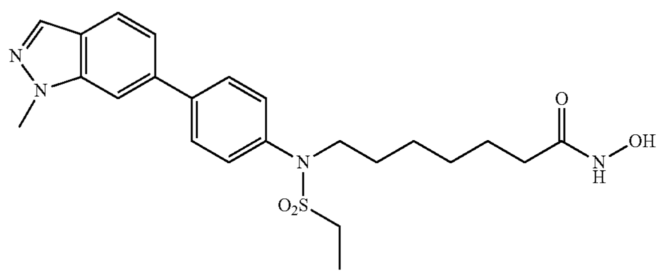 [SMILES: CCS(=O)(=O)N(CCCCCCC(=O)NO)c1ccc(-c2ccc3cnn(C)c3c2)cc1] |
| 311 | 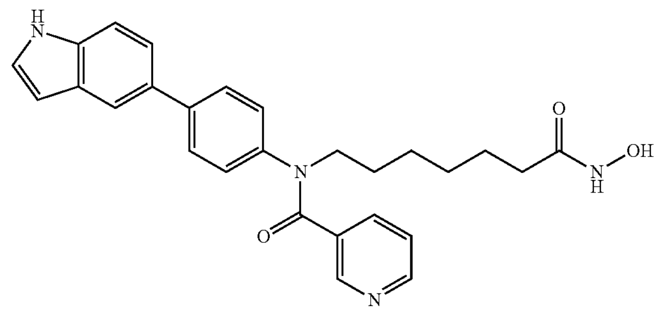 [SMILES: O=C(CCCCCCN(C(=O)c1cccnc1)c1ccc(-c2ccc3[nH]ccc3c2)cc1)NO] |
| 312 | 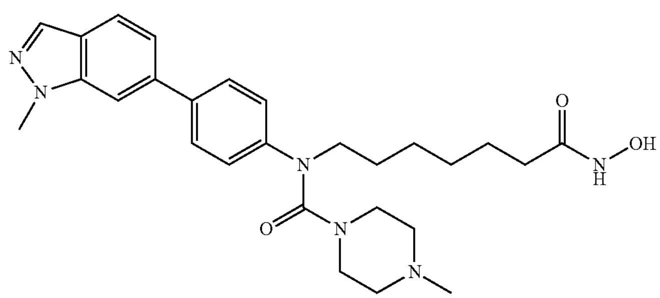 [SMILES: CN1CCN(C(=O)N(CCCCCCC(=O)NO)c2ccc(-c3ccc4cnn(C)c4c3)cc2)CC1] |
| 313 | 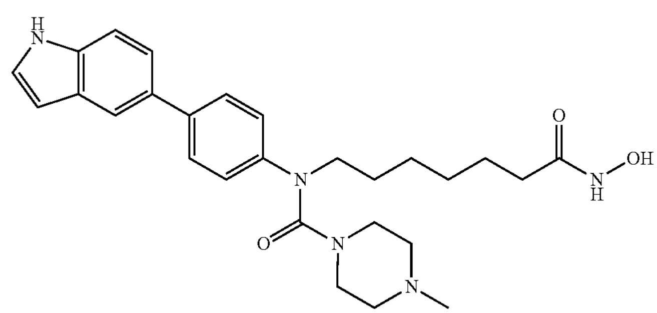 [SMILES: CN1CCN(C(=O)N(CCCCCCC(=O)NO)c2ccc(-c3ccc4[nH]ccc4c3)cc2)CC1] |
| 314 | 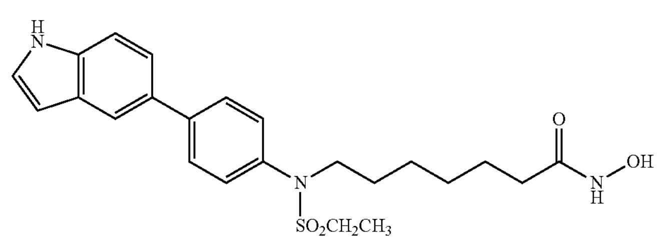 |

TABLE 11-continued

| Compound | Structure |
|---|---|
| 315 | *(1-methyl-1H-indazol-6-yl)phenyl substituted N-(7-(hydroxyamino)-7-oxoheptyl)-morpholine-4-carboxamide)* |
| 316 | *(1H-indol-5-yl)phenyl substituted N-(7-(hydroxyamino)-7-oxoheptyl)-morpholine-4-carboxamide* |

TABLE 12

| Compound | Structure |
|---|---|
| 317 | *(1H-indol-6-yl)phenyl substituted N-(7-(hydroxyamino)-7-oxoheptyl)-2,6-dimethylmorpholine-4-carboxamide* |
| 318 | *(1-methyl-1H-indazol-6-yl)phenyl substituted N-(7-(hydroxyamino)-7-oxoheptyl)-2,6-dimethylmorpholine-4-carboxamide* |

TABLE 12-continued

| Compound | Structure |
| --- | --- |
| 319 | 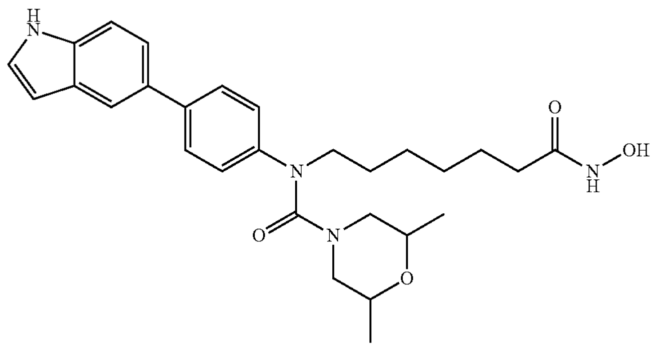 [SMILES: CC1CN(C(=O)N(CCCCCCC(=O)NO)c2ccc(-c3ccc4[nH]ccc4c3)cc2)CC(C)O1] |
| 320 | 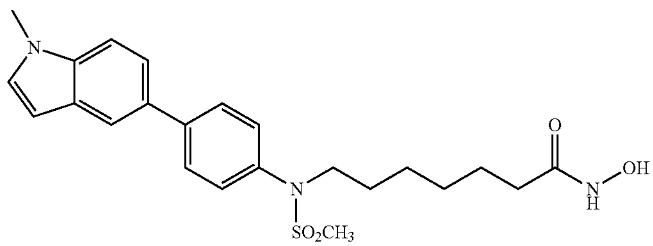 [SMILES: Cn1ccc2cc(-c3ccc(N(CCCCCCC(=O)NO)S(C)(=O)=O)cc3)ccc21] |
| 321 | 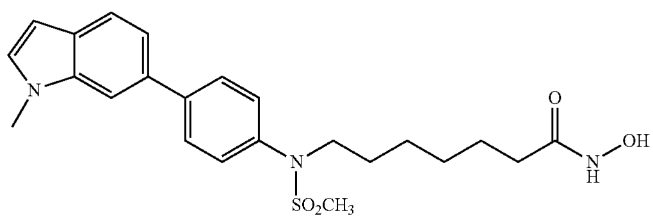 [SMILES: Cn1ccc2ccc(-c3ccc(N(CCCCCCC(=O)NO)S(C)(=O)=O)cc3)cc21] |
| 323 | 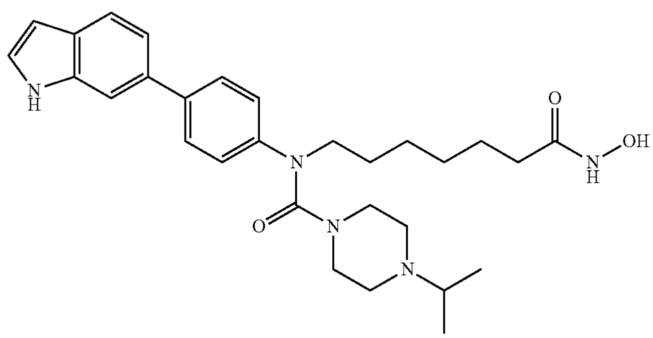 [SMILES: CC(C)N1CCN(C(=O)N(CCCCCCC(=O)NO)c2ccc(-c3ccc4cc[nH]c4c3)cc2)CC1] |
| 324 | 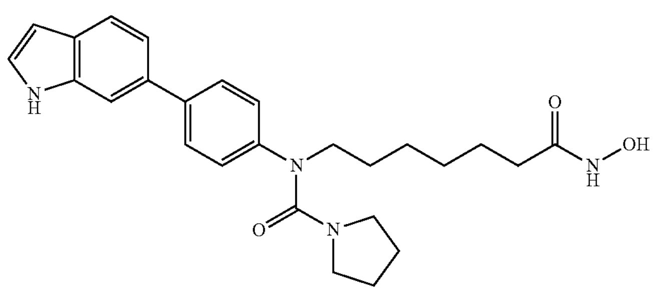 [SMILES: O=C(CCCCCCN(C(=O)N1CCCC1)c1ccc(-c2ccc3cc[nH]c3c2)cc1)NO] |

TABLE 12-continued
| Compound | Structure |
|---|---|
| 325 | 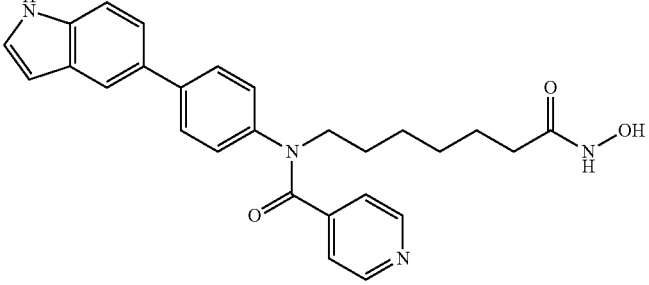 |
| 326 | 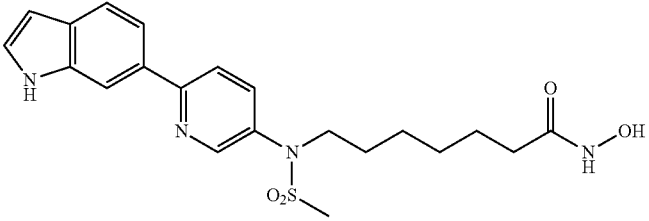 [SMILES: CS(=O)(=O)N(CCCCCCC(=O)NO)c1ccc(-c2ccc3cc[nH]c3c2)nc1] |
| 327 | 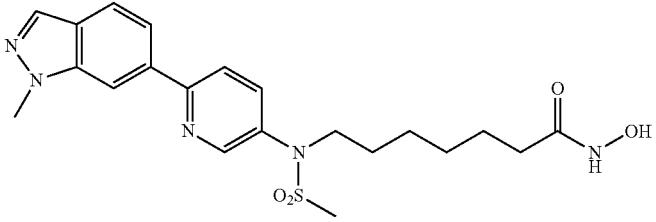 [SMILES: Cn1ncc2ccc(-c3ccc(N(CCCCCCC(=O)NO)S(C)(=O)=O)cn3)cc21] |
TABLE 13
| Compound | Structure |
|---|---|
| 328 | 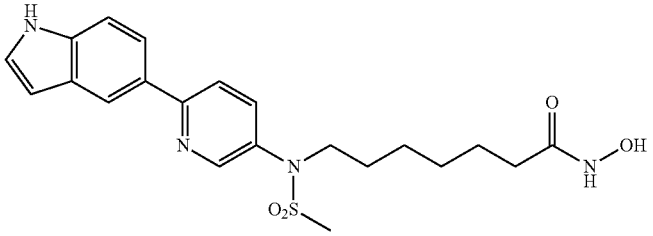 |
| 329 | 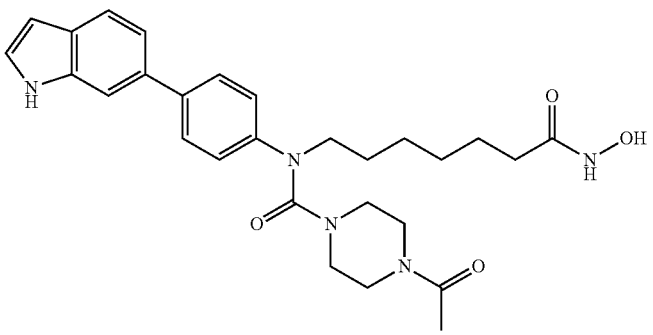 [SMILES: CC(=O)N1CCN(C(=O)N(CCCCCCC(=O)NO)c2ccc(-c3ccc4cc[nH]c4c3)cc2)CC1] |

TABLE 13-continued

| Compound | Structure |
|---|---|
| 330 | 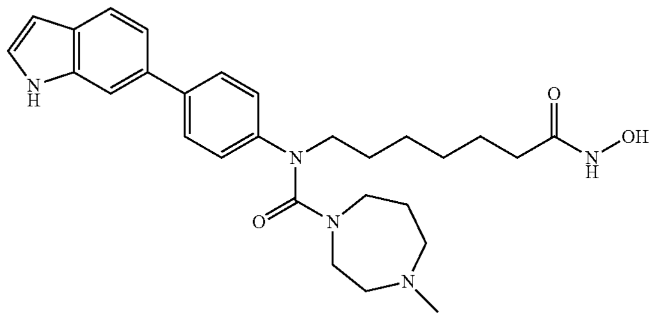 [SMILES: CN1CCCN(C(=O)N(CCCCCCC(=O)NO)c2ccc(-c3ccc4cc[nH]c4c3)cc2)CC1] |
| 331 | 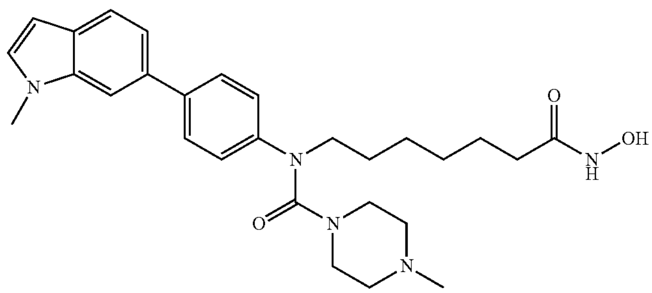 [SMILES: CN1CCN(C(=O)N(CCCCCCC(=O)NO)c2ccc(-c3ccc4ccn(C)c4c3)cc2)CC1] |
| 332 | 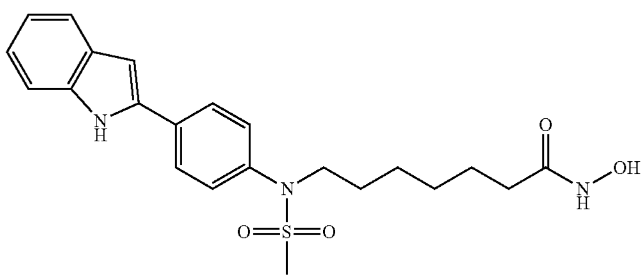 [SMILES: CS(=O)(=O)N(CCCCCCC(=O)NO)c1ccc(-c2cc3ccccc3[nH]2)cc1] |
| 333 | 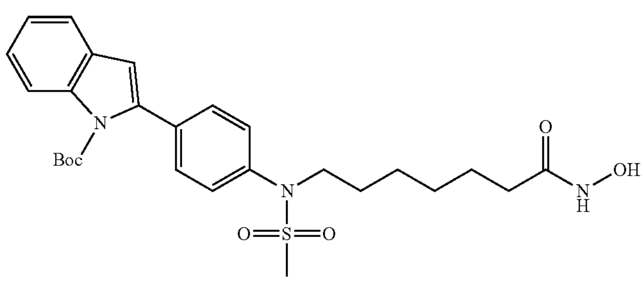 [SMILES: CC(C)(C)OC(=O)n1c(-c2ccc(N(CCCCCCC(=O)NO)S(C)(=O)=O)cc2)cc2ccccc21] |
| 334 | 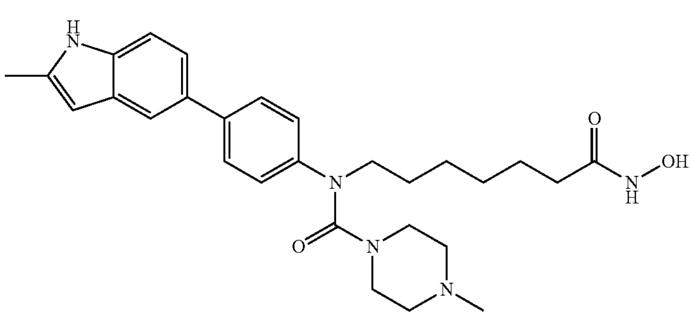 [SMILES: Cc1cc2cc(-c3ccc(N(CCCCCCC(=O)NO)C(=O)N4CCN(C)CC4)cc3)ccc2[nH]1] |

TABLE 13-continued
| Compound | Structure |
|---|---|
| 335 | 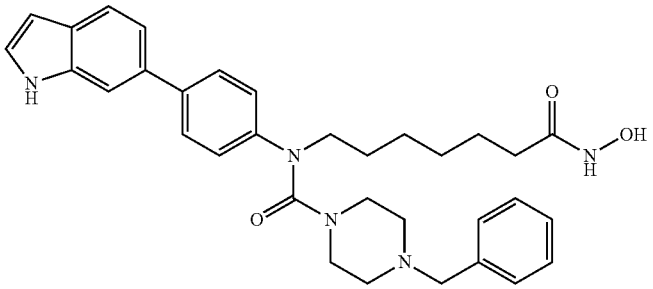 [SMILES: O=C(CCCCCCN(C(=O)N1CCN(Cc2ccccc2)CC1)c1ccc(-c2ccc3cc[nH]c3c2)cc1)NO] |
| 336 | 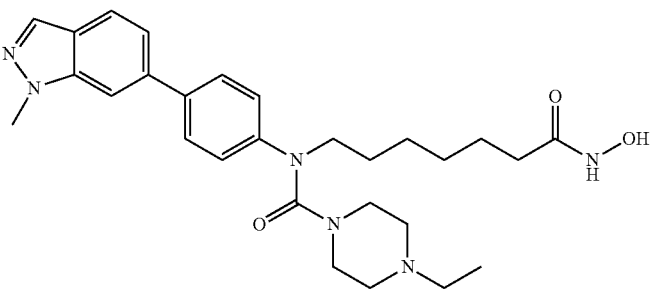 [SMILES: CCN1CCN(C(=O)N(CCCCCCC(=O)NO)c2ccc(-c3ccc4cnn(C)c4c3)cc2)CC1] |
| 337 | 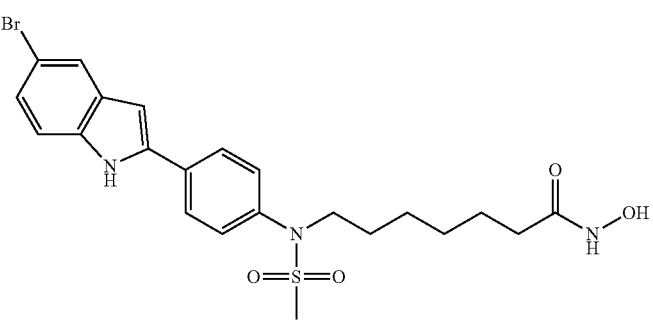 [SMILES: CS(=O)(=O)N(CCCCCCC(=O)NO)c1ccc(-c2cc3cc(Br)ccc3[nH]2)cc1] |
TABLE 14
| Compound | Structure |
|---|---|
| 338 | 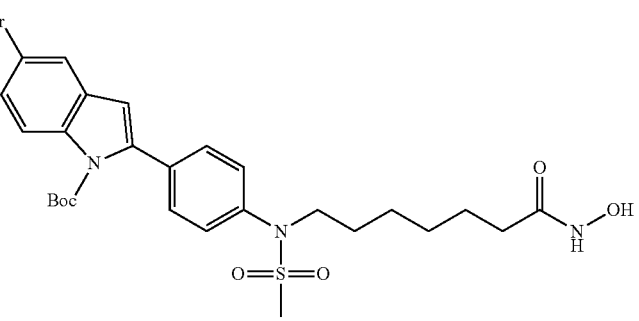 |

TABLE 14-continued
| Compound | Structure |
|---|---|
| 339 | 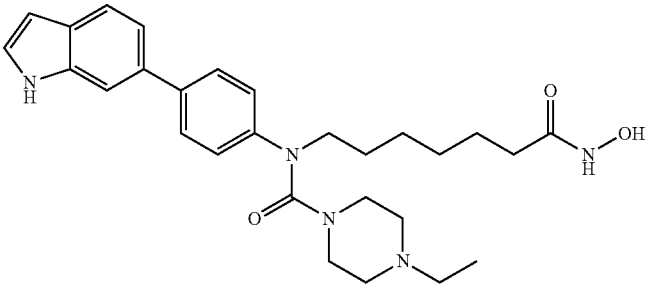 [SMILES: CCN1CCN(C(=O)N(CCCCCCC(=O)NO)c2ccc(-c3ccc4cc[nH]c4c3)cc2)CC1] |
| 340 | 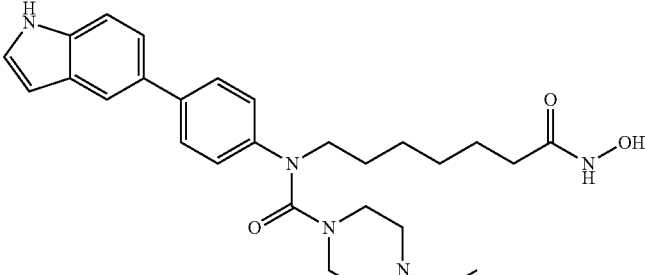 |
| 341 | 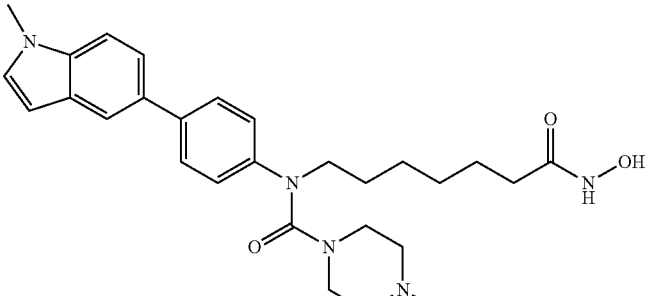 |
| 342 | 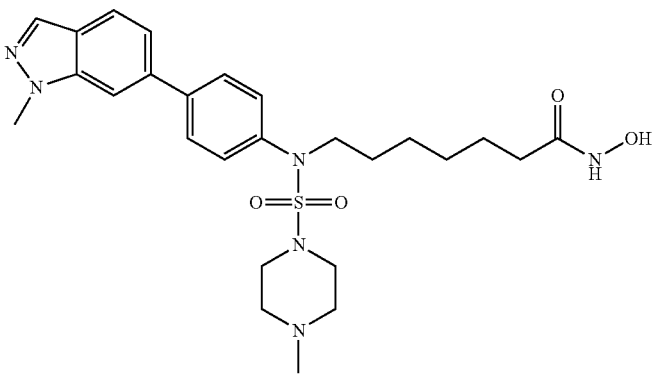 [SMILES: CN1CCN(S(=O)(=O)N(CCCCCCC(=O)NO)c2ccc(-c3ccc4cnn(C)c4c3)cc2)CC1] |

TABLE 14-continued
| Compound | Structure |
|---|---|
| 343 | 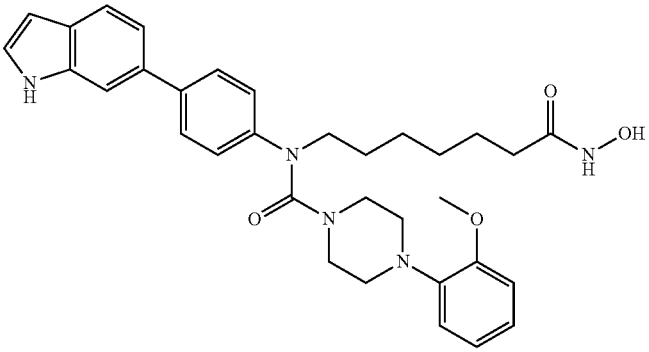 [SMILES: COc1ccccc1N1CCN(C(=O)N(CCCCCCC(=O)NO)c2ccc(-c3ccc4cc[nH]c4c3)cc2)CC1] |
| 344 | 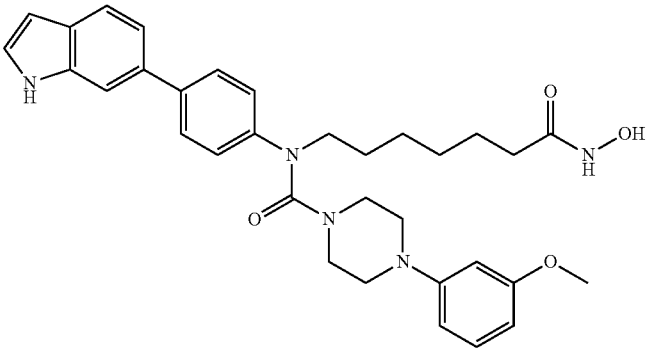 [SMILES: COc1cccc(N2CCN(C(=O)N(CCCCCCC(=O)NO)c3ccc(-c4ccc5cc[nH]c5c4)cc3)CC2)c1] |
| 345 | 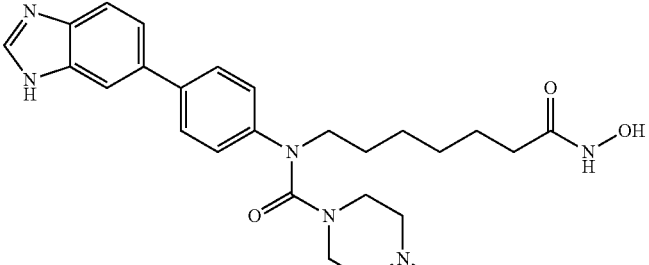 |
| 346 | 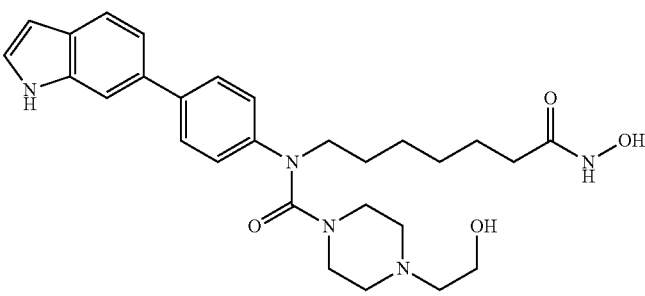 [SMILES: O=C(CCCCCCN(C(=O)N1CCN(CCO)CC1)c1ccc(-c2ccc3cc[nH]c3c2)cc1)NO] |
| 347 | 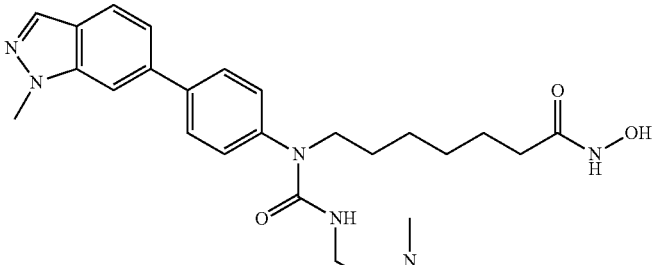 |

TABLE 15
| Compound | Structure |
|---|---|
| 348 | 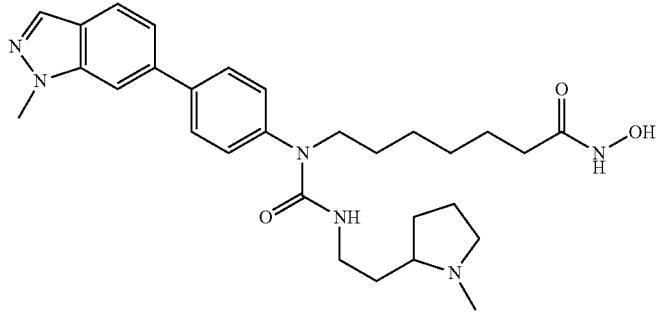 [SMILES: CN1CCCC1CCNC(=O)N(CCCCCCC(=O)NO)c1ccc(-c2ccc3cnn(C)c3c2)cc1] |
| 349 | 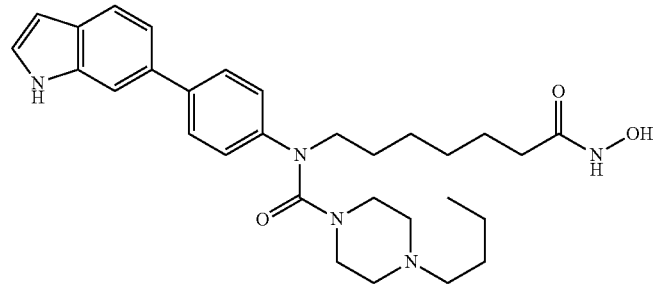 [SMILES: CCCCN1CCN(C(=O)N(CCCCCCC(=O)NO)c2ccc(-c3ccc4cc[nH]c4c3)cc2)CC1] |
| 350 | 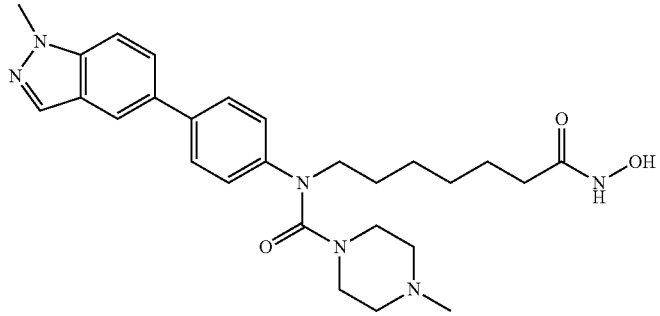 [SMILES: CN1CCN(C(=O)N(CCCCCCC(=O)NO)c2ccc(-c3ccc4c(cnn4C)c3)cc2)CC1] |
| 351 | 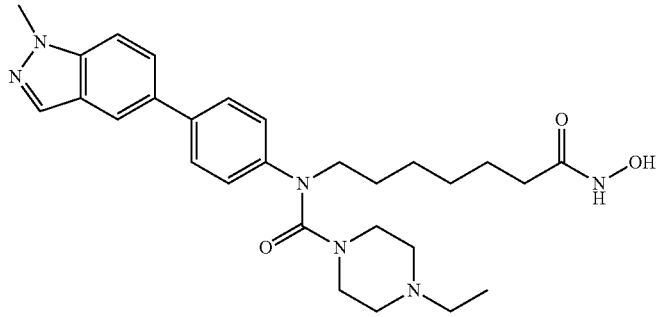 [SMILES: CCN1CCN(C(=O)N(CCCCCCC(=O)NO)c2ccc(-c3ccc4c(cnn4C)c3)cc2)CC1] |
| 352 | 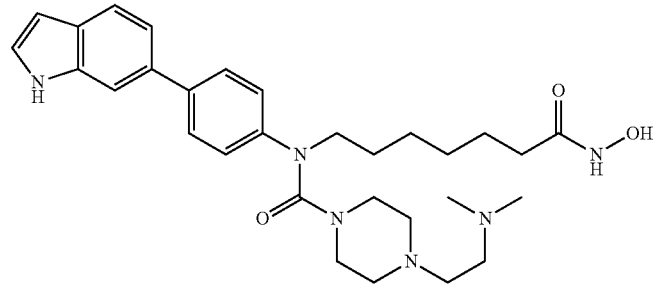 [SMILES: CN(C)CCN1CCN(C(=O)N(CCCCCCC(=O)NO)c2ccc(-c3ccc4cc[nH]c4c3)cc2)CC1] |

TABLE 15-continued
| Compound | Structure |
|---|---|
| 353 | 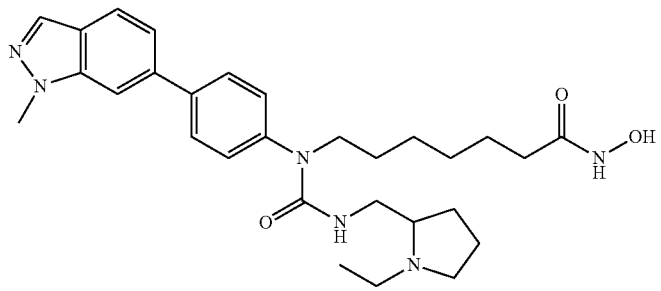 [SMILES: CCN1CCCC1CNC(=O)N(CCCCCCC(=O)NO)c1ccc(-c2ccc3cnn(C)c3c2)cc1] |
| 354 | 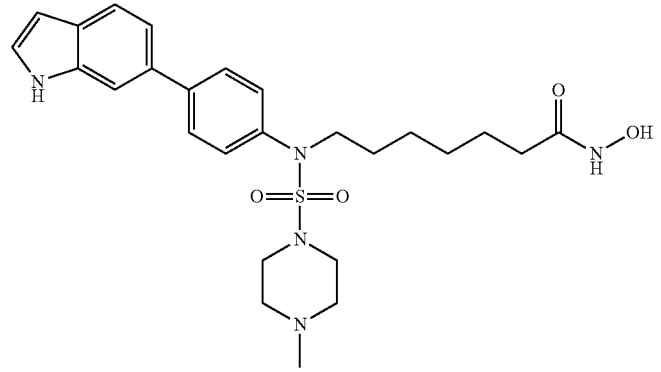 [SMILES: CN1CCN(S(=O)(=O)N(CCCCCCC(=O)NO)c2ccc(-c3ccc4cc[nH]c4c3)cc2)CC1] |
| 355 | 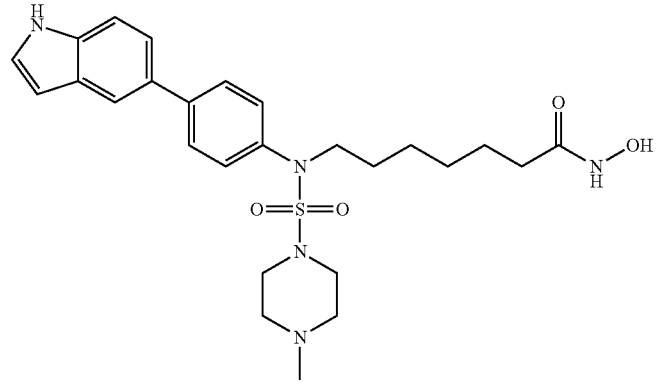 [SMILES: CN1CCN(S(=O)(=O)N(CCCCCCC(=O)NO)c2ccc(-c3ccc4[nH]ccc4c3)cc2)CC1] |
| 356 | 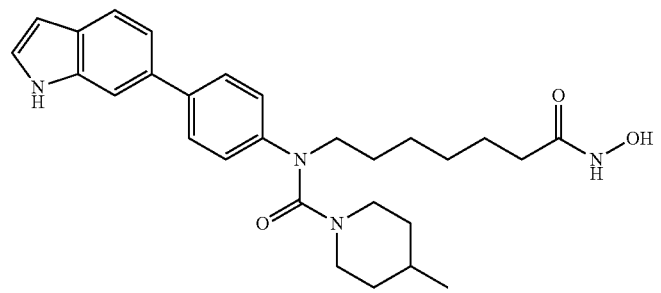 [SMILES: CC1CCN(C(=O)N(CCCCCCC(=O)NO)c2ccc(-c3ccc4cc[nH]c4c3)cc2)CC1] |

TABLE 15-continued

| Compound | Structure |
|---|---|
| 357 | 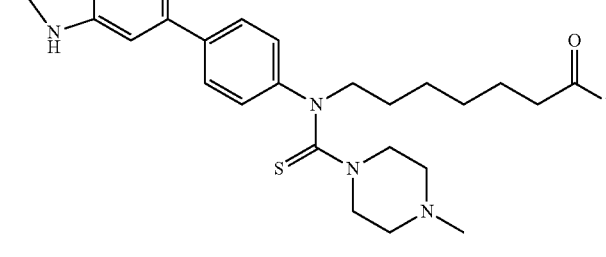 |
| 358 | 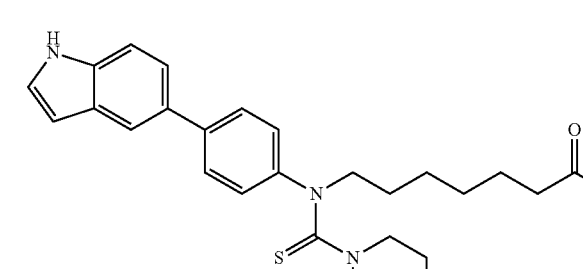 |
| 359 | 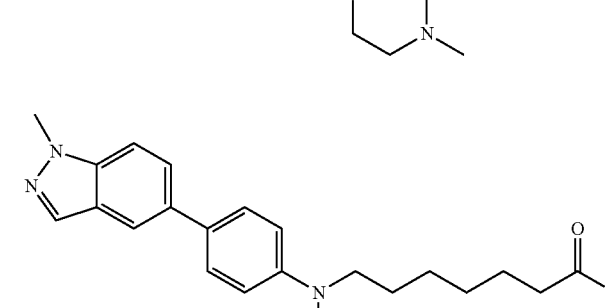 |

Measurement of Activities of Inventive Compounds—Experimental Protocols

1. Inhibitory Effect on Growth of HL60 Cell Line

In the culture of HL60 cells, 10% FBS-containing RPMI1640 medium was used Each of test substances was serially diluted in DMSO to a concentration of 10 mg/ml and serially diluted in PBS to a final concentration ranging from 100 µg/ml to 0.03 µg/ml. 20 µl (micro-liter) of each of the serially diluted test substances and 180 µl (micro-liter) of a medium containing $60 \times 10^4$ cells/ml were added to a 96-well plate and cultured under conditions of 37° C. and 5% $CO_2$ for 3 days. After completion of the culture, 50 µl (micro-liter) of a solution of 1.25 mg/ml MTT (3-(4,5-dimethylthiazol-2-yl)-2,5-diphenyltetrazolium bromide) in PBS was added to each well of the plate and incubated at 37° C. for 3 hours. The formed formazan crystal was dissolved in 150 µl (micro-liter) of DMSO, and the absorbance at 570 nm was measured.

The inhibitory effects ($IC_{50}$) of the selected compounds of the present invention on the growth of the HL60 cell line are shown in Table 16 below.

TABLE 16

| Compounds | HL-60 $IC_{50}$ (µM) |
|---|---|
| SAHA | 0.6~1.0 |
| PXD 101 | 0.1~0.2 |
| LBH 589 | 0.02~0.05 |
| 303, 306, 309, 334, 340 | 0.01~0.02 |
| 180, 181, 263, 264, 276, 305, 313, 314, 326, 328, 341, 342, 350, 351, 358, 359 | 0.02~0.05 |
| 211, 256, 260, 265, 267, 270, 275, 277, 284, 295, 296, 312, 327, 330, 336, 357 | 0.05~0.1 |

The inhibitory effects of the test substances on the growth of the HL60 cell line are indicated by $IC_{50}$ values. A lower $IC_{50}$ value indicates a better effect on the inhibition of HL60 cancer cells. As control drugs, SAHA (Merck), a currently commercially available anticancer agent, and LBH-589 (Novartis) and PXD-101 (Topo Target) that are not in clinical trials, were used. As can be seen from the results of evaluation of inhibitory effects shown in Table 16 above, all the tested compounds showed excellent inhibitory effects on the growth of cancer cells compared to SAHA, PXD 101 and LBH589, and the inhibitory effects of compounds 303, 306, 309, 334 and 340 were more than 50 times superior to that of SAHA, and more than 10 times superior to that of PXD 101.

2. Measurement of Effects Against HDAC Enzymes

To measure effects against HDAC enzymes, a kit (BIO-MOL International, LP) was used Each of test substances was dissolved in DMSO to a concentration of 10 mg/ml, and an assay buffer, an enzyme solution, a substrate and a staining reagent were prepared. The enzyme solution was a mixture of assay buffer (2/3) and Hela nuclear extract (1/3), and the substrate was a mixture of assay buffer (23/24) and substrate stock (1/24). Also, the staining reagent was a mixture of assay buffer (19/20), developer (1/20) and TSA (1/100). The assay buffer, the enzyme solution, the test substance and the substrate were added sequentially to a 96-well plate, stirred on a rocker for 3 minutes, and then incubated at 37° C. for 1 hour. After completion of the incubation, the staining reagent was added, and the mixture was stirred on a rocker for 1 minute and then incubated at 37° C. for 20 minutes (the staining reagent was mixed before addition). After completion of the incubation, air bubbles were removed from the 96-well plate, after which the absorbance at 405 nm was measured.

The HDAC inhibitory activities ($IC_{50}$) of the selected compounds of the present invention are shown in Table 17 below.

TABLE 17

| Compounds | HDAC $IC_{50}$ (µM) |
|---|---|
| SAHA | 0.2~0.5 |
| PXD 101 | 0.1~0.2 |
| LBH 589 | 0.01~0.05 |
| 263, 264, 279 | 0.001~0.01 |
| 284, 295, 296 | |
| 303, 305, 306 | |
| 309, 312, 313 | |
| 326, 327, 328 | |
| 334, 336, 340 | |
| 341, 342, 350 | |
| 351, 357, 358 | |
| 359 | |
| 180, 181, 211 | 0.01~0.05 |
| 256, 260, 267 | |
| 277 | |
| 265 | 0.05~0.1 |
| 270 | |
| 275 | |

The HDAC inhibitory activities of the test substances are indicated by $IC_{50}$ values. A lower $IC_{50}$ value indicates a better inhibitory effect against HDAC enzymes. As can be seen in Table 17 above, all the compounds of the present invention showed excellent inhibitory effects on the growth of cancer cells compared to SAHA and PXD 101, and the HDAC inhibitory activities of compounds 263, 264, 279, 284, 295, 303, 305, 306, 309, 312, 313, 326, 327, 328, 334, 336, 340, 341, 342, 350, 351, 357, 358 and 359 were more than 100 times higher than those of SAHA and PXD 101 and were more than 10 times higher than that of LBH 589 known to have the highest HDAC inhibitory activity.

3. Test Examples

Pharmaceutical Effects of Inventive Compounds on Mice (1) Test Animals

Male BALB/c nude mice (4-week old) used in human tumor transplantation studies were purchased from Central Animal Laboratory Inc. (Korea) or Orient Bio Inc. (Korea). The animals were permitted ad libitum access to sterile feed and water in a sterile breeding system at 23+0.5° C.

(2) Cell Lines

For use in tumor transplantation studies, the human cancer cell lines HCT116 (human colorectal carcinoma, CCL-247), PC-3 (human prostate adenocarcinoma, CRL-1435), and A549 (human lung carcinoma, CCL-185) were purchased from ATCC (American Type Culture Collection, Rockville, Md., USA).

HCT116 cells were cultured in an air incubator under conditions of 37° C. and 5% $CO_2$ using McCoy'SA medium (Gibco BRL) containing 10% heat-inactivated fetal bovine serum (Gibco BRL) and 1% antibiotics-antymycotics (Gibco BRL). Cell lines other than the HCT116 cell line were cultured in an air incubator under conditions of 37° C. and 5% $CO_2$ using RPM1640 medium (Gibco BRL) containing 10% heat-inactivated fetal bovine serum (Gibco BRL) and 1% antibiotics-antymycotics (Gibco BRL).

(3) In Vivo Anticancer Activity

Studies on the in vivo transplantation of human cancer cells were carried out in the following manner. Human cancer cells (HCT116, PC-3, and A549) that proliferated in vitro were injected subcutaneously into the abdominal region of BALB/c nude mice and allowed to proliferate in vivo. 20-25 days after the injection, the mice were sacrificed by cervical dislocation, and the solid cancer that proliferated in each of the mice was isolated aseptically, and connective or necrotic tissue and skin was removed therefrom, thus collecting a fresh cancer tissue. 50 mg of a fragment was taken aseptically from the cancer tissue and inserted into a 16-gauge trocar which was then transplanted subcutaneously into the upper abdominal region of mice.

15-30 days after the human cancer cell lines have been transplanted into the BALB/c nude mice, only mice in which the cancer cells have proliferated to a given size were selected and used in the experiment. When the tumor size in each of the test groups reached 100-200 $mm^3$ after cancer cell transplantation, the experiment was started.

With respect to solvents used for the drugs upon abdominal administration, compounds 312, 334 and 336 were dissolved in saline, and LBH 589 and PXD 101 were dissolved in a mixture of cremophor:ethanol:saline (1:1:8), and each of the drugs was injected at a dose of 0.1 ml per 10 g of mouse bodyweight according to each administration schedule. SAHA was dissolved in DMSO and injected at a dose of 10 microliter per 10 g of mouse bodyweight.

For oral administration, all the drugs were dissolved in 0.5% MC as a solvent and administered at a dose of 0.1 ml per 10 g of mouse bodyweight. The anticancer effect of each drug was evaluated based on the inhibition rate (IR %) of tumor volume that indicates the tumor volume at reference date in comparison with control groups. As the control drugs, commercially available anticancer drugs, SAHA (Merck), LBH-589 (Novartis), PXD-101 (Topo Target) and MGCD 0103 (Methylgene), were used in the evaluation.

Tumor size=(short diameter)×(long diameter)/2

I.R.(%)=[1−(mean tumor size of drug-administered group)/(mean tumor size of control group)]×100

TABLE 18

| Group (n = 10) | Dose(/day) | Schedule | IR (%) |
|---|---|---|---|
| SAHA | 100 mg/kg | qd x 5 | 46 |
| PXD 101 | 80 mg/kg | 2 wks | 38 |
| LBH 589 | 5 mg/kg | ip | 40 |
|  | 10 mg/kg |  | 65 |
| Compound 312 | 20 mg/kg |  | 51 |
|  | 40 mg/kg |  | 58 |
|  | 60 mg/kg |  | 70 |
|  | 80 mg/kg |  | 81 |

In this experiment, inhibitory effects against actual colon cancer cells (HCT 116), and the measurement results (IR(%) and tumor volume (mm)) are shown in Table 18 above. A higher IR(%) value and a smaller tumor volume value indicate a better inhibitory effect against cancer cells. The drug administration schedule consisted of daily administration for 5 consecutive days, followed by a drug-rest interval of 2 days, for a total of 2 weeks. The test substances were compared with control groups, commercially available SAHA (Merck), and PXD 101 (Topo Target) and LBH 589 (Novartis), which are now in clinical trials. As a result, compound 312 showed excellent colon cancer inhibitory effects over the entire dose range compared to the highest doses of SAHA and PXD 101, and showed excellent colon cancer inhibitory effects at doses of 60 and 80 mg/kg compared to the highest dose of LBH 589 having the most excellent inhibitory effect among the control groups. The maximum tolerated doses (MTDs) of the drugs were 100 mg/kg for SAHA, 80 mg/kg for PXD, and 10 mg/kg for LBH 589. At doses higher than maximum tolerated doses, the animals were dead due to toxicity.

TABLE 19

| Group (n = 10) | Dose(/day) | Schedule | IR (%) |
|---|---|---|---|
| LBH 589 | 5 mg/kg | qd x 5 | 40 |
|  | 10 mg/kg | 2 wks | 65 |
| Compound 334 | 40 mg/kg | ip | 47 |
|  | 60 mg/kg |  | 66 |
| Compound 336 | 40 mg/kg |  | 56 |
|  | 60 mg/kg |  | 75 |
|  | 80 mg/kg |  | 78 |

In this experiment, inhibitory effects against actual colon cancer cells (HCT 116) were measured. The drug administration schedule consisted of daily administration for 5 consecutive days, followed by a drug-rest interval of 2 days, for a total of 2 weeks. As a control group, LBH 589 (Novartis) known to have the most excellent inhibitory effect was used. As can be seen in Table 19, compounds 334 and 336 showed excellent inhibitory effects on colon cancer compared to the control compound LBH 589. In this experiment, the maximum tolerated doses (MTDs) of the drugs were 10 mg/kg for LBH 589, 60 mg/kg for compound 334, and 80 mg/kg for compound 336. At doses higher than maximum tolerated doses, the animals were dead due to toxicity.

TABLE 20

| Group (n = 4) | Dose(/day) | Schedule | IR (%) |
|---|---|---|---|
| LBH 589 | 10 mg/kg | qd x 5, 3 wks | 58 |
| Compound 312 | 60 mg/kg | b.i.wk(Mon, Thu) | 50 |
|  | 80 mg/kg | 3 wks | 56 |
|  | 100 mg/kg | ip | 71 |

Figure 3:
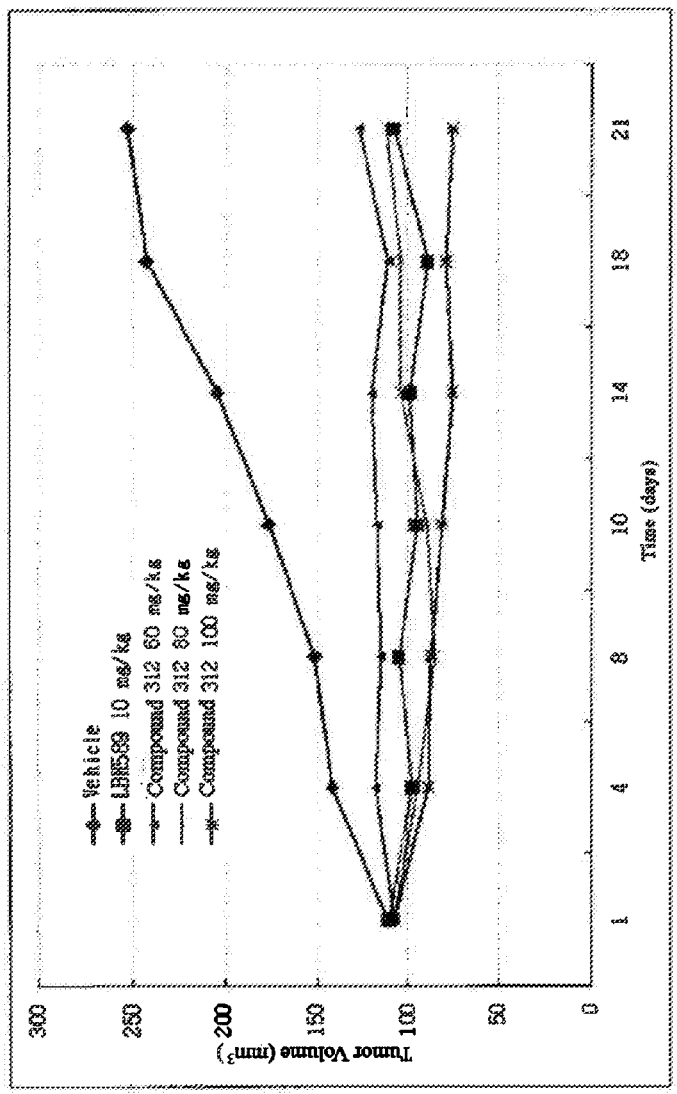

In this experiment, anticancer effects against non-small cell lung cancer (A549) were measured. In the administration schedule, compound 312 was administered twice (Monday and Thursday) a week for 3 weeks, and as a control group for comparison, LBH 589(Novartis) known to have the most excellent anticancer effect was administered five times a week, followed by a drug-rest interval of 2 days, for a total of 3 weeks. As can be seen from the results in FIG. 3, compound 312 was convenient to administer, because it showed an excellent inhibitory effect against non-small cell lung cancer (A549) even when it was administered twice a week. LBH 589 did not show a cancer inhibitory effect when it was administered twice a week.

TABLE 21

| Group (n = 4) | Dose(/day) | Schedule | IR (%) |
|---|---|---|---|
| LBH 589 | 10 mg/kg | qd x 5, 3 wks | 48 |
| Compound 312 | 60 mg/kg | b.i.wk(Mon, Thu) | 39 |
|  | 80 mg/kg | 3 wks | 39 |
|  | 100 mg/kg | ip | 59 |

Figure 4:
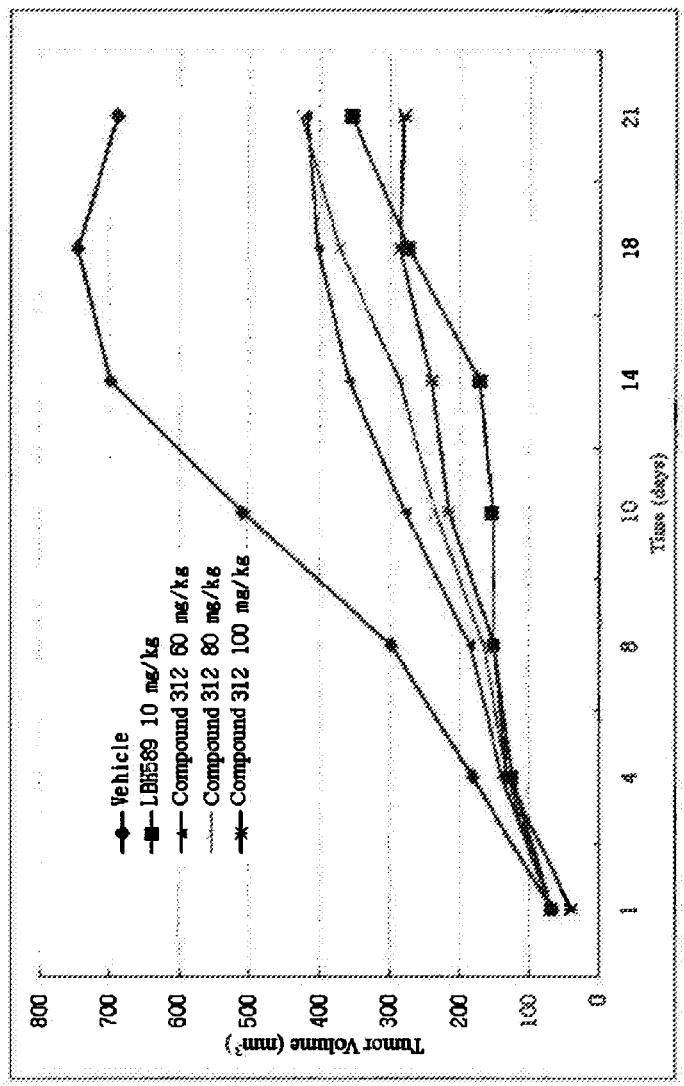

In this experiment, anticancer effects against prostate cancer (PC-3) were measured. In the drug administration schedule, compound 312 was administered twice (Monday and Thursday) a week for 3 weeks, and as a control group for comparison, LBH 589(Novartis) was administered five times a week, followed by a drug-rest interval of 2 days, for a total of 3 weeks. As can be seen from the results in FIG. 4, compound 312 was convenient to administered to administer and had excellent inhibitory effects against prostate cancer (PC-3), compared to the control compound LBH 589.

TABLE 22

| Group (n = 6) | Dose(/day) | Schedule | IR (%) |
|---|---|---|---|
| LBH 589 | 50 mg/kg | qd x 5, 3 wks | 0 |
| MGCD 0103 | 120 mg/kg | p.o | 50 |
| SAHA | 200 mg/kg |  | 26 |
| Compound 312 | 150 mg/kg | b.i.wk(Mon, Thu) | 52 |
|  | 180 mg/kg | 3 wks | 55 |
|  | 210 mg/kg | p.o | 69 |

Figure 5:
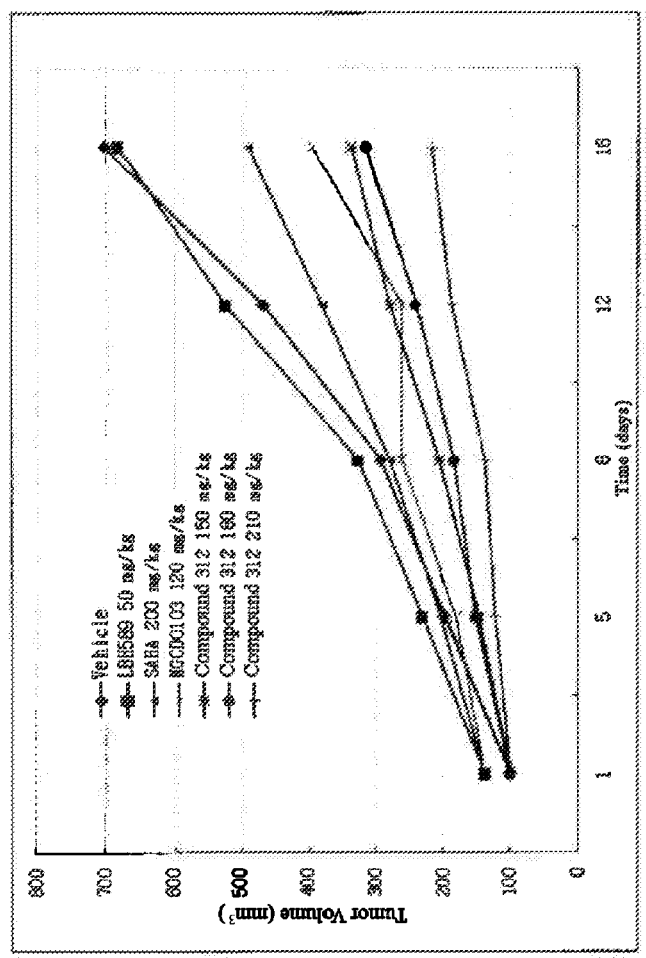

In this experiment, in order to develop anticancer drugs for oral (p.o) administration, cancer inhibitory effects against colon cancer (HCT116) upon oral administration were measured. In the drug administration schedule, compound 312 was administered orally twice (Monday and Thursday) a week for 3 weeks, and as a control group for comparison, LBH 589(Novartis) was administered orally five times a week, followed by a drug-rest interval of 2 days, for a total of 3 weeks. Also, SAHA, LBH 589, and MGCD 0103 having excellent anticancer effects upon oral administration were used as control groups for comparison. As can be seen from the results in FIG. 5, compound 312 was convenient to administered and showed an excellent inhibitory effect against colon cancer (HCT116), compared to the control compounds LBH 589, SAHA and MGCD0103.

4. P450 (CYP3A4) Inhibitory Activity

P450 (CYP3A4) is a metabolic enzyme, and non-inhibition of the enzyme by a test compound means that the test substance has a low possibility of causing side effects by interaction with other drugs. Each of compounds used in the test was dissolved in DMSO (10 mg/ml), and the dilution of each test substance to $2 \times 10^{-2}$ mg/ml was additionally performed in 200 μl (micro-liter) of a test system containing an assay buffer. The final solvent concentration was not higher than 2%. The CYP3A4 protein inhibitory test system included a total assay volume (100 µl (micro-liter)) of a NADPH production system (3.3 mM glucose-6-phosphate, 0.4 units/ml glucose-6-phosphate dehydrogenase, 1.3 mM NADP+ and 3.3 mM MgCl$_2$.6H$_2$O in assay buffer) and a test compound in each well of a 96-well plate. After pre-incubation at 37° C. for 10 minutes, 100 µl (micro-liter) of a KPO4 assay buffer containing 1.0 µmol P450 protein and 50 uM BFC (7-benzyloxy-trifluoromethylcoumarin) fluorescent probe substrate was added to the test system, and an enzyme reaction in the test system having a total assay volume of 200 µl (micro-liter) was initiated. After the test system has been incubated at 37° C. for 30 minutes, 75 µl (micro-liter) of Tris base (0.5M Tris base 18 ml+72 ml acetonitrile) containing acetonitrile was added thereto to terminate the reaction. Irradiation with fluorescence was carried out at an excitation wavelength of 409 nm and an emission wavelength of 530 nm. As a reference compound, ketoconazole (IC$_{50}$=5×10$^{-8}$ M) was used in this experiment.

Figure 6:
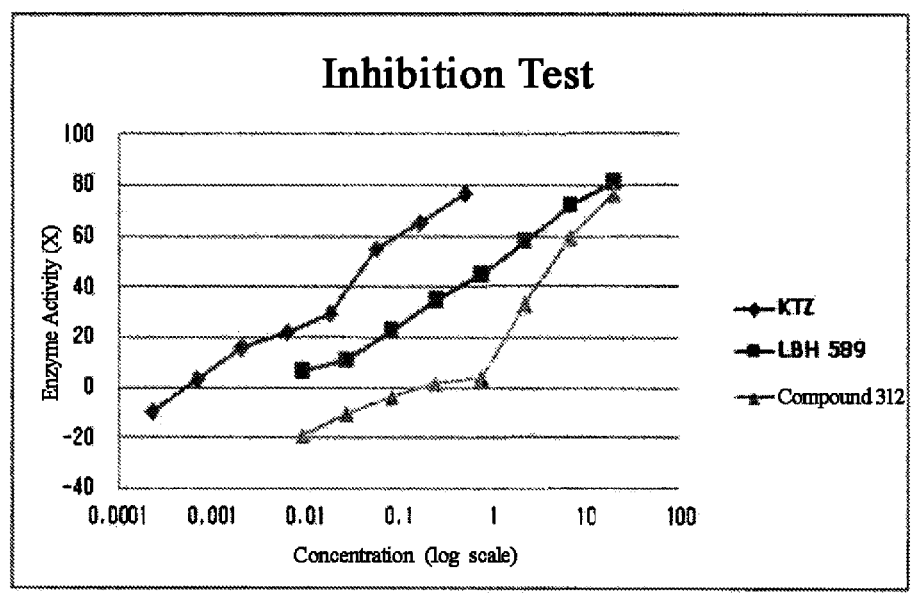
FIG. 6 shows the results of measuring the P450 (CYP3A4) inhibitory activity of a compound according to the present invention.

In this experiment, compound 312 was compared with the control compounds ketoconazole and LBH 589. The results are shown in FIG. 6, and as can be seen therein, compound 312 did not inhibit P450 3A4 in vivo, and the P450 3A4 inhibitory activity thereof was lower than that of LBH 589 having excellent anticancer effects, suggesting that compound 312 has a low possibility of causing side effects by interaction with other drugs.

INDUSTRIAL APPLICABILITY

As described above, the hydroxamate derivatives of the present invention have histone deacetylase inhibitory activity and kill the actively proliferating cells of malignant tumors. Thus, the hydroxamate derivatives of the present invention can be used as agents for treating malignant tumors, viral and bacterial infections, vascular restenosis, inflammatory diseases, autoimmune diseases, and psoriasis.

The invention claimed is:

1. A hydroxamate compound of the following formula I, an isomer, pharmaceutically acceptable salt or hydrate thereof,

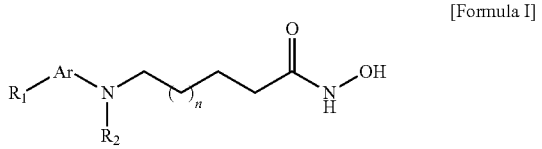

[Formula I]

wherein n is an integer of 2, 3 or 4;

Ar is a phenyl, pyridine or pyrimidine group which is unsubstituted or substituted with one or more substituents selected from the group consisting of C$_{1-6}$ alkyl, amino, nitro, thiomethyl, hydroxyl, nitrile, carboxyl, C$_{1-4}$ alkyloxy, aryl C$_{1-4}$ alkyloxy, halogen, trifluoromethyl, —O—CF$_3$, phenyl and phenoxy groups;

R$_1$ is an indole, indazole or benzimidazole group, which is unsubstituted or substituted with one or more substituents selected from the groups consisting of C$_{1-6}$ alkyl, formyl, amino, nitro, thiomethyl, hydroxyl, C$_{1-6}$ alkoxy, nitrile, carboxyl, halogen, trifluoromethyl, —O—CF$_3$, —C(O)—R$_5$, —S(O$_2$)—R$_5$ and

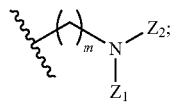

and

R$_2$ is hydrogen, hydroxy C$_{1-6}$ alkyl, C$_{1-8}$ alkyl, —C(O)—R$_5$, —C(O)NH—R$_5$, —S(O$_2$)—R$_5$, —C(S)—R$_5$ or —C(O$_2$)—R$_5$, in which R$_5$ is

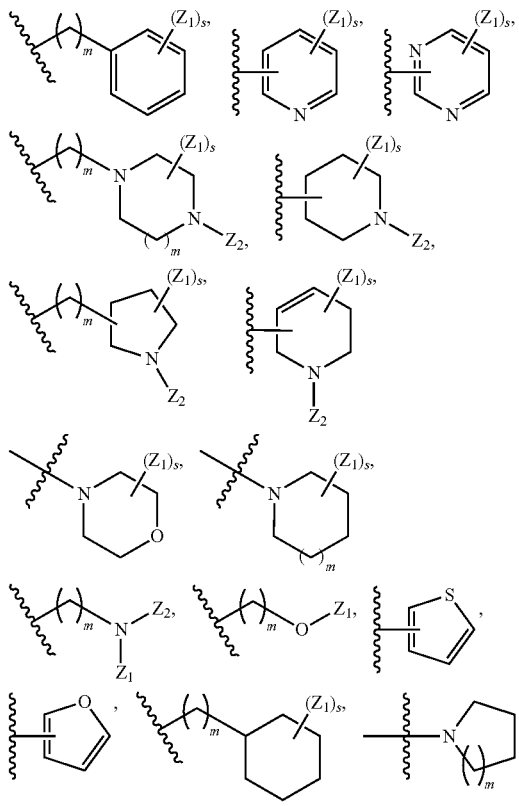

naphthyl, C$_{1-8}$ alkyl or C$_{1-4}$ alkyloxy group, Z$_1$ and Z$_2$ are each independently hydrogen, C$_{1-6}$ alkyl, amino, —O—C$_{1-4}$ alkyl, —S(O$_2$)C$_{1-4}$ alkyl, —C(O)C$_{1-4}$ alkyl, —S—C$_{1-4}$ alkyl, halogen, trifluoromethyl, —O—CF$_3$, phenyl, —O-phenyl, —O—C$_{1-4}$ alkylaryl,

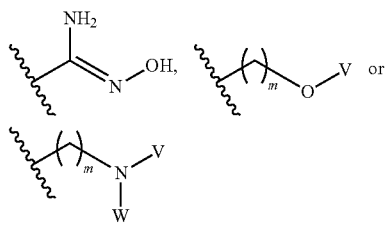

V and W are each independently hydrogen or C$_{1-6}$ alkyl,
Each s is independently an integer of 0, 1, 2, 3, 4 or 5, and
Each m is independently an integer of 0, 1, 2 or 3.

2. The hydroxamate compound of formula I, isomers thereof, pharmaceutically acceptable salts thereof, or hydrates thereof according to claim 1, wherein R$_1$ is an indole or indazole group which is unsubstituted or substituted with one or more substituents selected from the group consisting of $C_{1-6}$ alkyl, formyl, amino, nitro, thiomethyl, hydroxy, $C_{1-6}$ alkoxy, nitrile, carboxy, halogen, trifluoromethyl, —O—$CF_3$, —C(O)—$R_5$, —S($O_2$)—$R_5$ and

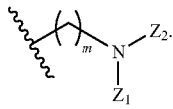

3. The hydroxamate compound of formula I, isomers thereof, pharmaceutically acceptable salts thereof, or hydrates thereof according to claim 2, wherein Ar is a phenyl group which is unsubstituted or substituted with one or more substituents selected from the group consisting of $C_{1-6}$ alkyl, amino, nitro, thiomethyl, hydroxyl, nitrile, carboxyl, $C_{1-4}$ alkyloxyl, aryl $C_{1-4}$ alkyloxy, halogen, trifluoromethyl, —O—$CF_3$, phenyl and phenoxy groups.

4. The hydroxamate compound of formula I, isomers thereof, pharmaceutically acceptable salts thereof, or hydrates thereof according to claim 3, wherein n is 3, Ar is an unsubstituted phenyl group, $R_1$ is an indole or indazole group which is substituted with hydrogen or one or more $C_{1-6}$ alkyl groups, and $R_2$ is hydrogen, —C(O)—$R_5$ or —S($O_2$)—$R_5$, in which $R_5$ is

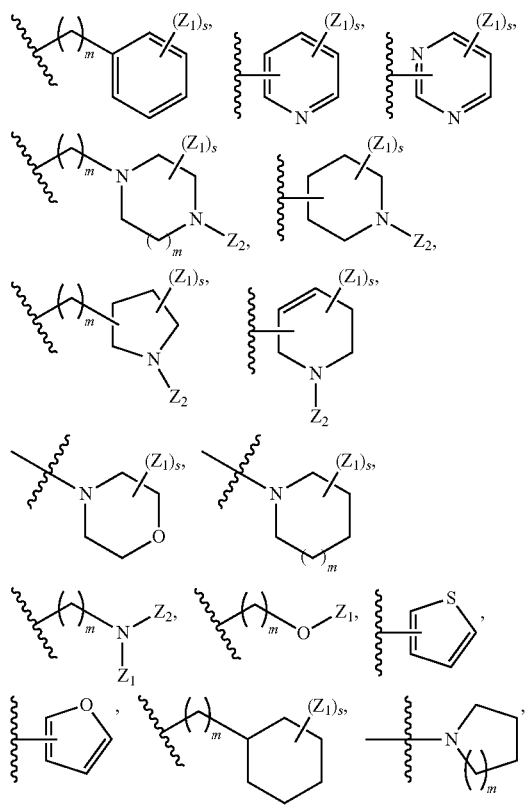

naphthyl, $C_{1-8}$ alkyl or $C_{1-4}$ alkyloxy group, $Z_1$ and $Z_2$ are each independently hydrogen, $C_{1-6}$ alkyl, amino, —O—$C_{1-4}$ alkyl, —S($O_2$)$C_{1-4}$ alkyl, —C(O)$C_{1-4}$ alkyl, —S—$C_{1-4}$ alkyl, halogen, trifluoromethyl, —O—$CF_3$, phenyl, —O-phenyl, —O—$C_{1-4}$ alkylaryl,

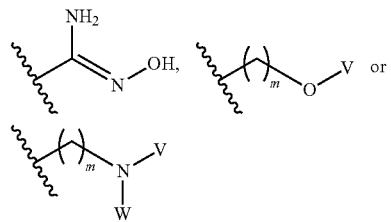

V and W are each independently hydrogen or $C_{1-6}$ alkyl, Each s is independently an integer of 0, 1, 2, 3, 4 or 5, and Each m is independently an integer of 0, 1, 2 or 3.

5. The hydroxamate compound of formula I, isomers thereof, pharmaceutically acceptable salts thereof, or hydrates thereof according to claim 4, wherein n is 3, Ar is an unsubstituted phenyl group, $R_1$ is an indole or indazole group which is substituted with hydrogen or one or more $C_{1-6}$ alkyl groups, and $R_2$ is hydrogen, —C(O)—$R_5$ or —S($O_2$)—$R_5$, in which $R_5$ is

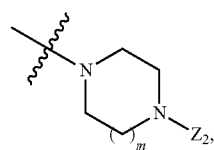

in which $Z_2$ is hydrogen or $C_{1-6}$ alkyl, and m is an integer of 0, 1, 2 or 3.

6. The hydroxamate compound, isomers thereof, pharmaceutically acceptable salts thereof, or hydrates thereof according to claim 1, wherein the hydroxamate compound is selected from the group consisting of the following compounds:

7-(4-(1H-indol-5-yl)phenylamino)-N-hydroxyheptanamide;
N-hydroxy-7-(4-(1-methyl-1H-indol-5-yl)phenylamino) hydroxyheptanamide;
7-(3-(1H-indol-6-yl)phenylamino)-N-hydroxyheptanamide;
7-(4-(1H-indol-6-yl)phenylamino)-N-hydroxyheptanamide;
7-(3-(1H-indol-5-yl)phenylamino)-N-hydroxyheptanamide;
7-(4-(1H-indol-4-yl)phenylamino)-N-hydroxyheptanamide;
7-(2-(1H-indol-5-yl)phenylamino)-N-hydroxyheptanamide;
7-(5-(1H-indol-6-yl)pyridin-2-ylamino)-N-hydroxyheptanamide;
7-(6-(1H-indol-6-yl)pyridin-3-ylamino)-N-hydroxyheptanamide;
7-(3-(1H-indol-7-yl)phenylamino)-N-hydroxyheptanamide;
7-(5-(1H-indol-6-yl)pyrimidin-2-ylamino)-N-hydroxyheptanamide;
7-(4-(1H-indol-7-yl)phenylamino)-N-hydroxyheptanamide;
N-(4-(1H-indol-6-yl)phenyl)-N-(7-(hydroxyamino)-7-oxoheptyl)-4-methoxybenzamide;
N-(4-(1H-indol-6-yl)phenyl)-N-(7-(hydroxyamino)-7-oxoheptyl)nicotinamide;
7-(N-(4-(1H-indol-6-yl)phenyl)-2-phenylacetamido)-N-hydroxyheptanamide;

phenyl 4-(1H-indol-6-yl)phenyl(7-(hydroxyamino)-7-oxoheptyl)carbamate;
benzyl 4-(1H-indol-6-yl)phenyl(7-(hydroxyamino)-7-oxoheptyl)carbamate;
7-((4-(1H-indol-6-yl)phenyl)(2-hydroxyethyl)amino)-N-hydroxyheptanamide;
N-hydroxy-7-(4-(1-(phenylsulfonyl)-1H-indol-2-yl)phenylamino)heptanamide;
7-(N-(4-(1H-indol-6-yl)phenyl)thiophene-2-sulfonamido)-N-hydroxyheptanamide;
N-(4-(1H-indol-6-yl)phenyl)-N-(7-(hydroxyamino)-7-oxoheptyl)furan-2-carboxamide;
7-(N-(4-(1H-indol-6-yl)phenyl)-4-methoxyphenylsulfonamido)-N-hydroxyheptanamide;
N-(4-(1H-indol-5-yl)phenyl)-N-(7-(hydroxyamino)-7-oxoheptyl)-4-methoxybenzamide;
N-(4-(1H-indol-6-yl)phenyl)-N-(7-(hydroxyamino)-7-oxoheptyl)-4-methylbenzamide;
7-(N-(4-(1H-indol-6-yl)phenyl)phenylsulfonamido)-N-hydroxyheptanamide;
N-(4-(1H-indol-6-yl)phenyl)-N-(7-(hydroxyamino)-7-oxoheptyl)picolinamide;
N-(4-(1H-indol-6-yl)phenyl)-N-(7-(hydroxyamino)-7-oxoheptyl)-3-methoxybenzamide;
N-(4-(1H-indol-6-yl)phenyl)-N-(7-(hydroxyamino)-7-oxoheptyl)-3,4,5-trimethylbenzamide;
N-(4-(1H-indol-6-yl)phenyl)-4-(dimethylamino)-N-(7-(hydroxyamino)-7-oxoheptyl)benzamide;
7-(N-(4-(1H-indol-6-yl)phenyl)-2-aminoacetamido)-N-hydroxyheptanamide;
N-(4-(1H-indol-6-yl)phenyl)-6-chloro-N-(7-(hydroxyamino)-7-oxoheptyl)nicotinamide;
N-(4-(1H-indol-6-yl)phenyl)-N-(7-(hydroxyamino)-7-oxoheptyl)isonicotinamide;
(Z)-N-(4-(1H-indol-6-yl)phenyl)-N-(7-(hydroxyamino)-7-oxoheptyl)-4-(N'-hydroxycarbamimidoyl)benzamide;
N-(4-(1H-indol-6-yl)phenyl)-2,6-difluoro-N-(7-(hydroxyamino)-7-oxoheptyl)benzamide;
N-(4-(1H-indol-6-yl)phenyl)-4-fluoro-N-(7-(hydroxyamino)-7-oxoheptyl)benzamide;
N-(4-(1H-indol-6-yl)phenyl)-N-(7-(hydroxyamino)-7-oxoheptyl)-6-(trifluoromethyl)nicotinamide;
6-(4-(1H-indol-6-yl)phenylamino)-N-hydroxyhexanamide;
8-(4-(1H-indol-6-yl)phenylamino)-N-hydroxyoctanamide;
N-(4-(1H-indol-6-yl)phenyl)-4-ethoxy-N-(7-(hydroxyamino)-7-oxoheptyl)benzamide;
7-((4-(1H-indol-6-yl)phenyl)(benzyl)amino)-N-hydroxyheptanamide;
N-(4-(1H-indol-6-yl)phenyl)-2,4,6-trifluoro-N-(7-(hydroxyamino)-7-oxoheptyl)benzamide;
N-(4-(1H-indol-6-yl)phenyl)-4-amino-N-(7-(hydroxyamino)-7-oxoheptyl)benzamide;
N-(4-(1H-indol-6-yl)phenyl)-N-(7-(hydroxyamino)-7-oxoheptyl)piperidin-1-carboxamide;
N-(4-(1H-indol-6-yl)phenyl)-N-(7-(hydroxyamino)-7-oxoheptyl)-4-methoxy-3-(trifluoromethyl)benzamide;
N-(4-(1H-indol-6-yl)phenyl)-N-(7-(hydroxyamino)-7-oxoheptyl)-4-(trifluoromethyl)benzamide;
N-(4-(1H-indol-6-yl)phenyl)-N-(7-(hydroxyamino)-7-oxoheptyl)-3,4-dimethoxybenzamide;
7-(N-(4-(1H-indol-6-yl)phenyl)-3,4-dimethoxyphenylsulfonamido)-N-hydroxyheptanamide;
7-(N-(4-(1H-indol-6-yl)phenyl)-4-(methylsulfonyl)phenylsulfonamido)-N-hydroxyheptanamide;
7-(4-(1H-indol-6-yl)-3-(trifluoromethyl)phenylamino)-N-hydroxyheptanamide;
N-(4-(1H-indol-6-yl)-3-(trifluoromethyl)phenyl)-N-(7-(hydroxyamino)-7-oxoheptyl)nicotinamide;
7-(N-(4-(1H-indol-6-yl)phenyl)naphthalene-2-sulfonamido)-N-hydroxyheptanamide;
N-(4-(1H-indol-6-yl)-3-methylphenyl)-N-(7-(hydroxyamino)-7-oxoheptyl)-4-methoxybenzamide;
7-(1-(4-(1H-indol-6-yl)phenyl)-3-(4-methoxyphenyl)ureido)-N-hydroxyheptanamide;
7-(1-(4-(1H-indol-6-yl)phenyl)-3-(3-methoxyphenyl)ureido)-N-hydroxyheptanamide;
7-(N-(4-(1H-indol-6-yl)phenyl)acetamido)-N-hydroxyheptanamide;
methyl 4-(1H-indol-6-yl)phenyl(7-(hydroxyamino)-7-oxoheptyl)carbamate;
7-(1-(4-(1H-indol-6-yl)phenyl)-3-(2-methoxyphenyl)ureido)-N-hydroxyheptanamide;
7-(1-(4-(1H-indol-6-yl)phenyl)-3-(3,5-dimethoxyphenyl)ureido)-N-hydroxyheptanamide;
7-(N-(4-(1H-indol-6-yl)phenyl)-5-amino-2-methoxyphenylsulfonamido)-N-hydroxyheptanamide;
7-(1-(4-(1H-indol-6-yl)phenyl)-3-(thiophen-2-yl)ureido)-N-hydroxyheptanamide;
7-(N-(4-(1H-indol-6-yl)phenyl)pyridine-3-sulfonamido)-N-hydroxyheptanamide;
7-(N-(4-(1H-indol-6-yl)phenyl)methylsulfonamido)-N-hydroxyheptanamide;
7-(N-(4-(1H-indol-6-yl)phenyl)-2-(dimethylamino)acetamido)-N-hydroxyheptanamide;
4-methoxyphenyl 4-(1H-indol-6-yl)phenyl(7-(hydroxyamino)-7-oxoheptyl)carbamate;
ethyl 4-(1H-indol-6-yl)phenyl(7-(hydroxyamino)-7-oxoheptyl)carbamate;
7-(1-(4-(1H-indol-6-yl)phenyl)-3,3-dimethylureido)-N-hydroxyheptanamide;
2-methoxyethyl 4-(1H-indol-6-yl)phenyl(7-(hydroxyamino)-7-oxoheptyl)carbamate;
N-(7-(hydroxyamino)-7-oxoheptyl)-N-(4-(1-methyl-1H-indazol-6-yl)phenyl)nicotinamide;
N-hydroxy-7-(4-(1-methyl-1H-indazol-6-yl)phenylamino)heptanamide;
7-(N-(4-(1H-indol-6-yl)phenyl)propionamido)-N-hydroxyheptanamide;
N-(4-(1H-indol-6-yl)phenyl)-N-(7-(hydroxyamino)-7-oxoheptyl)-1-methyl-1,2,5,6-tetrahydropyridine-3-carboxamide;
7-(1-(4-(1H-indol-6-yl)phenyl)-3-(pyridin-3-yl)ureido)-N-hydroxyheptanamide;
7-(1-(4-(1H-indol-6-yl)phenyl)-3-methylureido)-N-hydroxyheptanamide;
7-(N-(4-(1H-indol-6-yl)phenyl)ethylsulfonamido)-N-hydroxyheptanamide;
7-((4-(1H-indol-6-yl)phenyl)(N,N-dimethylsulfamoyl)amino)-N-hydroxyheptanamide;
N-(4-(1H-indol-6-yl)phenyl)-N-(7-(hydroxyamino)-7-oxoheptyl)cyclohexanecarboxamide;
N-(4-(1H-indol-6-yl)phenyl)-N-(7-(hydroxyamino)-7-oxoheptyl)cyclopropanecarboxamide;
7-(N-(4-(1H-indol-6-yl)phenyl)-2-morpholinoacetamido)-N-hydroxyheptanamide;
(S)—N-(4-(1H-indol-6-yl)phenyl)-N-(7-(hydroxyamino)-7-oxoheptyl)pyrrolidine-2-carboxamide;
7-(1-(4-(1H-indol-6-yl)phenyl)-3-isopropylureido)-N-hydroxyheptanamide;
7-(1-(4-(1H-indol-6-yl)phenyl)-3-isobutylureido)-N-hydroxyheptanamide;

N-hydroxy-7-(N-(4-(1-methyl-1H-indazol-6-yl)phenyl)methylsulfonamido)heptanamide;
7-((4-(1H-indol-6-yl)phenyl)(propyl)amino)-N-hydroxyheptanamide;
7-(N-(4-(1H-indol-6-yl)phenyl)-2-(4-methylpiperazin-1-yl)acetamido)-N-hydroxyheptanamide;
7-(1-(4-(1H-indol-6-yl)phenyl)-3-butylureido)-N-hydroxyheptanamide;
7-(1-(4-(1H-indol-6-yl)phenyl)-3-(4-methylpentyl)ureido)-N-hydroxyheptanamide;
7-(1-(4-(1H-indol-6-yl)phenyl)-3-(3-(dimethylamino)propyl)ureido)-N-hydroxyheptanamide;
7-(1-(4-(1H-indol-6-yl)phenyl)-3-(cyclohexylmethyl)ureido)-N-hydroxyheptanamide;
7-(N-(4-(1H-indol-6-yl)phenyl)pentanamido)-N-hydroxyheptanamide;
7-(N-(4-(1H-indol-6-yl)phenyl)isobutyramido)-N-hydroxyheptanamide;
7-(N-(4-(1H-indol-6-yl)phenyl)-2-(4-(2-methoxyethyl)piperazin-1-yl)acetamido)-N-hydroxyheptanamide;
7-(1-(4-(1H-indol-6-yl)phenyl)-3,3-diethylureido)-N-hydroxyheptanamide;
7-(1-(4-(1H-indol-6-yl)phenyl)-3-ethylureido)-N-hydroxyheptanamide;
N-hydroxy-7-(N-(4-(2-methyl-1H-indol-5-yl)phenyl)methylsulfonamido)heptanamide;
isobutyl 4-(1H-indol-6-yl)phenyl(7-(hydroxyamino)-7-oxoheptyl)carbamate;
N-(4-(1H-indol-6-yl)phenyl)-N-(7-(hydroxyamino)-7-oxoheptyl)thiophene-2-carboxamide;
N-(7-(hydroxyamino)-7-oxoheptyl)-N-(4-(1-methyl-1H-indazol-6-yl)phenyl)picolinamide;
7-(N-(4-(1H-indol-5-yl)phenyl)methylsulfonamido)-N-hydroxyheptanamide;
N-(4-(1H-indol-6-yl)phenyl)-N-(7-(hydroxyamino)-7-oxoheptyl)-1-methylpiperidine-4-carboxamide;
N-(4-(1H-indol-5-yl)phenyl)-N-(7-(hydroxyamino)-7-oxoheptyl)picolinamide;
N-(4-(1H-indol-6-yl)phenyl)-N-(7-(hydroxyamino)-7-oxoheptyl)morpholine-4-carboxamide;
7-(N-(4-(1,2-dimethyl-1H-indol-5-yl)phenyl)methylsulfonamido)-N-hydroxyheptanamide;
N-(4-(1H-indol-6-yl)phenyl)-N-(7-(hydroxyamino)-7-oxoheptyl)-4-methylpiperazine-1-carboxamide;
N-hydroxy-7-(N-(4-(1-methyl-1H-indazol-6-yl)phenyl)ethylsulfonamido)heptanamide;
N-(4-(1H-indol-5-yl)phenyl)-N-(7-(hydroxyamino)-7-oxoheptyl)nicotinamide;
N-(7-(hydroxyamino)-7-oxoheptyl)-4-methyl-N-(4-(1-methyl-1H-indazol-6-yl)phenyl)piperazine-1-carboxamide;
N-(4-(1H-indol-5-yl)phenyl)-N-(7-(hydroxyamino)-7-oxoheptyl)-4-methylpiperazine-1-carboxamide;
7-(N-(4-(1H-indol-5-yl)phenyl)ethylsulfonamido)-N-hydroxyheptanamide;
N-(7-(hydroxyamino)-7-oxoheptyl)-N-(4-(1-methyl-1H-indazol-6-yl)phenyl)morpholine-4-carboxamide;
N-(4-(1H-indol-5-yl)phenyl)-N-(7-(hydroxyamino)-7-oxoheptyl)morpholine-4-carboxamide;
N-(4-(1H-indol-6-yl)phenyl)-N-(7-(hydroxyamino)-7-oxoheptyl)-2,6-dimethylmorpholine-4-carboxamide;
N-(7-(hydroxyamino)-7-oxoheptyl)-2,6-dimethyl-N-(4-(1-methyl-1H-indazol-6-yl)phenyl)morpholine-4-carboxamide;
N-(4-(1H-indol-5-yl)phenyl)-N-(7-(hydroxyamino)-7-oxoheptyl)-2,6-dimethylmorpholine-4-carboxamide;
N-hydroxy-7-(N-(4-(1-methyl-1H-indol-5-yl)phenyl)methylsulfonamido)heptanamide;
N-hydroxy-7-(N-(4-(1-methyl-1H-indol-6-yl)phenyl)methylsulfonamido)heptanamide;
N-(4-(1H-indol-6-yl)phenyl)-N-(7-(hydroxyamino)-7-oxoheptyl)-4-isopropylpiperazine-1-carboxamide;
N-(4-(1H-indol-6-yl)phenyl)-N-(7-(hydroxyamino)-7-oxoheptyl)picolidine-1-carboxamide;
N-(4-(1H-indol-5-yl)phenyl)-N-(7-(hydroxyamino)-7-oxoheptyl)isonicotinamide;
7-(N-(6-(1H-indol-6-yl)pyridin-3-yl)methylsulfonamido)-N-hydroxyheptanamide;
N-hydroxy-7-(N-(6-(1-methyl-1H-indazol-6-yl)pyridin-3-yl)methylsulfonamido)heptanamide;
7-(N-(6-(1H-indol-5-yl)pyridin-3-yl)methylsulfonamido)-N-hydroxyheptanamide;
N-(4-(1H-indol-6-yl)phenyl)-4-acetyl-N-(7-(hydroxyamino)-7-oxoheptyl)piperazine-1-carboxamide;
N-(4-(1H-indol-6-yl)phenyl)-N-(7-(hydroxyamino)-7-oxoheptyl)-4-methyl-1,4-diazepane-1-carboxamide;
N-(7-(hydroxyamino)-7-oxoheptyl)-4-methyl-N-(4-(1-methyl-1H-indol-6-yl)phenyl)piperazine-1-carboxamide;
7-(N-(4-(1H-indol-2-yl)phenyl)methylsulfonamido)-N-hydroxyheptanamide;
tert-butyl 2-(4-(N-(7-(hydroxyamino)-7-oxoheptyl)methylsulfonamido)phenyl)-1H-indole-1-carboxylate;
N-(7-(hydroxyamino)-7-oxoheptyl)-4-methyl-N-(4-(2-methyl-1H-indol-5-yl)phenyl)piperazine-1-carboxamide;
N-(4-(1H-indol-6-yl)phenyl)-4-benzyl-N-(7-(hydroxyamino)-7-oxoheptyl)piperazine-1-carboxamide;
4-ethyl-N-(7-(hydroxyamino)-7-oxoheptyl)-N-(4-(1-methyl-1H-indazole-6-yl)phenyl)piperazine-1-carboxamide;
7-(N-(4-(5-bromo-1H-indol-2-yl)phenyl)methylsulfonamido)-N-hydroxyheptanamide;
tert-butyl 5-bromo-2-(4-(N-(7-(hydroxyamino)-7-oxoheptyl)methylsulfonamido)phenyl)-1H-indazole-1-carboxylate;
N-(4-(1H-indol-6-yl)phenyl)-4-ethyl-N-(7-(hydroxyamino)-7-oxoheptyl)piperazine-1-carboxamide;
N-(4-(1H-indol-6-yl)phenyl)-4-ethyl-N-(7-(hydroxyamino)-7-oxoheptyl)piperazine-1-carboxamide;
N-(7-(hydroxyamino)-7-oxoheptyl)-4-methyl-N-(4-(1-methyl-1H-indol-5-yl)phenyl)piperazine-1-carboxamide;
N-hydroxy-7-(4-methyl-N-(4-(1-methyl-1H-indazol-6-yl)phenyl)piperazine-1-sulfonamide)heptanamide;
N-(4-(1H-indol-6-yl)phenyl)-N-(7-(hydroxyamino)-7-oxoheptyl)-4-(2-methoxyphenyl)piperazine-1-carboxamide;
N-(4-(1H-indol-6-yl)phenyl)-N-(7-(hydroxyamino)-7-oxoheptyl)-4-(3-methoxyphenyl)piperazine-1-carboxamide;
N-(4-(3H-benzo[d]imidazol-5-yl)phenyl)-N-(7-(hydroxyamino)-7-oxoheptyl)-4-methylpiperazine-1-carboxamide;
N-(4-(1H-indol-6-yl)phenyl)-N-(7-(hydroxyamino)-7-oxoheptyl)-4-(2-hydroxyethyl)piperazine-1-carboxamide;
7-(3-(2-(dimethylamino)ethyl)-1-(4-(1-methyl-1H-indazol-6-yl)phenyl)ureido)-N-hydroxyheptanamide;
N-hydroxy-7-(1-(4-(1-methyl-1H-indazol-6-yl)phenyl)-3-(2-(1-methylpyrrolidin-2-yl)ethyl)ureido)heptanamide;

N-(4-(1H-indol-6-yl)phenyl)-4-butyl-N-(7-(hydroxyamino)-7-oxoheptyl)piperazine-1-carboxamide;
N-(7-(hydroxyamino)-7-oxoheptyl)-4-methyl-N-(4-(1-methyl-1H-indazol-5-yl)phenyl)piperazine-1-carboxamide;
4-ethyl-N-(7-(hydroxyamino)-7-oxoheptyl)-N-(4-(1-methyl-1H-indazol-5-yl)phenyl)piperazine-1-carboxamide;
N-(4-(1H-indol-6-yl)phenyl)-4-(2-(dimethylamino)ethyl)-N-(7-(hydroxyamino)-7-oxoheptyl)piperazine-1-carboxamide;
7-(3-((1-ethylpyrrolidin-2-yl)methyl)-1-(4-(1-methyl-1H-indazol-6-yl)phenyl)ureido)-N-hydroxyheptanamide;
7-(N-(4-(1H-indol-6-yl)phenyl)-4-methylpiperazine-1-sulfonamido)-N-hydroxyheptanamide;
7-(N-(4-(1H-indol-5-yl)phenyl)-4-methylpiperazine-1-sulfonamido)-N-hydroxyheptanamide;
N-(4-(1H-indol-6-yl)phenyl)-N-(7-(hydroxyamino)-7-oxoheptyl)-4-methylpiperazine-1-carboxamide;
7-(N-(4-(1H-indol-6-yl)phenyl)-4-methylpiperazine-1-carbothioamido)-N-hydroxyheptanamide;
7-(N-(4-(1H-indol-5-yl)phenyl)-4-methylpiperazine-1-carbothioamido)-N-hydroxyheptanamide; and
N-hydroxy-7-(4-methyl-N-(4-(1-methyl-1H-indazol-5-yl)phenyl)piperazine-1-carbothioamido)heptaneamide.

7. The hydroxamate compound, isomers thereof, pharmaceutically acceptable salts thereof, or hydrates thereof according to claim 6, wherein the hydroxamate derivatives are selected from the group consisting of the following compounds:
N-(7-(hydroxyamino)-7-oxoheptyl)-4-methyl-N-(4-(1-methyl-1H-indazol-6-yl)phenyl)piperazine-1-carboxamide;
N-(7-(hydroxyamino)-7-oxoheptyl)-4-methyl-N-(4-(2-methyl-1H-indol-5-yl)phenyl)piperazine-1-carboxamide;
4-ethyl-N-(7-(hydroxyamino)-7-oxoheptyl)-N-(4-(1-methyl-1H-indazol-6-yl)phenyl)piperazine-1-carboxamide; and
N-hydroxy-7-(4-methyl-N-(4-(1-methyl-1H-indazol-6-yl)phenyl)piperazine-1-sulfonamido)heptanamide.

8. Pharmaceutical compositions comprising hydroxamate compound of formula I, isomers thereof, pharmaceutically acceptable salts thereof, or hydrates thereof according to claim 1 together with pharmaceutically acceptable carriers.

9. A method for treating colon cancer, non-small cell lung cancer, or prostate cancer, the method comprising administering pharmaceutical compositions comprising hydroxamate compound of formula I, isomers thereof, pharmaceutically acceptable salts thereof, or hydrates thereof according to claim 1, together with pharmaceutically acceptable carriers.

10. A method for preparing hydroxamate compounds of the following formula I-2 derivatives, the method comprising the steps of:
allowing a compound of the following formula II to react with bromoaniline in the presence of an inorganic salt so as to prepare a compound of the following formula III;
allowing the compound of formula III to react with 4-nitrophenylchloroformate so as to prepare a compound of the following formula VI;
subjecting the compound of formula VI to the Suzuki reaction with boronic acid in the presence of palladium to prepare a compound of the following formula VII;
allowing the compound of formula VII to react with an amine in the presence of an inorganic salt so as to prepare a compound of the following formula VIII; and treating the compound of formula VIII with a hydroxide salt, thus preparing a hydroxamate derivative of the following formula I-2:

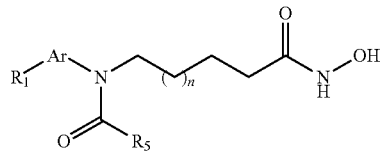

[Formula I-2]

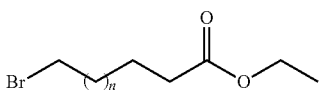

[Formula II]

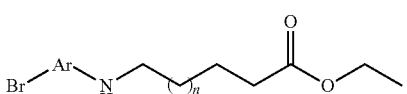

[Formula III]

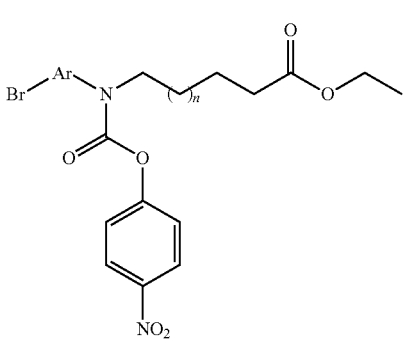

[Formula VI]

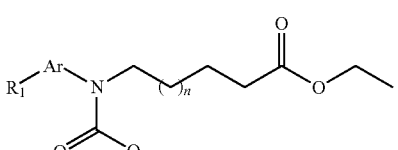

[Formula VII]

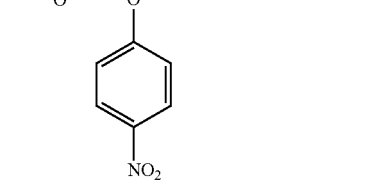

[Formula VIII]

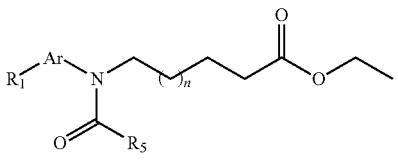

wherein n is 3, Ar is phenyl, $R_1$ is 1H-indol-5-yl, 1-methyl-1H-indazol-6-yl, 1-methyl-1H-indazol-5-yl, 3H-benzo[d]imidazol-5-yl, or 1H-indol-6-yl, and $R_5$ is 1-methylpiperazine, morpholine, 2,6-dimethylmorpholine, 1-ethylpiperazine, N,N-dimethylethane-1,2-diamine, 2-(1-methylpyrrolidin-2-yl)ethanamine, (1-ethylpyrrolidin-2-yl)methanamine, 4-methoxy benzenamine, 3-methoxy benzenamine, 2-methoxy benzenamine, 3,5-dimethoxy benzenamine, thiophen-2-amine, dimethylamine, pyridine-3-amine, methylamine, isopropylamine, isobutylamine, butylamine, 4-methylpentylamine, N,N-dimethylpropane-1,3-diamine, cyclohexylmethylamine, diethylamine, ethylamine, 1-isopropylpiperazine, pyrrolidine, 1-(piperazin-1-yl)ethanone, 1-methylhomopiperazine, 1-benzylpiperazine, 1-(2-methoxyphenyl)piperazine, 1-(3-methoxyphenyl)piperazine, 2-(piperazin-1-yl)ethanol, 1-butylpiperazine, N,N-dimethyl-2-(piperazin-1-yl)ethanamine, or 4-methylpiperidine.

* * * * *